United States Patent [19]

Demuth, Jr. et al.

[11] Patent Number: 5,646,163

[45] Date of Patent: Jul. 8, 1997

[54] QUINOLONE 5-(N-HETEROSUBSTITUTED AMINO) ANTIMICROBIALS

[75] Inventors: Thomas Prosser Demuth, Jr., Montgomery; Ronald Eugene White, West Chester, both of Ohio

[73] Assignee: The Procter & Gamble Company, Cincinnati, Ohio

[21] Appl. No.: 235,003

[22] Filed: Apr. 28, 1994

Related U.S. Application Data

[63] Continuation-in-part of Ser. No. 968,960, Oct. 30, 1992, abandoned.

[51] Int. Cl.$^6$ .................... A61K 31/47; C07D 215/233; C07D 215/58
[52] U.S. Cl. ............. 514/312; 544/363; 546/156
[58] Field of Search ............. 546/156; 514/312; 544/363

[56] References Cited

U.S. PATENT DOCUMENTS

| | | | |
|---|---|---|---|
| 4,623,650 | 11/1986 | Gilligan et al. | 514/312 |
| 4,665,079 | 5/1987 | Culbertson et al. | 514/312 |
| 4,795,751 | 1/1989 | Matsumoto et al. | 514/254 |
| 4,822,801 | 4/1989 | Domagala et al. | 514/312 |
| 4,945,160 | 7/1990 | Kiely et al. | 540/481 |
| 4,954,507 | 9/1990 | Weber et al. | 514/300 |

FOREIGN PATENT DOCUMENTS

| | | |
|---|---|---|
| 13811/88 | 10/1988 | Australia . |
| 0 172 651 | 2/1986 | European Pat. Off. . |
| 0 221 463 | 5/1987 | European Pat. Off. . |
| 0 342 649 | 11/1989 | European Pat. Off. . |
| 264759 | 10/1990 | Japan . |
| 91/16327 | 10/1991 | WIPO . |

OTHER PUBLICATIONS

Wolfson, J.S. and D.C. Hooper, "The Fluoroquinolones: Structures, Mechanisms of Action and Resistance, and Spectra of Activity In Vitro", Antimicrobial Agents and Chemotherapy, vol. 28, pp. 581–586 (1985).

Domagala, J.M. et al., "7–Substituted 5–Amino–1–cyclopropyl–6,8–difluoro–1,4–dihydro–4–oxo–3–quinolinecarboxylic Acids: Synthesis and Biological Activity of a New Class of Quinolone Antibacterials", J. Med. Chem., vol. 31, pp. 503–506 (1988).

Domagala, J.M., et al., "5–Amino–7–(3–Amino–1–Pyrrolidinyl)–1–Cyclopropyl–6,8–Difluoro–1,4–Dihydro–4–Oxo–3–Quinolinecarboxylic Acid (PD 124,816), Synthesis and Biological Evaluation of a New Class of Quinolone Antibacterials", Drugs Exptl. Clin. Res., XIV(7), pp. 453–460 (1988).

Ross, D.L. and C.M. Riley, "Aqueous Solubilities of Some Variously Substituted Quinolone Antimicrobials", International Journal of Pharmaceutics, vol. 63, pp. 237–250 (1990).

Rosen, T., "The Fluoroquinolone Antibacterial Agents", Progress In Medicinal Chemistry, vol. 27, pp. 235–295 (1990).

Miyamoto, T., et al., "Synthesis and Structure–Activity Relationships of 5–Substituted 6,8–Difluoroquinolones, Including Sparfloxacin, a New Quinolone Antibacterial Agent with Improved Potency", J. Med. Chem., vol. 33, pp. 1645–1656 (1990).

Chu, D. T. W., "Isothiazoloquinolones: Antibacerial and Antineoplastic Agents", Drugs of the Future, vol. 17, No. 12, pp. 1101–1109 (Dec. 1992).

(List continued on next page.)

Primary Examiner—C. Warren Ivy
Assistant Examiner—D. Margaret M. Mach
Attorney, Agent, or Firm—Carl J. Roof; Richard A. Hake; William J. Winter

[57] ABSTRACT

The invention relates to antimicrobial 5-(N-heterosubstituted amino) quinolone compounds having a structure according to Formula (I) or (II):

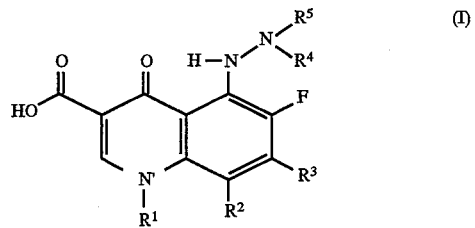

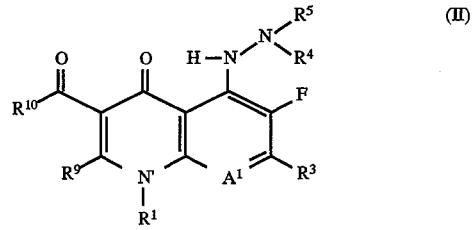

wherein (1) $R^1$, $R^2$, $R^3$, $R^9$ and $R^{10}$ form any of a variety of quinolone and related heterocyclic structures similar to those known in the art to have antimicrobial activity; and (2)
(a) $R^4$ and $R^5$ are, independently, hydrogen; lower alkyl; cycloalkyl; heteroalkyl; or —C(=O)—X—$R^8$, where X is a covalent bond, N, O, or S, and $R^8$ is lower alkyl, lower alkenyl, arylalkyl, a carbocylic ring, or a heterocyclic ring; or
(b) $R^4$ and $R^5$ together comprise a heterocyclic ring that includes the nitrogen to which they are bonded;

and the pharmaceutically-acceptable salts, biohydrolyzable esters, biohydrolyzable amides, and solvates thereof. The invention also relates to compositions comprising these compounds, as well as methods for treating infectious disorders using the compounds and/or compositions of the present invention.

20 Claims, No Drawings

OTHER PUBLICATIONS

Chu, D. T. W. and A. K. Claiborne, "Practical Synthesis of Iminochlorothioformates: Application of Iminochlorothioformates in the Synthesis of Novel, 2,3,4,9-Tetrahydroisothiazolo[5,4-β][1,8]naphthyridine-3,4-diones and 2,3,4,9-Tetrahydroisothiazolo[5-4,-β]quinoline-3,4-dione Derivatives", J. Heterocyclic Chem., vol. 27, pp. 1191-1195 (Jul.-Aug. 1990).

Chu, D. T. W., P. B. Fernandes, A. K. Claiborne, L. Shen, and A. G. Pernet, "Structure-Activity Relationships in Quinolone Antibacterials: Design, Synthesis and Biological Activities of Novel Isothiazoloquinolones", Drugs Exptl. Clin. Res., vol. XIV, No. 6, pp. 379-383 (Nov./Dec. 1988).

Inoue, Y., H. Kondo, M. Taguchi, Y. Jinbo, F. Sakamoto and G. Tsukamoto, "Synthesis and Antibacterial Activity of Thiazolopyrazine-Incorporated Tetracyclic Quinolone Antibacterials", J. Med. Chem., vol. 37, No. 5, pp. 586-592 (Mar. 1994).

Jinbo, Y., H. Kondo, Y. Inoue, M. Taguchi, H. Tsujishita, Y. Kotera, F. Sakamoto and G. Tsukamoto, "Synthesis and Antibacterial Activity of a New Series of Tetracyclic Pyridone Carboxylic Acids", J. Med. Chem., vol. 36, No. 18, pp. 2621-2626 (Sep. 1993).

Kotera, Y., Y. Inoue, M. Ohashi, K. Ito and G. Tsukamoto, "Antibacterial Activity of a New Tetracyclic Quinolone, No. 5290, against Norfloxacin- and Ciprofloxacin-Resistant Strains of *Staphylococus aureus*", Chem. Pharm. Bul., vol. 39, No. 10, p. 2644-2646 (Oct. 1991).

Kotera, Y. and S. Mitsuhashi, "In Vitro and In Vivo Antibacterial Activities of KB-5246, a New Tetracyclic Quinolone", Antimicrobial Agents and Chemotherapy, vol. 33, No. 11, pp. 1896-1900 (Nov. 1989).

Taguchi, M., H. Kondo, Y. Inoue, Y. Kawahata, Y. Jinbo, F. Sakamoto and G. Sukamoto, "Synthesis and Antibacterial Activity of new Tetracyclic Quinolone Antibacterials", J. Med. Chem., vol. 35, No. 1, pp. 94-99 (1992).

Chemical Abstracts 121:97532, 1994.

Chemical Abstracts 117:204280, 1991.

Chemical Abstracts 121:179620, 1994.

Chemical Abstracts 117:191731, 1992.

Chemical Abstracts 121:30943, 1993.

Chemical Abstracts 117:131483, 1992.

Chemical Abstracts 120:153006, 1994.

Chemical Abstracts 117:90162, 1992.

QUINOLONE 5-(N-HETEROSUBSTITUTED AMINO) ANTIMICROBIALS

This is a continuation-in-part of application Ser. No. 07/968,960, filed on Oct. 30, 1992 now abandoned.

BACKGROUND OF THE INVENTION

This invention relates to novel antimicrobial compounds, compositions, and methods of treatment. In particular, the compounds of this invention comprise a quinolone or related heterocyclic moiety.

The chemical and medical literature describes a myriad of compounds that are said to be antimicrobial, i.e., capable of destroying or suppressing the growth or reproduction of microorganisms, such as bacteria. In particular, antibacterials include a large variety of naturally-occurring (antibiotic), synthetic, or semi-synthetic compounds. They may be classified (for example) as the aminoglycosides, ansamacrolides, beta-lactams (including penicillins and cephalosporins), lincosaminides, macrolides, nitrofurans, nucleosides, oligosaccharides, peptides and polypeptides, phenazines, polyenes, polyethers, quinolones, tetracyclines, and sulfonamides. Such antibacterials and other antimicrobials are described in *Antibiotics, Chemotherapeutics, and Antibacterial Agents for Disease Control* (M. Grayson, editor, 1982), and E. Gale et al., *The Molecular Basis of Antibiotic Action* 2d edition (1981), both incorporated by reference herein.

The mechanism of action of these antibacterials vary. However, each can be generally classified as functioning in one or more of four ways: by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins (PBPs) in bacteria, which are responsible for cell wall synthesis. On the other hand, quinolones act by inhibiting synthesis of bacterial DNA, thus preventing the bacteria from replicating.

Not surprisingly, the pharmacological characteristics of antibacterials and other antimicrobials, and their suitability for any given clinical use, also vary considerably. For example, the classes of antimicrobials (and members within a class) may vary in their relative efficacy against different types of microorganisms, and their susceptibility to development of microbial resistance. These antimicrobials may also differ in their pharmacological characteristics, such as their bioavailability, and biodistribution. Accordingly, selection of an appropriate antibacterial (or other antimicrobial) in any given clinical situation can be a complicated analysis of many factors, including the type of organism involved, the desired method of administration, and the location of the infection to be treated.

The pharmaceutical literature is replete with attempts to develop improved antimicrobials (i.e., compounds that have a broader scope of activity, greater potency, improved pharmacology, and/or less susceptibility to resistance development.) For example, one group of antimicrobials that has been developed relatively recently for clinical use is the quinolones. These compounds include, for example, nalidixic acid, difloxacin, enoxacin, fleroxacin, norfloxacin, lomefloxacin, ofloxacin, ciprofloxacin, and pefloxacin. See, C. Marchbanks and M. Dudley, "New Fluoroquinolones", 7 *Hospital Therapy* 18 (1988); P. Shah, "Quinolones", 31 *Prog. Drug Res.* 243 (1987); *Quinolones—Their Future in Clinical Practice*, (A. Percival, editor, Royal Society of Medical Services, 1986); and M. Parry, "Pharmacology and Clinical Uses of Quinolone Antibiotics", 116 *Medical Times* 39 (1988).

However, many such attempts to produce improved antimicrobials have produced equivocal results. Indeed, few antimicrobials are developed that are truly clinically-acceptable in terms of their spectrum of antimicrobial activity, avoidance of microbial resistance, and pharmacology. For example, the quinolones often show reduced effectiveness against certain clinically important pathogens (for example, gram positive bacteria and/or anaerobic bacteria). The quinolones also have limited water solubility limiting their bioavailability and suitability for parenteral dosing. They may also produce adverse side effects, such as gastrointestinal disturbance and central nervous system effects (such as convulsions). See, M. Neuman and A. Esanu, "Gaps and Perspectives of New Fluoroquinolones", 24 *Drugs Exptl. Clin. Res.* 385 (1988); W. Christ et al., "Specific Toxicologic Aspects of the Quinolones", 10 *Rev. Infectious Diseases* S141 (1988); H. Neu, "Clinical Use of the Quinolones", *Lancet* 1319 (1987); and "Ciprofloxacin: Panacea or Blunder Drug?", *J. South Carolina Med. Assoc* 131 (March 1989).

SUMMARY OF THE INVENTION

The present invention provides compounds having a structure according to Formula (I), or a pharmaceutically-acceptable salt, biohydrolyzable ester, biohydrolyzable amide, or solvate thereof:

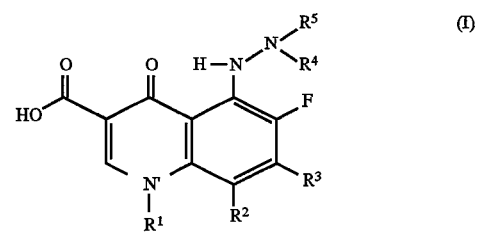

wherein (A)
(1)
(a) $R^1$ is alkyl; alkenyl; a carbocyclic ring; a heterocyclic ring; or —$N(R^6)(R^7)$, where $R^6$ and $R^7$ are, independently, hydrogen, alkyl, alkenyl, a carbocyclic ring, a heterocyclic ring, or $R^6$ and $R^7$ together comprise a heterocyclic ring that includes the nitrogen to which they are bonded; and
(b) $R^2$ is hydrogen, halogen, lower alkyl, or lower alkoxy; or
(2) $R^1$ and $R^2$ may together comprise a six-membered heterocyclic ring that includes N' and the carbon atom to which $R^2$ is bonded;
(B) $R^3$ is a heterocyclic ring or a carbocyclic ring; and
(C)
(1) $R^4$ and $R^5$ are, independently, hydrogen; lower alkyl; cycloalkyl; heteroalkyl; or —$C(=O)$—X—$R^8$, where X is a covalent bond, N, O, or S, and $R^8$ is lower alkyl, lower alkenyl, arylalkyl, a carbocyclic ring, or a heterocyclic ring; or
(2) $R^4$ and $R^5$ together comprise a heterocyclic ring that includes the nitrogen to which they are bonded.

The present invention also provides compounds having a structure according to Formula (II), or a pharmaceutically-acceptable salt, biohydrolyzable ester, biohydrolyzable amide, or solvate thereof:

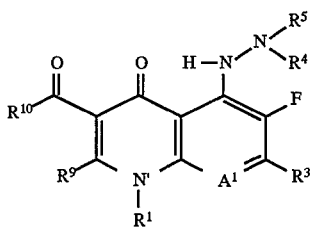

wherein (A)
(1) $A^1$ is N or $C(R^2)$, where $R^2$ is hydrogen, halogen, lower alkyl, or lower alkoxy;

(2) $R^1$ is alkyl; alkenyl; a carbocyclic ring; a heterocyclic ring; or —$N(R^6)(R^7)$, where $R^6$ and $R^7$ are, independently, hydrogen, alkyl, alkenyl, a carbocyclic ring, a heterocyclic ring, or $R^6$ and $R^7$ together comprise a heterocyclic ring that includes the nitrogen to which they are bonded; and (3) $R^3$ is a heterocyclic ring or a carbocyclic ring;

(4)
(a) $R^4$ and $R^5$ are, independently, hydrogen; lower alkyl; cycloalkyl; heteroalkyl; or —C(=O)—X—$R^8$, where X is a covalent bond, N, O, or S, and $R^8$ is lower alkyl, lower alkenyl, arylalkyl, a carbocyclic ring, or a heterocyclic ring; or (b) $R^4$ and $R^5$ together comprise a heterocyclic ring that includes the nitrogen to which they are bonded;

(5) $R^9$ is hydrogen; and
(6) $R^{10}$ is hydroxy;

(B) and
(1) when $A^1$ is $C(R^2)$, $R^2$ and $R^3$ may together comprise a substituted or unsubstituted heterocyclic ring or a substituted or unsubstituted carbocyclic ring;

(2) $R^9$ and $R^{10}$ may together comprise a substituted heterocyclic ring;

(3) $R^1$ and $R^9$ may together comprise a substituted or unsubstituted heterocyclic ring; and (4) when $A^1$ is $C(R^2)$, $R^1$ and $R^2$ may together comprise a substituted or unsubstituted heterocyclic ring comprising N' and $A^1$, and $R^1$ and $R^9$ may together comprise a substituted or unsubstituted heterocyclic ring comprising N' and the ring carbon atom of Formula (II) to which $R^9$ is bonded, such that the two heterocyclic rings are fused to one another;

wherein the compounds have at least three fused rings.

It has been found that the compounds of this invention, and compositions containing these compounds, are effective antimicrobial agents against a broad range of pathogenic microorganisms. It has also been discovered that, surprisingly, compounds of this invention offer significantly increased water solubility compared to related antimicrobials known in the art. Of particular importance is that the compounds of the present invention offer improved solubility at physiological pH. This surprising property may allow for, among other things, improved pharmacology, including increased serum levels upon administration, ease of formulation, and a more flexible dosing regimen.

DESCRIPTION OF THE INVENTION

The present invention encompasses certain novel quinolones and related heterocyclic analogs, methods for their manufacture, dosage forms, and methods of administering the quinolones to a human or other animal subject. Specific compounds and compositions to be used in the invention must, accordingly, be pharmaceutically acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio.

5-(N-heterosubstituted amino) quinolones

The compounds of this invention, herein referred to as "5-(N-heterosubstituted amino) quinolones", encompass any of a variety of quinolones (and related heterocyclic moieties) having an N-heteroamino substituent at the 5-position of the quinolone moiety.

The 5-(N-heterosubstituted amino) quinolones of this invention include compounds having a structure according to Formula (I), or a pharmaceutically-acceptable salt, biohydrolyzable ester, biohydrolyzable amide, or solvate thereof:

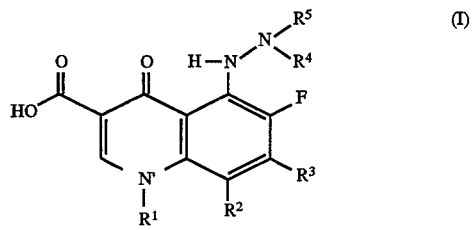

wherein (A)
(1)
(a) $R^1$ is alkyl; alkenyl, a carbocyclic ring; a heterocyclic ring; or —$N(R^6)(R^7)$ (preferably alkyl or a carbocyclic ring), where $R^6$ and $R^7$ are, independently, hydrogen, alkyl, alkenyl, a carbocyclic ring, a heterocyclic ring, or $R^6$ and $R^7$ together comprise a heterocyclic ring that includes the nitrogen to which they are bonded; and (b) $R^2$ is hydrogen, halogen, lower alkyl, or lower alkoxy (preferably halogen); or (2) (Preferably) $R^1$ and $R^2$ may together comprise a six membered heterocyclic ring that includes N' and the carbon atom to which $R^2$ is bonded;

(B) $R^3$ is a heterocyclic ring or a carbocyclic ring (preferably a heterocyclic ring); and (C)
(1) $R^4$ and $R^5$ are, independently, hydrogen; lower alkyl; cycloalkyl; heteroalkyl; or —C(=O)—X—$R^8$ (preferably hydrogen or lower alkyl), where X is a covalent bond, N, O, or S, and $R^8$ is lower alkyl, lower alkenyl, arylalkyl, a carbocyclic ring, or a heterocyclic ring; or (2) $R^4$ and $R^5$ together comprise a heterocyclic ring that includes the nitrogen to which they are bonded.

The 5-(N-heterosubstituted amino) quinolones of this invention further include compounds having a structure according to Formula (II), or a pharmaceutically-acceptable salt, biohydrolyzable ester, biohydrolyzable amide, or solvate thereof:

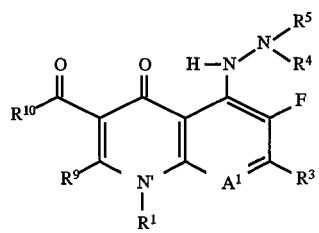

(II)

wherein (A)
(1) $A^1$ is N or (preferably) $C(R^2)$, where $R^2$ is hydrogen, (preferably) halogen, lower alkyl, or lower alkoxy;
(2) $R^1$ is alkyl; alkenyl; a carbocyclic ring; a heterocyclic ring (preferably alkyl or a carbocyclic ring); or —$N(R^6)(R^7)$, where $R^6$ and $R^7$ are, independently, hydrogen, alkyl, alkenyl, a carbocyclic ring, a heterocyclic ring, or $R^6$ and $R^7$ together comprise a heterocyclic ring that includes the nitrogen to which they are bonded; and
(3) $R^3$ is a heterocyclic ring or a carbocyclic ring (preferably a heterocyclic ring);
(4)
   (a) $R^4$ and $R^5$ are, independently, hydrogen; lower alkyl; cycloalkyl; heteroalkyl; or —C(=O)—X—$R^8$ (preferably hydrogen or lower alkyl), where X is a covalent bond, N, O, or S, and $R^8$ is lower alkyl, lower alkenyl, arylalkyl, a carbocyclic ring, or a heterocyclic ring; or
   (b) $R^4$ and $R^5$ together comprise a heterocyclic ring that includes the nitrogen to which they are bonded;
(5) $R^9$ is hydrogen; and
(6) $R^{10}$ is hydroxy;

(B) and
(1) when $A^1$ is $C(R^2)$, $R^2$ and $R^3$ may together comprise a substituted or unsubstituted heterocyclic ring or a substituted or unsubstituted carbocyclic ring (preferably a heterocyclic ring, more preferably a fused polycyclic heterocyclic ring);
(2) $R^9$ and $R^{10}$ may together comprise a substituted heterocyclic ring;
(3) $R^1$ and $R^9$ may together comprise a substituted or unsubstituted heterocyclic ring (preferably a 4 to 6 membered monocycle or a 9 to 12 atom fused polycycle); and
(4) when $A^1$ is $C(R^2)$, $R^1$ and $R^2$ may together comprise a substituted or unsubstituted heterocyclic ring (preferably having 5 or 6 ring atoms) comprising N' and $A^1$, and $R^1$ and $R^9$ together comprise a substituted or unsubstituted heterocyclic ring (preferably having from 4 to 7 ring atoms) comprising N' and the ring carbon atom of Formula (II) to which $R^9$ is bonded, such that the two heterocyclic rings are fused to one another;

wherein said compound has at least three fused rings.

Definitions and Usage of Terms:

The following is a list of definitions for terms used herein.

"Alkyl" is an unsubstituted or substituted saturated hydrocarbon chain radical having from 1 to 8 carbon atoms, preferably from 1 to 4 carbon atoms. Preferred alkyl groups include (for example) substituted or unsubstituted methyl, ethyl, propyl, isopropyl, and butyl.

"Alkenyl" is an unsubstituted or substituted hydrocarbon chain radical having from 2 to 8 carbon atoms, preferably from 2 to 4 carbon atoms, and having at least one olefinic double bond (including, for example, vinyl, allyl and butenyl).

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Alkylamino" is an amino radical having one or two alkyl substituents (i.e.,—N-alkyl).

"Arylalkyl" is an alkyl radical substituted with an aryl group. Preferred arylalkyl groups include benzyl and phenylethyl.

"Arylamino" is an amine radical substituted with an aryl group (i.e., —NH-aryl).

"Aryloxy" is an oxygen radical having an aryl substituent (i.e., —O-aryl).

"Acyl" or "carbonyl" is a radical formed by removal of the hydroxy from a carboxylic acid (i.e., R—C(=O)—). Preferred alkylacyl groups include (for example) acetyl, formyl, and propionyl.

"Acyloxy" is an oxygen radical having an acyl substituent (i.e., —O-acyl); for example,—O—C(=O)-alkyl.

"Acylamino" and "amido" both refer to an amino radical having an acyl substituent (i.e., —N-acyl); for example, —NH—C(=O)-alkyl.

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Cycloalkyl" is a saturated carbocyclic ring radical. Preferred cycloalkyl groups include (for example) cyclopropyl, cyclobutyl and cyclohexyl.

"Aryl" is an aromatic carbocyclic ring radical. Preferred aryl groups include (for example) phenyl, tolyl, xylyl, cumenyl and naphthyl.

"Fused rings" are rings that are superimposed together such that they show two ring atoms. A given ring may be fused to more than one other ring.

"Heteroatom" is a nitrogen, sulfur or oxygen atom. Groups containing one or more heteroatoms may contain different heteroatoms.

"Heteroalkyl" is an unsubstituted or substituted saturated chain radical having from 3 to 8 members comprising carbon atoms and one or two heteroatoms.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic heterocyclic rings contain from 3 to 9 atoms, preferably 4 to 6 atoms. Polycyclic rings contain from 7 to 17 atoms, preferably from 7 to 13 atoms.

"Heteroaryl" is an aromatic heterocyclic ring radical. Preferred heteroaryl groups include (for example) thienyl, furyl, pyrrolyl, pyridinyl, pyrazinyl, thiazolyl, pyrimidinyl, quinolinyl, and tetrazolyl.

"Halo", "halogen", or "halide" is a chloro, bromo, fluoro or iodo atom radical. Chloro and fluoro are preferred halides.

Also, as referred to herein, a "lower" hydrocarbon moiety (e.g., "lower" alkyl) is a hydrocarbon chain comprised of from 1 to 6, preferably from 1 to 4, carbon atoms.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium). Preferred anionic salts include the halides (such as chloride salts).

A "biohydrolyzable ester" is an ester of a 5-(N-heterosubstituted amino) quinolone that does not essentially interfere with the antimicrobial activity of the compounds, or that is readily converted in vivo by a human or lower animal subject to yield an antimicrobially-active 5-(N-heterosubstituted amino) quinolone. Such esters include those that do not interfere with the biological activity of quinolone antimicrobials. Many such esters are known in the art, as described in World Patent Publication 87/05297, Johnston et al., published Sep. 11, 1987, (incorporated by reference herein). Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methylcarbonyloxymethyl, ethoxycarbonyloxyethyl and isopropoxycarbonyloxyethyl esters), alkoxyalkyl esters, choline esters, and alkyl acylamino alkyl esters (such as acetamidomethyl esters).

A "biohydrolyzable amide" is an amide of a 5-(N-heterosubstituted amino) quinolone that does not essentially interfere with the antimicrobial activity of the compounds, or that is readily converted in vivo by a human or lower animal subject to yield an antimicrobially-active 5-(N-heterosubstituted amino) quinolone. Such amides include those that do not interfere with the biological activity of quinolone antimicrobials. Many such esters are known in the art, as described in World Patent Publication 93/13091 (1993); Ekhato et al., 33 (9) J. Labelled Compd. Radiopharm. 869–80 (1993); Japanese Patent Publication 05117280 (1993); Okada et al., 41(1) Chem. Pharm Bull. 126–31 (1993); World Patent Publication 92/03136 (1992); European Patent Publication 470,578 (1992); European Patent Publication 360,258 (1990); and European Patent Publication 304,087 (1989). Such amides include lower alkyl amides (e.g., acetamide, propionamide, etc.), amino acid amides (e.g., glycine amides, alanine amides, proline amides, etc.), polypeptide amides (e.g., alanylalanine amides, glycylproline amides, etc.), alkoxycarbonyl amides (e.g., methoxycarbonyl amides, benzyloxycarbonyl amides, etc.), and alkylaminocarbonyl amides (e.g., methylaminocarbonyl amides, ethylaminocarbonyl amides, etc.)

A "solvate" is a complex formed by the combination of a solute (e.g., a 5-(N-heterosubstituted amino) quinolone) and a solvent (e.g., water). See J. Honig et al., The Van Nostrand Chemist's Dictionary, p. 650 (1953). Pharmaceutically-acceptable solvents used according to this invention include those that do not interfere with the biological activity of the quinolone antimicrobials (e.g., water, ethanol, acetic acid, N,N-dimethylformamide).

As defined above and as used herein, substituent groups may themselves be substituted. Such substitution may be with one or more substituents. Such substituents include those listed in C. Hansch and A. Leo, Substituent Constants for Correlation Analysis in Chemistry and Biology (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

With respect to the compounds of Formula (I) and Formula (II), Groups $R^1$, $R^2$, $R^3$, $R^9$, and $R^{10}$ form any of a variety of quinolone moieties known in the art to have antimicrobial activity. Such moieties are well known in the art, as described in the following articles, all incorporated by reference herein: J. Wolfson et al., "The Fluoroquinolones: Structures, Mechanisms of Action and Resistance, and Spectra of Activity In Vitro", 28 Antimicrobial Agents and Chemotherapy 581 (1985); and T. Rosen et al., 31 J. Med Chem. 1586 (1988); T. Rosen et al., 31 J. Med. Chem. 1598 (1988); G. Klopman et al., 31 Antimicrob. Agents Chemother. 1831 (1987); 31:1831–1840; J. P. Sanchez et al., 31 J. Med. Chem. 983 (1988); J. M. Domagalia et al., 31 J. Med. Chem. 991 (1988); M. P. Wentland et al., in 20 Ann. Rep. Med. Chem. 145 (D. M. Baily, editor, 1986); J. B. Cornett et al., in 21 Ann. Rep. Med. Chem. 139 (D. M. Bailey, editor, 1986); P. B. Fernandes et al., in 22 Ann. Rep. Med. Chem. 117 (D. M. Bailey, editor, 1987); R. Albrecht, 21 Prog. Drug Research 9 (1977); P. B. Fernandes et al., in 23 Ann. Rep. Med. Chem. (R. C. Allen, editor, 1987); Quinolone Antimicrobial Agents, 2d edition (D. Hooper and J. Wolfson, editors, 1993); J. V. Heck 24 Ann. Rep Med. Chem. 101 (R. C. Allen, editor, 1989); M. J. Suto et at., 27 Ann. Rep. Med. Chem. 119 (1992); and M. L. Hammond, 28 Ann. Rep. Med. Chem. 119 (1993). Compounds of Formula (I):

$R^1$ is preferably alkyl, alkenyl, aryl, cycloalkyl, a heterocyclic ring, or alkylamino. More preferably, $R^1$ is ethyl, 2-fluoroethyl, 2-hydroxyethyl, t-butyl, 4-fluorophenyl, 2,4-difluorophenyl, methylamino, 3-oxetanyl, 2-fluorocyclopropyl, bicyclo [1.1.1] pentane, vinyl, or cyclopropyl. Cyclopropyl, 2-fluorocyclopropyl, t-butyl, 2-fluorocyclopropyl, and 2,4-difluorophenyl are particularly preferred $R^1$ groups. Preferred 5-(N-heterosubstituted amino) quinolones of Formula (I) also include those compounds where $R^1$ and $R^2$ together comprise a 6-membered heterocyclic ring, according to the formula:

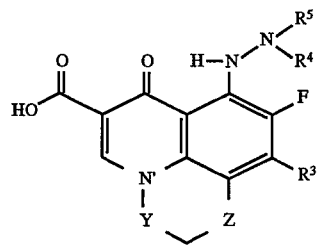

where Y is substituted or unsubstituted methyl, O, or N; and Z is O, S, N, or substituted or unsubstituted methyl. Preferred is where Y is substituted or unsubstituted methyl and Z is O or S; and where Y is N and Z is O or S.

Particularly preferred are compounds where $R^1$ and $R^2$ do not together form a heterocyclic ring.

$R^2$ is preferably chlorine, fluorine, methoxy, or methyl. Fluorine and chlorine are particularly preferred $R^2$ groups.

Preferred $R^3$ groups include nitrogen-containing heterocyclic rings. Particularly preferred are nitrogen-containing heterocyclic rings having from 5 to 8 members. The heterocyclic ring may contain additional heteroatoms, such as oxygen, sulfur, or nitrogen, preferably nitrogen. Such heterocyclic groups are described in U.S. Pat. No. 4,599,334, Petersen et al., issued Jul. 8, 1986; and U.S. Pat. No. 4,670,444, Grohe et al., issued Jun. 2, 1987 (both incorporated by reference herein). Preferred $R^3$ groups include unsubstituted or substituted pyridine, piperidine, morpholine, diazabicyclo[3.1.1]heptane, diazabicyclo

[2.2.1]heptane, diazabicyclo[3.2.1]octane, diazabicyclo[2.2.2]octane, imidazolidine, and 5-amino-3-azabicyclo[4.2.0]heptane, as well as particularly preferred $R^3$ groups which include piperazine, 3-methylpiperazine, 3-aminopyrrolidine, 3-aminomethylpyrrolidine, N,N-dimethylaminomethylpyrrolidine, N-ethylaminomethylpyrrolidine, 3,5-dimethylpyridine, N-methylpiperazine, 3,5-dimethylpiperazine, 3-(amino-1-ethyl)pyrollidine, and 3-methyl-1-amino morpholine.

Preferred $R^4$ and $R^5$ groups include those where $R^4$ and $R^5$ together comprise a heterocyclic ring containing the nitrogen atom to which they are bonded, those where both $R^4$ and $R^5$ are lower alkyl, those where one of $R^4$ or $R^5$ is hydrogen and the other is lower alkyl, and those where both $R^4$ and $R^5$ are hydrogen. More preferred groups are where one of $R^4$ or $R^5$ is hydrogen and the other is alkyl and those where both $R^4$ and $R^5$ are hydrogen. Particularly preferred groups are where both $R^4$ and $R^5$ are hydrogen.

Preferred compounds of the present invention include those having both an $R^3$ group that contains a basic nitrogen atom (including, for example, pyridine, piperidine, diazabicyclo[3.1.1]heptane, diazabicyclo-[2.2.1]heptane, diazabicyclo[3.2.1]octane, diazabicyclo[2.2.2]octane, and imidazolidine) and $R^4$ and $R^5$ groups that allow the nitrogen atom to which they are bonded to be basic (including, e.g., where $R^4$ and $R^5$ together comprise a heterocyclic ring containing the nitrogen to which they are bonded, both $R^4$ and $R^5$ are lower alkyl, one of $R^4$ and $R^5$ are lower alkyl and the other is hydrogen, or both $R^4$ and $R^5$ are hydrogen). Particularly preferred compounds are those where the $R^3$ group is one of piperazine, 3-methylpiperazine, 3-aminopyrrolidine, 3-aminomethylpyrrolidine, N,N-dimethylaminopyrrolidine, N-ethylaminomethylpyrrolidine, N-methylpiperazine, or 3,5-dimethylpiperazine; and both $R^4$ and $R^5$ are hydrogen.

As used herein, a "basic nitrogen atom" is one where the nitrogen atom possesses a lone pair of electrons that can be involved in ionic bonding with any of a variety of cations. It is understood in the art that the basicity of a nitrogen atom of a given moiety will depend on the nature of that nitrogen atom's covalent bonding. See, e.g., A. Streitwieser and C. Heathcock, *Introduction to Organic Chemistry*, 2d edition, pp. 734–40 (1981), incorporated by reference herein.

Preferred 5-(N-heterosubstituted amino) quinolones of Formula (I) include:

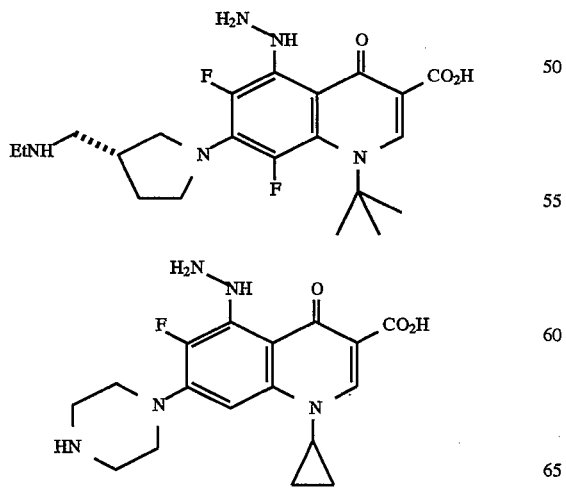

-continued

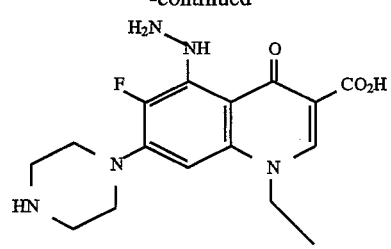

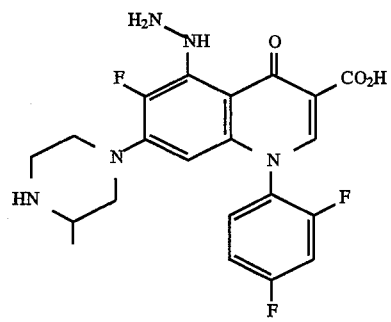

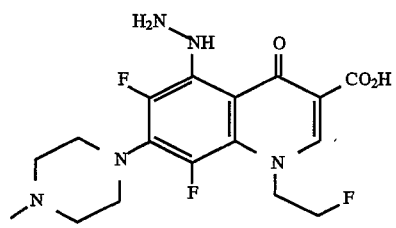

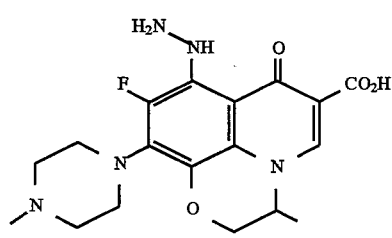

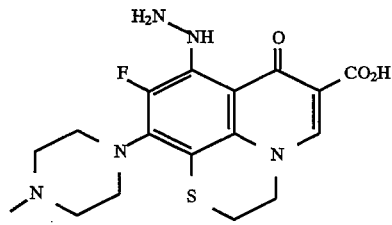

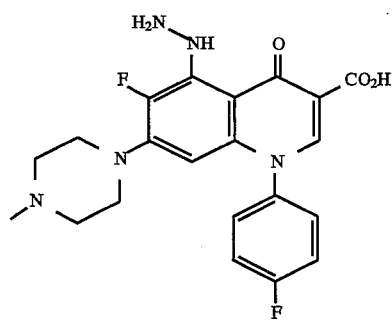

-continued
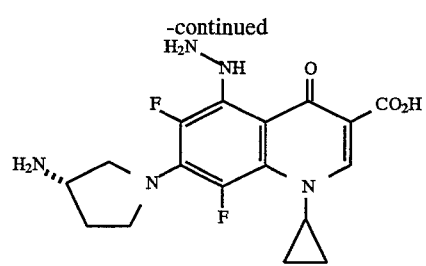
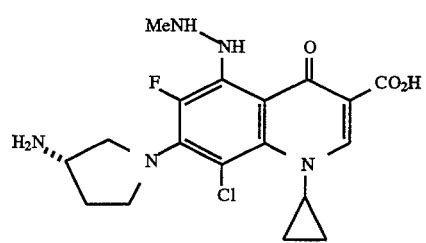
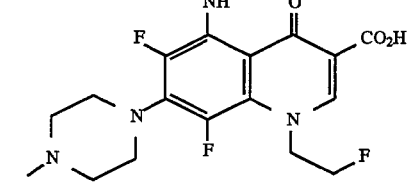
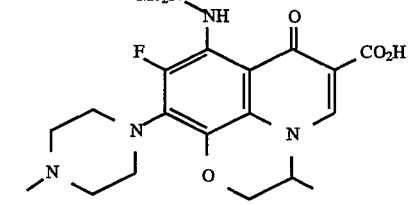
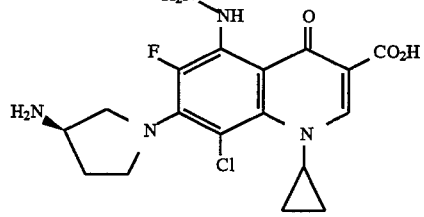
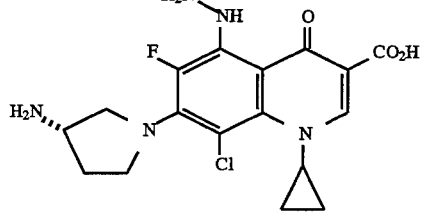
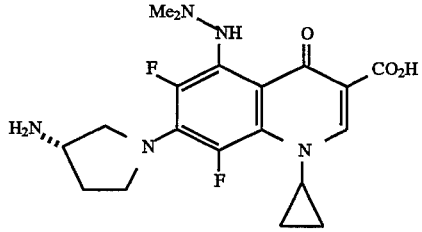
-continued
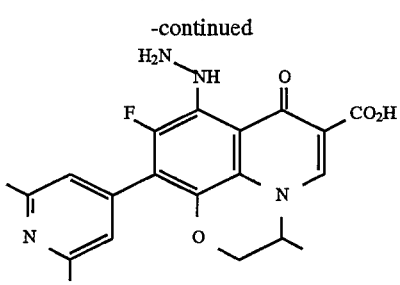
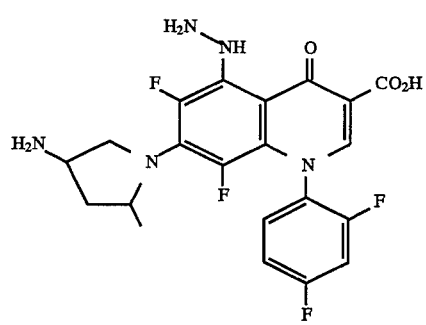
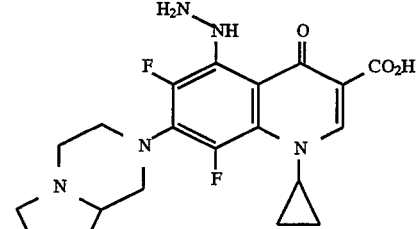
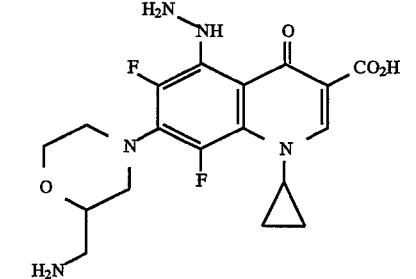
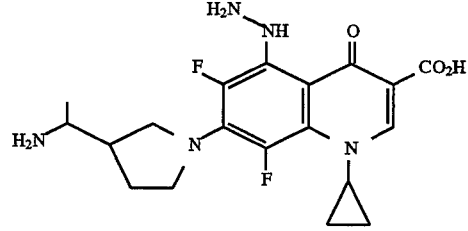
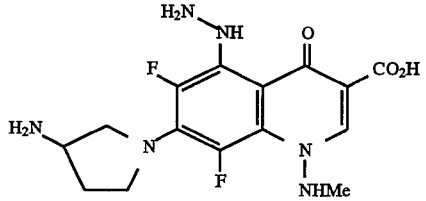

13
-continued
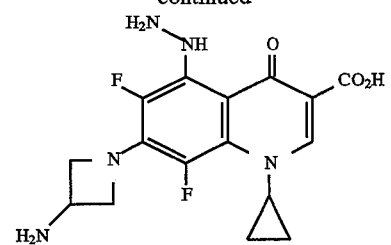
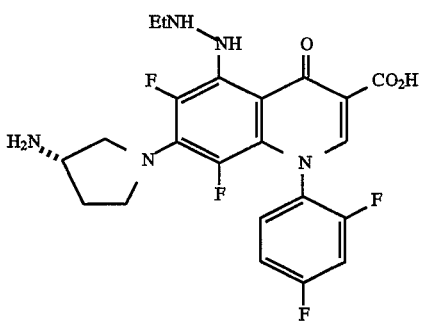
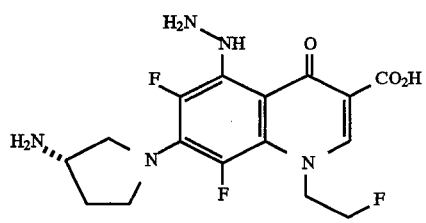
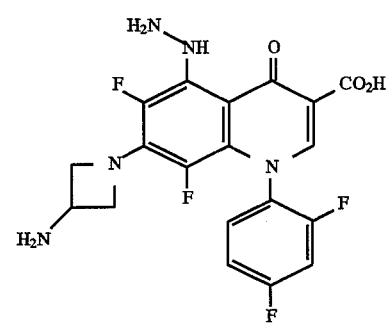
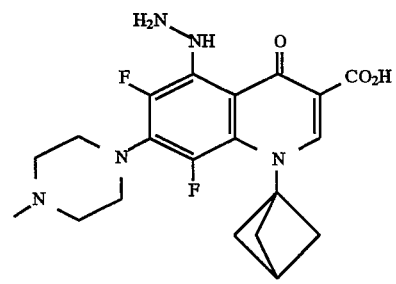
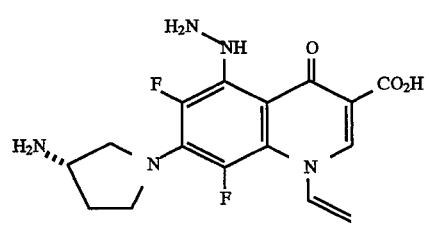
14
-continued
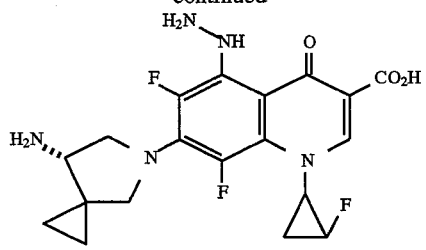
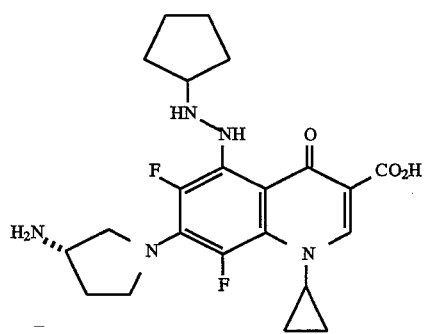
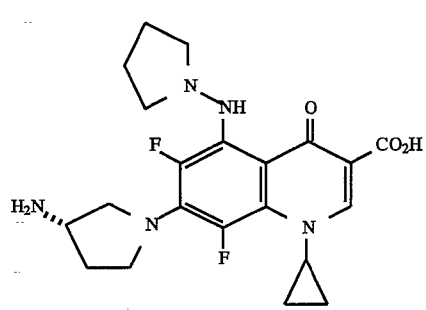
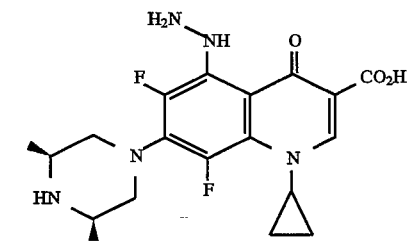
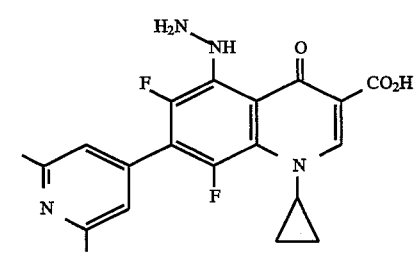
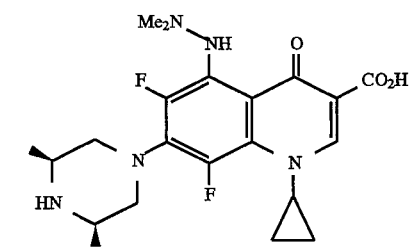

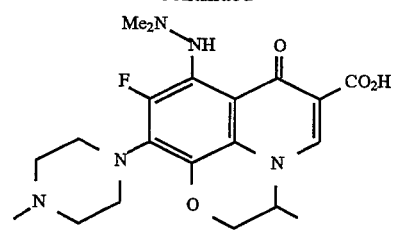
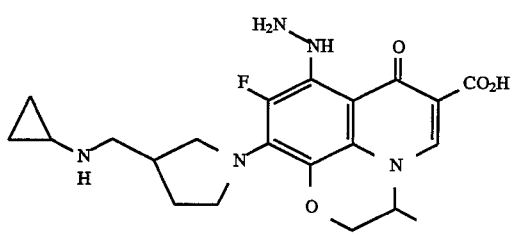
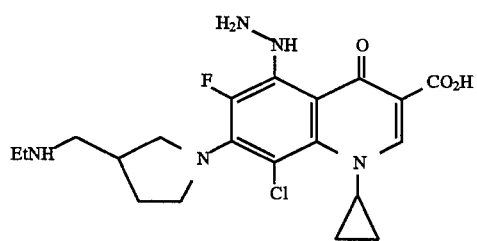
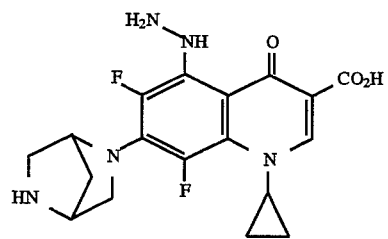
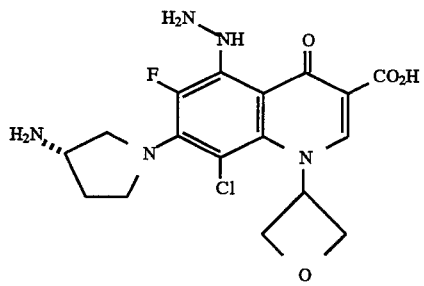
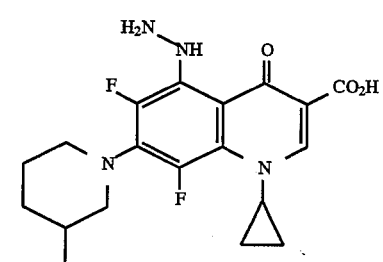
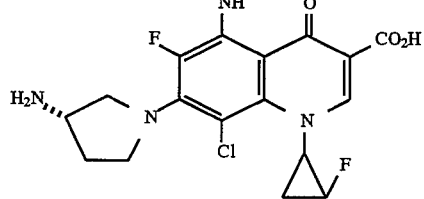
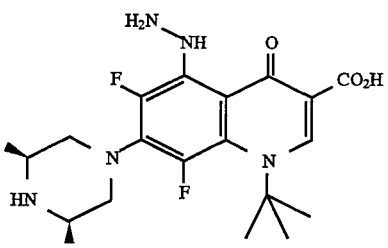
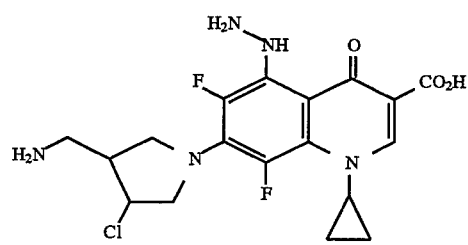
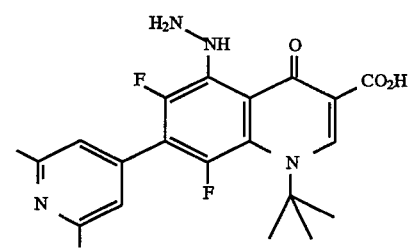
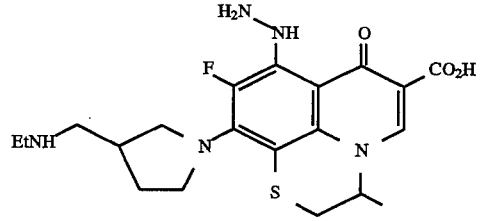
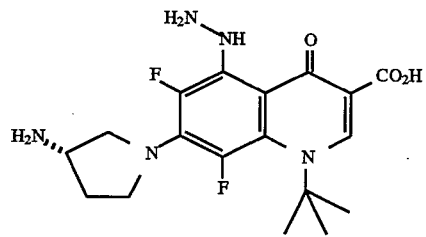
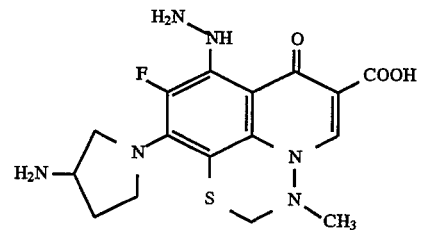

-continued

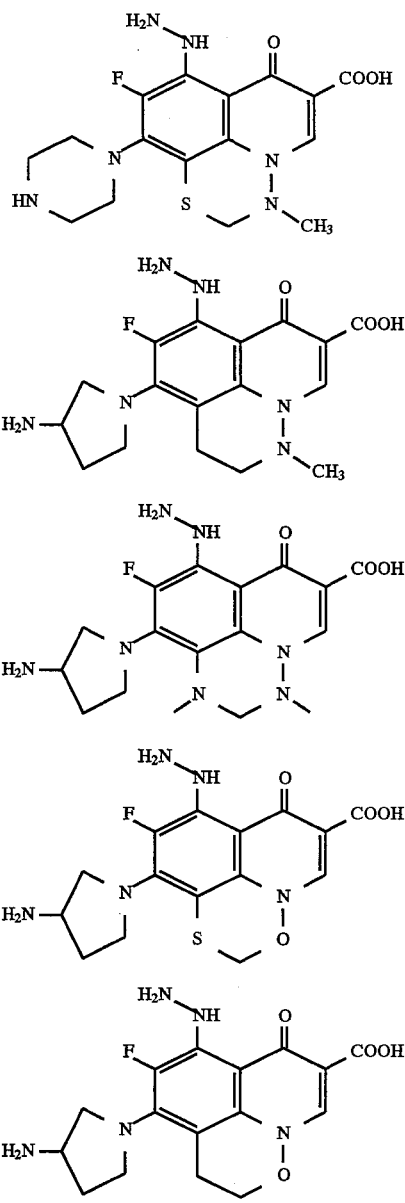

Compounds of Formula (II):

With respect to the compounds of Formula (II), preferred groups for R¹, R², R³, R⁴, and R⁵ are the same as those listed with respect to the compounds of Formula (I). Preferred are those compounds where A¹ is C(R²). According to the definitions discussed above, the compounds of Formula (II) have at least three fused rings. That is, in addition to the two fused rings depicted in Formula (II), at least one additional fused ring is present.

Multi-cyclic quinolones, and methods for their preparation, are known in the art. The following references are representative of the literature, and are incorporated by reference herein: South African Patent Publication 85502802 (1985); South African Patent Publication 8502769 (1985); Chu et al., 29(8) *J. Med. Chem.* 1531–34 (1986); Jinbo et al., 36 *J. Med. Chem.* 2621 (1993); Taguchi et al., 35(7) *J. Med. Chem.* 94 (1992); Kotera et al., 33(11) *Antimicrob. Agents Chemother.* 1896 (1989); European Patent Publication 216,345 (1987); Kompis et al., 29th *Conf. Antimicrob. Agents Chemother.*, Abstract 1250 (1989); Shimma et al., 31st *Conf. Antimicrob. Agents Chemother.*, Abstracts 1453 and 1454 (1991); U.S. Pat. No. 4,864,023, issued Sep. 5, 1989; Dax et al., 57 *J. Org. Chem.* 744–46 (1992); Segawa et al., 35 *J. Med. Chem.* 4727–38 (1992); Ozaki et al., 35 *Antimicrob. Agents Chemother.* 2490–95 (1991); Nishino et al., 29th *Conf. Antimicrob. Agents Chemother.*, Abstract 1253 (1989); and Chu et al., 21 *Advances in Drug Research* 39–144 (1991).

Preferred compounds of Formula (II) are those where $R^9$ and $R^{10}$ together form a substituted heterocyclic moiety. Particularly preferred are those compounds having a structure according to formula (a)

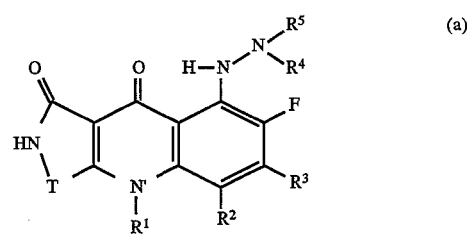

In formula (a), $R^9$ and $R^{10}$ together form a substituted five membered heterocycle; and T is N, O or S (preferably S).

Other preferred compounds of Formula (II) are those where $A^1$ is $C(R^2)$, $R^1$ and $R^2$ together comprise a substituted or unsubstituted heterocyclic ring comprising N' and $A^1$, and $R^1$ and $R^9$ together comprise a substituted or unsubstituted heterocyclic ring comprising N' and the ring carbon atom of Formula (II) to which $R^9$ is bonded, such that the two heterocyclic rings are fused to one another. Particularly preferred are those compounds having a structure according to formula (b)

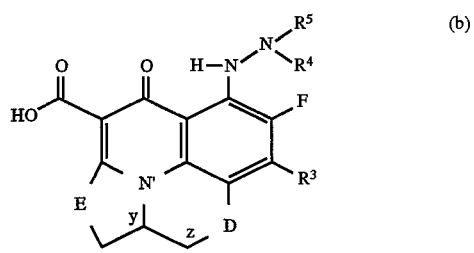

In formula (b), $R^1$ and $R^2$ together comprise a six-membered heterocycle comprising D, where D is O, S, a secondary or tertiary amine, or substituted or unsubstituted methyl, and where z is a single or double bond (preferably a single bond); and $R^1$ and $R^9$ together comprise a five-membered heterocycle ring comprising E, where E is O or S (preferably S), where y is a single or double bond (preferably a double bond). As indicated in formula (b), the heterocycles comprising E and D are fused to one another. This formula exemplifies compounds having four fused rings.

Other preferred compounds of Formula (II) are those where $R^1$ and $R^9$ together comprise a substituted or unsubstituted monocyclic heterocyclic ring. Particularly preferred are those compounds having a structure according to formula (c)

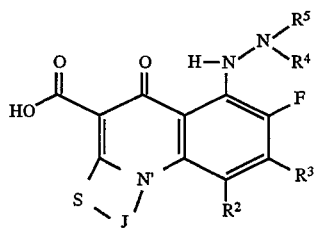

(c)

In formula (c), $R^1$ and $R^9$ together comprise a sulfur-containing heterocycle, where J is $C_1$–$C_3$ alkyl or alkenyl. Thus, the heterocycle containing J has from 4 to 6 ring atoms.

Still other preferred compounds of Formula (II) are those where $R^1$ and $R^9$ together comprise a substituted or unsubstituted polycyclic heterocyclic ring. Particularly preferred are those compounds having a structure according to formula (d)

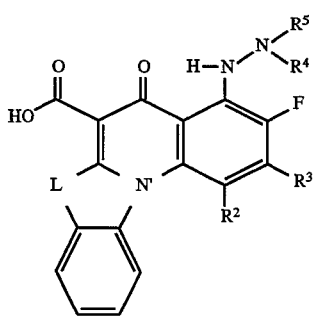

(d)

In formula (d), $R^1$ and $R^9$ together comprise a nine-membered polycyclic heterocycle, wherein L is O, N, or S.

Other preferred compounds of Formula (II) are those where $A^1$ is $C(R^2)$, and $R^2$ and $R^3$ together comprise a substituted or unsubstituted heterocyclic ring. Particularly preferred are those compounds having a structure according to formula (e)

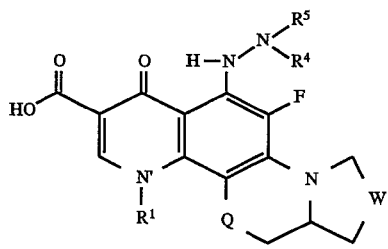

(e)

In formula (e), $R^2$ and $R^3$ together comprise a polycyclic heterocycle, wherein Q is O, secondary or tertiary amine, S, or substituted or unsubstituted methylene (preferably O); and W is substituted or unsubstituted $C_1$–$C_3$ alkyl.

Preferred 5-(N-heterosubstituted amino) quinolones of Formula (II), in addition to the compounds described in Examples 1 through 9 below, include the following:

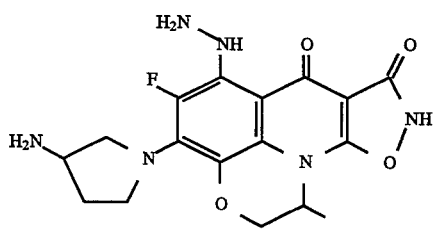

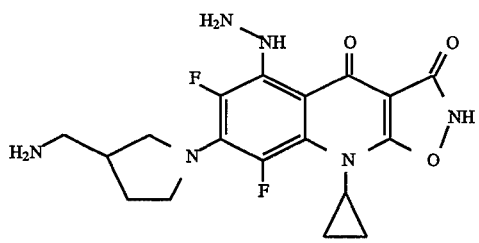

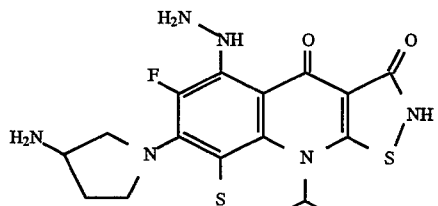

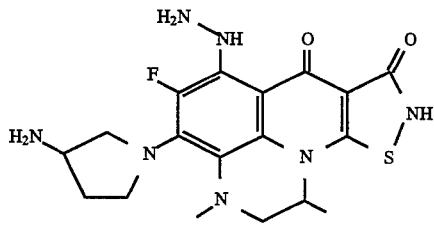

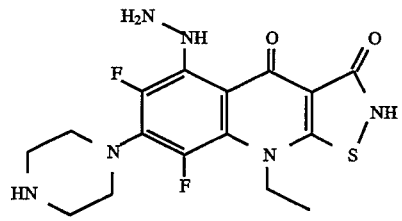

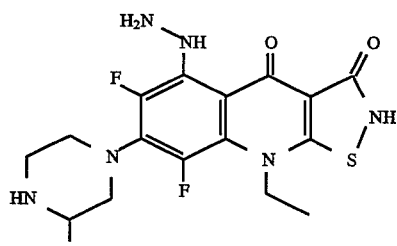

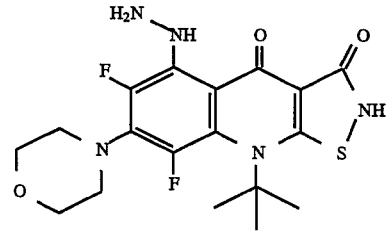

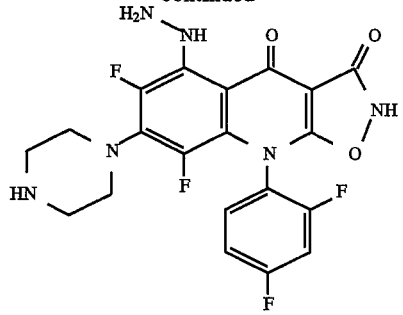
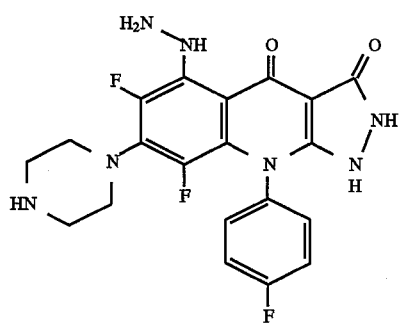
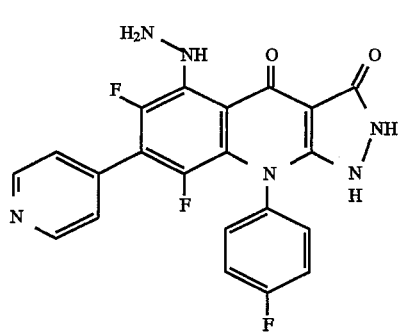
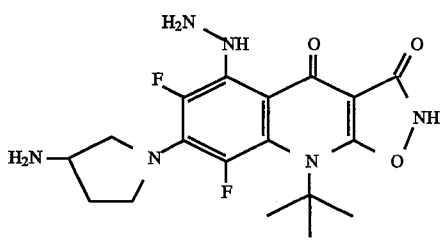
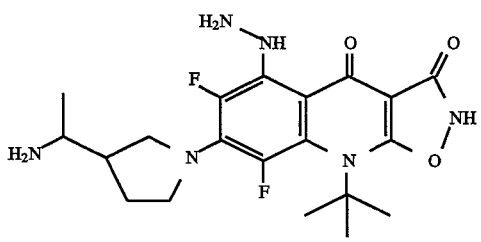
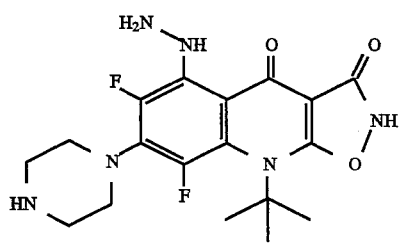
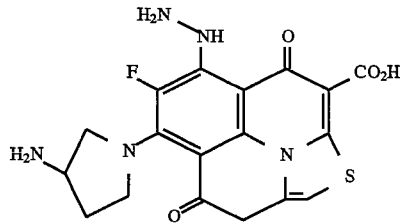
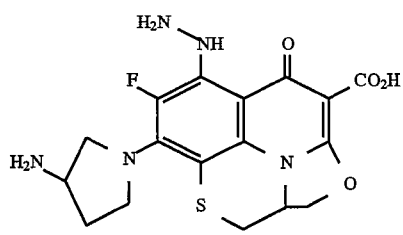
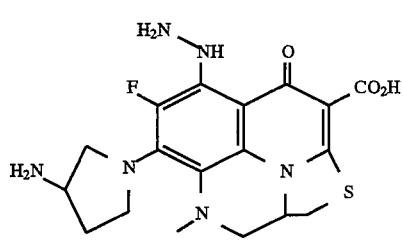
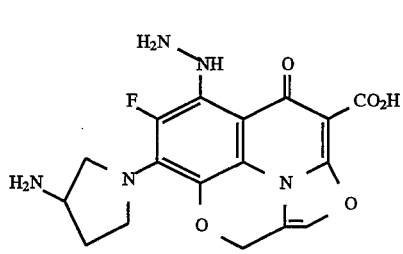
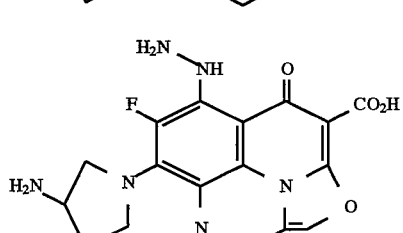
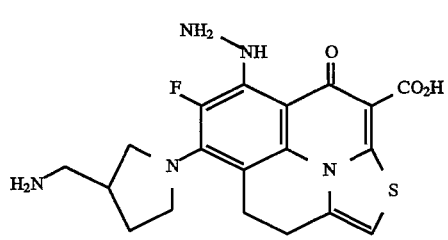
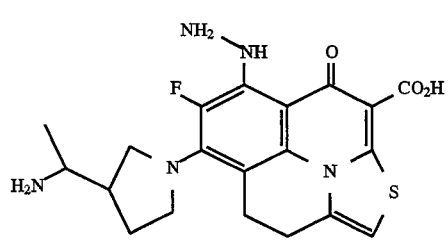

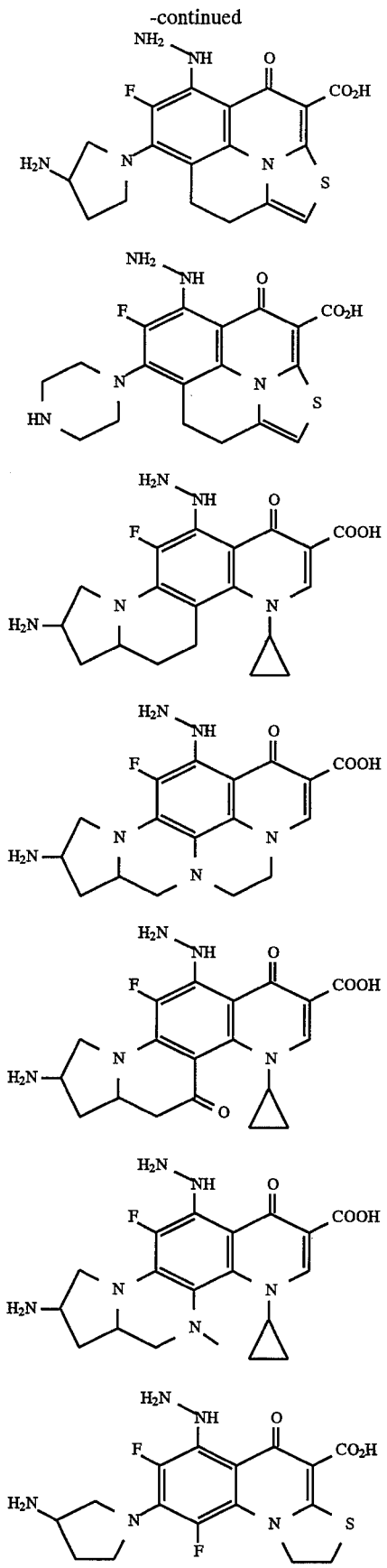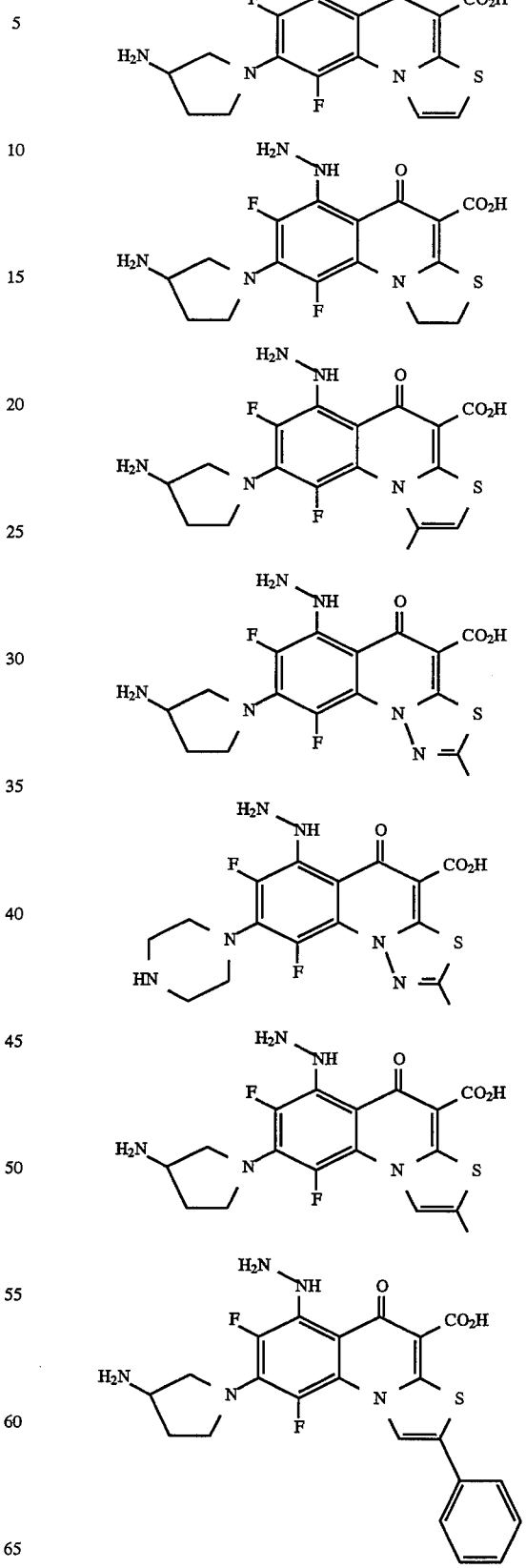

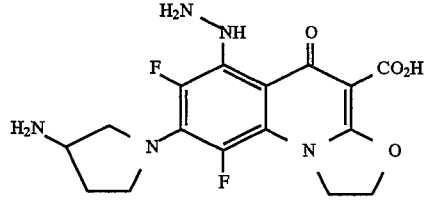
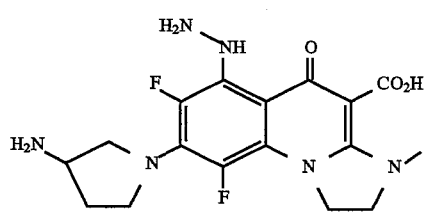
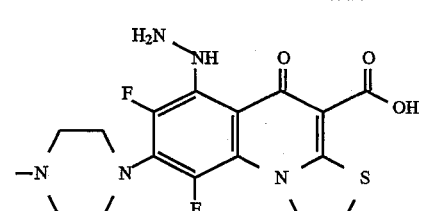
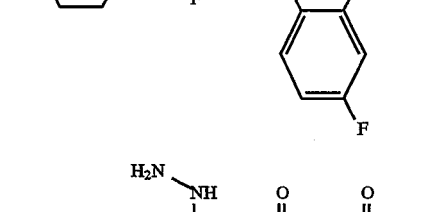
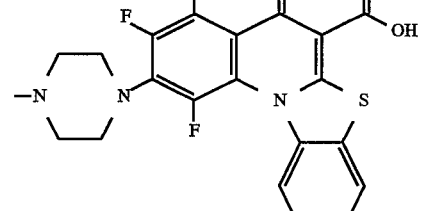
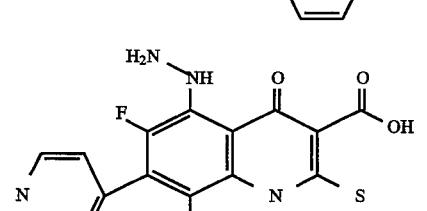
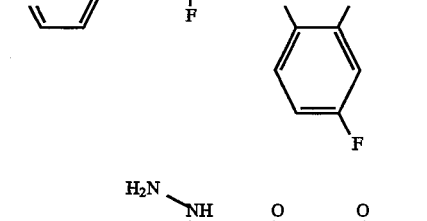
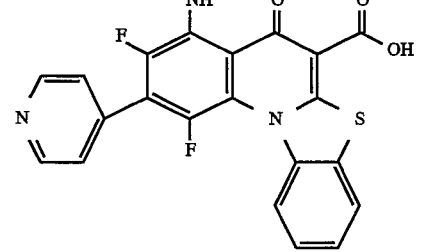
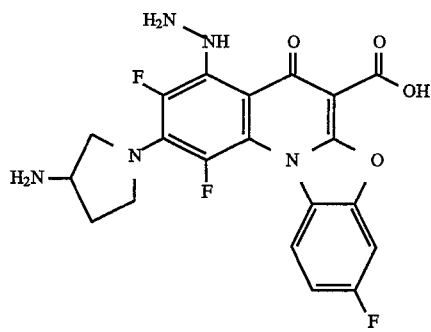
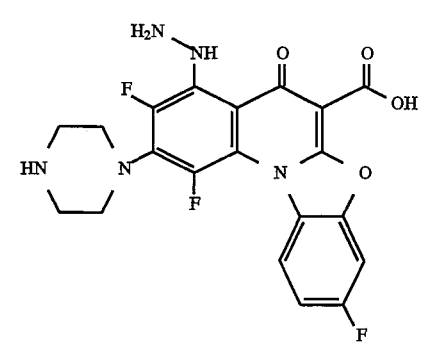
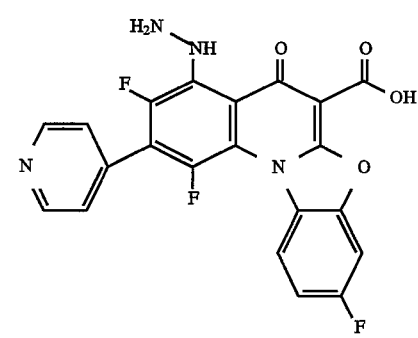
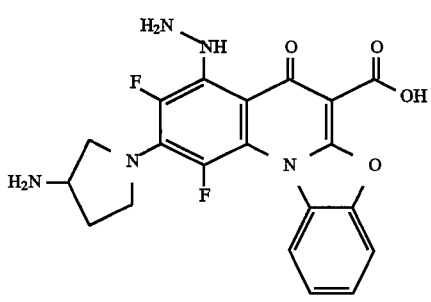
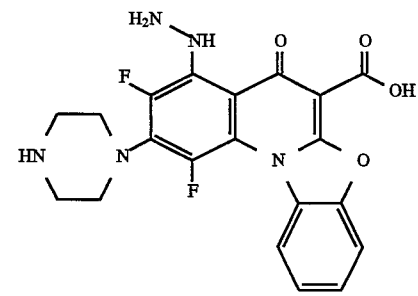

-continued

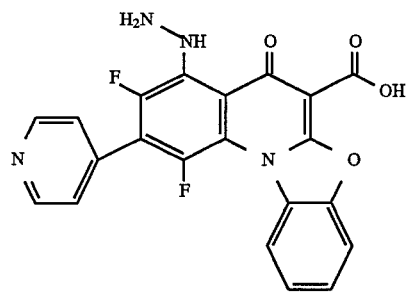

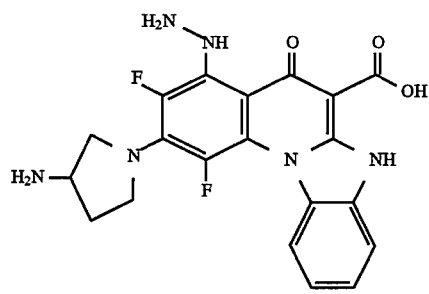

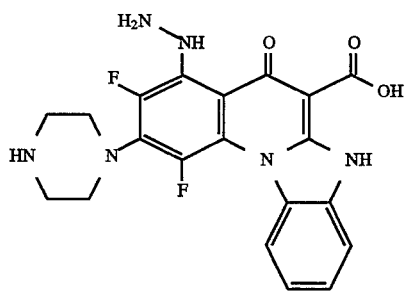

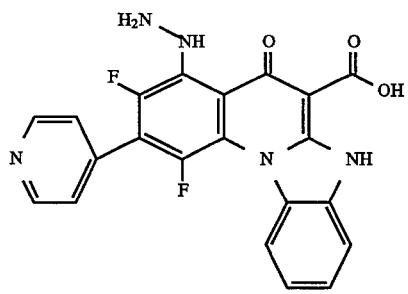

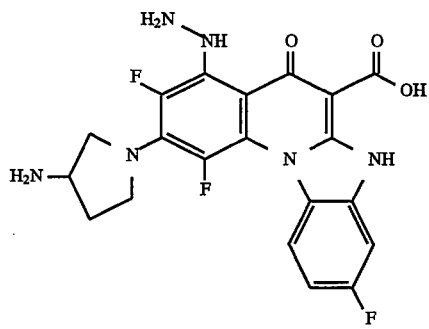

-continued

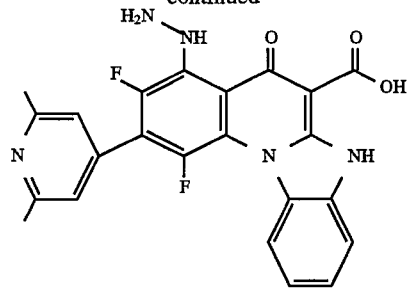

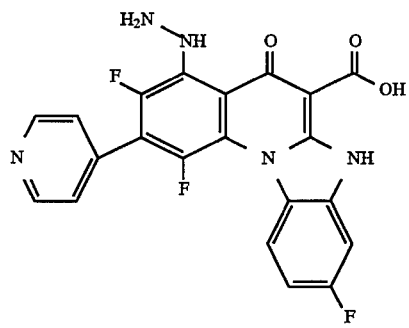

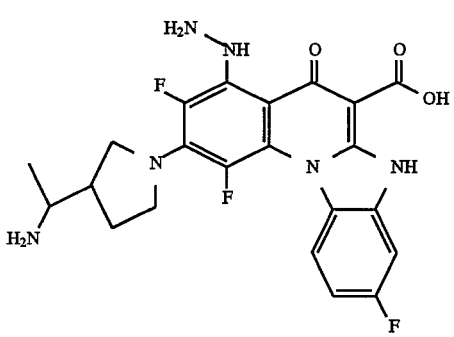

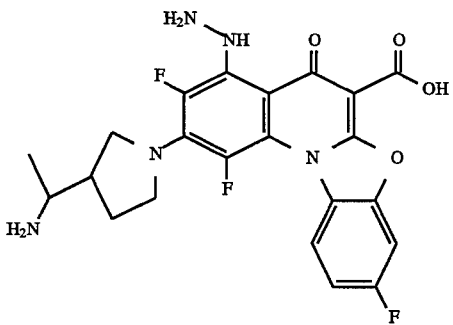

The compounds of this invention are also useful as intermediates in the synthesis of novel lactam-quinolones. Such lactam-quinolone compounds are disclosed in International Publication No. WO 91/16327, published Oct. 31, 1991, incorporated by reference herein. Lactam-quinolones encompass any of a variety of lactam moieties linked, by a linking moiety, to a quinolone moiety at the 5-position of the quinolone.

Lactam-quinolones include compounds having the general structure:

Q-L-B wherein Q, L and B are defined as follows:

(I) Q is a structure according to Formula (III)

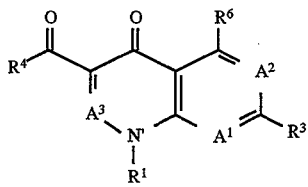

wherein (A)
(1) A1 is N or C(R$^7$); where
  (i) R$^7$ is hydrogen, hydroxy, alkoxy, nitro, cyano, halogen, alkyl, or N(R$^8$)(R$^9$) (preferably hydrogen or halogen), and
  (ii) R$^8$ and R$^9$ are, independently, R$^{8a}$, where R$^{8a}$ is hydrogen, alkyl, alkenyl, carbocyclic ring, or heterocyclic ring substituents; or R$^8$ and R$^9$ together comprise a heterocyclic ring including the nitrogen to which they are bonded;
(2) A$^2$ is N or C(R$^2$) (preferably C(R$^2$)); where R$^2$ is hydrogen or halogen;
(3) A$^3$ is N or (preferably) C(R$^5$); where R$^5$ is hydrogen;
(4) R$^1$ is hydrogen, alkyl, a carbocyclic ring, a heterocyclic ring, alkoxy, hydroxy, alkenyl, arylalkyl, or N(R$^8$)(R$^9$) (preferably alkyl or a carbocyclic ring);
(5) R$^3$ is hydrogen, halogen, alkyl, a carbocyclic ring, or a heterocyclic ring (preferably a heterocyclic ring);
(6) R$^4$ is hydroxy; and
(7) R$^6$ is R$^{15}$ or R$^{16}$X; where R$^{15}$ is a substituent moiety of L and is nil, alkyl, heteroalkyl, or alkenyl; R16 is a substituent moiety of L and is alkyl, alkenyl, a carbocyclic ring or a heterocyclic ring; and X is alkyl, heteroalkyl, alkenyl, oxygen, sulfur, or NH;

(B) except that
  (1) when A$^1$ is C(R$^7$), R$^1$ and R$^7$ may together comprise a heterocyclic ring including N' and A$^1$;
  (2) when A$^2$ is C(R$^2$), R$^2$ and R$^3$ may together comprise —O—(CH$_2$)n—O—, where n is an integer from 1 to 4;
  (3) when A$^3$ is C(R$^5$), R$^4$ and R$^5$ may together comprise a heterocyclic ring including the carbon atoms to which R$^4$ and R$^5$ are bonded and the carbon atom of Formula (I) to which said carbon atoms are bonded; and
  (4) when A$^3$ is C(R$^5$), R$^1$ and R$^5$ may together comprise a heterocyclic ring including N' and the adjacent carbon to which R$^5$ is bonded;

(II) B is a structure according to Formula (IV), where L is bonded to R$^{14}$:

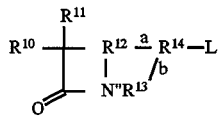

wherein (A) R$^{10}$ is hydrogen, halogen, heteroalkyl, a carbocyclic ring, a heterocyclic ring, R$^{8a}$—O—, R$^{8a}$CH=N—, (R$^8$)(R$^9$)N—, R$^{17}$—C(=CHR$^{20}$)—C(=O)NH—, or (preferably) alkyl, alkenyl, R$^{17}$—C(=NO—R$^{19}$)—C(=O)NH—, or R$^{18}$—(CH$_2$)m—C(=O)NH—; where
  (1) m is an integer from 0 to 9 (preferably from 0 to 3);
  (2) R$^{17}$ is hydrogen, alkyl, alkenyl, heteroalkyl, heteroalkenyl, a carbocyclic ring, or a heterocyclic ring (preferably alkyl, a carbocyclic ring, or a heterocyclic ring);
  (3) R$^{18}$ is R$^{17}$, —Y$^1$, or —CH(Y$^2$)(R$^{17}$);
  (4) R$^{19}$ is R$^{17}$, arylalkyl, heteroarylalkyl, —C(R$^{22}$)(R$^{23}$)COOH, —C(=O)O—R$^{17}$, or —C(=O)NH—R$^{17}$, where R$^{22}$ and R$^{23}$ are, independently, R$^{17}$ or together comprise a carbocyclic ring or a heterocyclic ring including the carbon atom to which R$^{22}$ and R$^{23}$ are bonded (preferably R$^{17}$ or —C(R$^{22}$)(R$^{23}$)COOH)
  (5) R$^{20}$ is R$^{19}$, halogen, —Y$^1$, or —CH(Y$^2$)(R$^{17}$) (preferably R$^{19}$ or halogen);
  (6) Y$^1$ is —C(=O)OR$^{21}$, —C(=O)R$^{21}$, —N(R$^{24}$)R$^{21}$, or —S(O)pR$^{29}$ or —OR$^{29}$; and Y$^2$ is Y$^1$ or —OH, —SH, or —SO$_3$H;
    (a) p is an integer from 0 to 2 (preferably 0);
    (b) R$^{24}$ is hydrogen; alkyl; alkenyl; heteroalkyl; heteroalkenyl; a carbocyclic ring; a heterocyclic ring; —SO$_3$H; —C(=O)R$^{25}$; or, when R$^{18}$ is —CH(N(R$^{24}$)R$^{21}$)(R$^{17}$), R$^{24}$ may comprise a moiety bonded to R$^{21}$ to form a heterocyclic ring; and
    (c) R$^{25}$ is R$^{17}$, NH(R$^{17}$), N(R$^{17}$)(R$^{26}$), O(R$^{26}$), or S(R$^{26}$) (preferably R$^{17}$, NH(R$^{17}$) or N(R$^{17}$)(R$^{26}$)); where R$^{26}$ is alkyl, alkenyl, a carbocyclic ring, a heterocyclic ring or (preferably) when R$^{25}$ is N(R$^{17}$)(R$^{26}$), R$^{26}$ may comprise a moiety bonded to R$^{17}$ to form a heterocyclic ring; and
  (7) R$^{21}$ is R$^{29}$ or hydrogen; where R$^{29}$ is alkyl; alkenyl; arylalkyl; heteroalkyl; heteroalkenyl; heteroarylalkyl; a carbocyclic ring; a heterocyclic ring; or, when Y$^1$ is N(R$^{24}$)R$^{21}$ and R$^{21}$ is R$^{29}$, R$^{21}$ and R$^{24}$ may together comprise a heterocyclic ring including the nitrogen atom to which R$^{24}$ is bonded (preferably hydrogen, alkyl, a carbocyclic ring or a heterocyclic ring);

(B) R$^{11}$ is hydrogen, halogen, alkoxy, or R$^{27}$C(=O)NH— (preferably hydrogen or alkoxy), where R$^{27}$ is hydrogen or alkyl (preferably hydrogen);

(C) bond "a" is a single bond or is nil; and bond "b" is a single bond, a double bond, or is nil; except bond "a" and bond "b" are not both nil;

(D) R$^{12}$ is —C(R$^{8a}$)—, or —CH$_2$—R$^{28}$— (preferably —C(R$^{8a}$)—); where R$^{28}$ is —C(R$^{8a}$), —O—, or —N—, and R$^{28}$ is directly bonded to N" in Formula (II) to form a 5-membered ring; except, if bond "a" is nil, then R$^{12}$ is
  (1) (preferably) —C(R$^{8a}$)(X$^1$)—, where
    (i) X$^1$ is —R$^{21}$; —OR$^{30}$; —S(O)rR$^{30}$, where r is an integer from 0 to 2 (preferably 0); —O(C=O)R$^{30}$; or N(R$^{30}$)R$^{31}$; and
    (ii) R$^{30}$ and R$^{31}$ are, independently, alkyl, alkenyl, carbocyclic ring or heterocyclic ring substituents; or R$^{30}$ and R$^{31}$ together comprise a heterocyclic ring including the nitrogen atom to which R$^{30}$ and R$^{31}$ are bonded; or
  (2) —CH$_2$—R$^{32}$—; where R$^{32}$ is —C(R$^{8a}$)(R$^{21}$), —O—, or —NR$^{8a}$, and R$^{32}$ is directly bonded to N" in Formula (II) to form a 5-membered ring;

(E)
  (1) if bond "b" is a single bond, R$^{13}$ is preferably —CH(R$^{33}$)—; or, —C(O)NHSO$_2$—, if bond "a" is nil; or —C*(R$^{33}$)—, if R$^{14}$ contains a R$^{36}$ moiety; where R$^{33}$ is hydrogen or COOH (preferably COOH), and C* is linked to R$^{36}$ to form a 3-membered ring;
  (2) if bond "b" is a double bond, R$^{13}$ is —C(R$^{33}$)=; or
  (3) if bond "b" is nil, R13 is hydrogen, —SO$_3$H, —PO(OR$^{34}$)OH, —C(O)NHSO$_2$N(R$^{34}$)(R$^{35}$), —$OSO_3H$, —$CH(R^{35})COOH$, or —$OCH(R^{34})COOH$ (preferably —$SO_3H$ $C(O)NHSO_2$—$N(R^{34})(R^{35})$; where $R^{34}$ is hydrogen, alkyl, alkenyl, a carbocyclic ring, or a heterocyclic ring; and $R^{35}$ is hydrogen, alkyl, alkenyl, or —$NHR^{8a}$; or (preferably), if $R^{13}$ is —$C(O)NHSO_2N(R^{34})(R^{35})$, $R^{34}$ and $R^{35}$ may together comprise a heterocyclic ring including the nitrogen to which $R^{34}$ and $R^{35}$ are bonded; and (F)
- (2) if bond "a" or bond "b" is nil, then $R^{14}$ is nil and L is bonded directly to $R^{12}$ or $R^{13}$;
- (2) if bond "a" and "b" are single bonds, $R^{14}$ is —W—C'"=C($R^{8a}$)—$R^{37}$, or —W—C'"($R^{36}$)—$R^{37}$—; or
- (3) (preferably) if bond "a" is a single bond and bond "b" is a double bond, $R^{14}$ is —C($R^{8a}$)($R^{38}$)—W—C'"—$R^{37}$—; or (preferably) —W—C($R^{8a}$)($R^{38}$)—C'"—$R^{37}$—, or —W—C'"—$R^{37}$—; where
  - (a) W is O; S(O)s, where s is an integer from 0 to 2 (preferably 0); or C($R^{38}$), where $R^{38}$ is hydrogen, alkyl or alkoxy;
  - (b) $R^{36}$ hydrogen; alkyl; alkenyl; —COOH; or, if $R^{13}$ is -C*($R^{33}$), $R^{36}$ may be linked to C* to form a 3-membered carbocyclic ring;
  - (c) $R^{37}$ is nil, alkyl, alkenyl, a carbocyclic ring, or a heterocyclic ring; and
  - (d) C'" is directly bonded to $R^{13}$ to form a 5- or 6-membered ring.

and (III) L links Q to B; and L is L', —$X^2_t$—$R^{39}$—L', or —$X^3_t$—$R^{39}$—L', where L' is Q', —$X^2$—Q", —$X^3$—Q", or —$X^4_t$—C(=$Y^3_u$)—Z—Q" (preferably —$X^2$—Q", —$X^3$—Q", —$X^4_t$—C(=$Y^3_u$)—Z—Q");

- (1) t and u are, independently, 0 or 1;
- (2) $R^{39}$ is alkyl, alkenyl, heteroalkyl, heteroalkenyl, a carbocyclic ring, or a heterocyclic ring (preferably alkyl or alkenyl);
- (3) $X^2$ is oxygen, or S(O)$_v$, where v is an integer from 0 to 2 (preferably 0);
- (4) $X^3$ is nitrogen; N($R^{40}$); N+($R^{41}$)($R^{42}$); or $R^{43}$—N($R^{41}$); and is linked to $R^{14}$ by a single or double bond; or, if $R^{14}$ is nil, $X^3$ is linked to B by a single or double bond (preferably $X^3$ is nitrogen, N($R^{40}$) or N+($R^{41}$)($R^{42}$)); where
  - (a) $R^{40}$ is $R^{8a}$; —$OR^{8a}$; or —C(=O)$R^{8a}$; (preferably $R^{8a}$);
  - (b) $R^{41}$ and $R^{42}$ are, independently, hydrogen; alkyl; alkenyl; carbocyclic rings; heterocyclic rings; or, if $R^6$ is $R^{16}X$, then $R^{41}$ and $R^{42}$ together with Q", may comprise a heterocyclic ring as $R^{16}$;
  - (c) $R^{43}$ is N($R^{41}$), oxygen or sulfur;
- (5) X4 is oxygen, sulfur, $NR^{40}$, or $R^{43}$—$NR^{41}$ (preferably oxygen, sulfur or $NR^{40}$);
- (6) $Y^3$ is oxygen, sulfur, $NR^{40}$ or N+($R^{41}$)($R^{42}$);
- (7) $Y^4$ is oxygen or $NR^{41}$ (preferably oxygen);
- (8) Z is nil, oxygen, sulfur, nitrogen, $NR^{40}$, or N($R^{41}$)—$R^{43}$ (preferably oxygen, sulfur, nitrogen or $NR^{40}$);
- (9) Q" is said $R^6$ substituent of Q; and
- (10) Q" is Q"; or together with $X^2$, $X^3$, Z or Z', is said $R^6$ substituent of Q;

and pharmaceutically-acceptable salts and biohydrolyzable esters thereof, and hydrates thereof.

Preferred lactam-containing moieties include cephems, isocephems, isooxacephems, oxacephems, carbacephems, penicillins, penems, carbapenems, and monocyclic beta-lactams. Particularly preferred are cephems, penems, carbapenems and monocyclic beta-lactams.

$R^{10}$, in formula (II), is any radical that may be substituted at the active stereoisomeric position of the carbon adjacent to the lactam carbonyl of an antimicrobially-active lactam. (As used herein, the term "antimicrobially-active lactam" refers to a lactam-containing compound, without a quinolonyl substituent moiety, which has antimicrobial activity.) This "active" position is beta (i.e., 7-beta) for cephems, oxacephems and carbacephems (for example). The active position is alpha for penems, carbapenems, clavems and clavams. Appropriate $R^{10}$ groups will be apparent to one of ordinary skill in the art.

Procedures for preparing quinolones and quinolone intermediates useful in the methods of this invention are described in the following references, all incorporated by reference herein (including articles listed within these references): 21 *Progress in Drug Research*, 9–104 (1977); 31 *J. Med. Chem.*, 503–506 (1988); 32 *J. Med. Chem.*, 1313–1318 (1989); 1987 *Liebigs Ann. Chem.*, 871–879 (1987); 14 Drugs Exptl. Clin. Res., 379–383 (1988); 31 *J. Med. Chem.*, 983–991 (1988); 32 *J. Med. Chem.*, 537–542 (1989); 78 *J. Pharm. Sci.*, 585–588 (1989); 26 *J. Het. Chem.*, (1989); 24 *J. Het. Chem.*, 181–185 (1987); U.S. Pat. No. 4,599,334, 35 *Chem. Pharm. Bull.*, 2281–2285 (1987); 29 *J. Med. Chem.*, 2363–2369 (1986); 31 *J. Med. Chem.*, 991–1001 (1988); 25 *J. Het. Chem.*, 479–485 (1988); European Patent Publication 266,576; European Patent Publication 251,308, 36 *Chem. Pharm. Bull.*, 1223–1228 (1988); European Patent Publication 227,088; European Patent Publication 227,039; European Patent Publication 228,661; 31 *J. Med. Chem.*, 1586–1590 (1988); 31 *J. Med. Chem.*, 1598–1611 (1988); 23 *J. Med. Chem.*, 1358–1363 (1980); *Quinolone Antimicrobial Agents*, 2d edition (D. Hooper and J. Wolfson, editors, 1993); J. V. Heck 24 *Ann. Rep Med. Chem.* 101 (R. C. Allen, editor, 1989); M. J. Suto, et al., 27 *Ann. Rep. Med. Chem.* 119 (1992); M. L. Hammond, 28 *Ann. Rep. Med. Chem.* 119 (1993); European Patent Publication 451,764 (1991); 25(2) *J. Heterocycl. Chem.* 479–85 (1988); U.S. patent application Ser. No. 4,719,302; European Patent Publication 216,345 (1987); 36 (18) *J. Med. Chem.* 2621-26 (1993); 3 *Mendeleev Commun.* 99–100 (1993); 36 (21) *J. Med. Chem.* 3148–53 (1993); 29(5) *J. Heterocycl. Chem.* 1117–23 (1992); 4 *Mendeleev Commun.* 151–53 (1992); 35(25) *J. Med. Chem.* 4767 (1992); 57 *J. Org. Chem.* 6991–95 (1992); 35(25) *J. Med. Chem.* 4727–38 (1992); World Patent Publication 92/06099 (1992); European Patent Publication 465,716 (1992); European Patent Publication 472,826 (1992); 35(1) *J. Med. Chem.* 94–99 (1992); World Patent Publication 91/07412 (1991); 16(5) *Drugs Exp. Clin. Res.* 215–24 (1990); European Patent Publication 393,538 (1990); European Patent Publication 387,877 (1990); 27(3) *J. Heteroeycl. Chem.* 587–89 (1990); 33(7) *J. Med. Chem.* 2012–15 (1990); World Patent Publication 89/12055 (1989); European Patent Publication 315, 827 (1989); European Patent Publication 315,828 (1989); European Patent Publication 312,794 (1989); 25(6) *J. Heterocycl. Chem.* 1769–72 (1988); 24(6) *J. Heterocycl. Chem.* 1537–39 (1987); German Patent Publication 3721745 (1988); European Patent Publication 251,308 (1988); Great Britain Patent Publication 2190376 (1987); U.S. patent application Ser. No. 4,659,734 (1987); 29(8) *J. Med. Chem.* 1531–34 (1986); U.S. patent application Ser. No. 4,550,104 (1985); European Patent Publication 58,392 (1982); 36(7) *J. Med. Chem.* 801–10 (1993); 33(26 *Tetrahedron Lett.* 3733–36 (1992); European Patent Publication 451,764 (1991); European Patent Publication 424,802 (1991); 16(5)

*Drugs Exp. Clin. Res.* 215–24 (1990); European Patent Publication 401,036 (1990); 27(5) *J. Heterocycl. Chem.* 1191–95 (1990); 27(4) *J. Heterocycl. Chem.* 839–43 (1990); 26(6) *J. Heterocycl. Chem.* 1675–81 (1989); 14(6) *Drugs Exp. Clin. Res.* 379–83 (1988); European Patent Publication 228,661 (1987); European Patent Publication 227,039 (1987); European Patent Publication 227,088 (1987); and German Patent Publication 2337474 (1975).

In general, 5-(N-heterosubstituted amino) quinolones of Formulas (I) and (II) can be prepared by the following procedure:

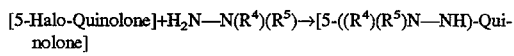

[5-Halo-Quinolone]+H$_2$N—N(R$^4$)(R$^5$)→[5-((R$^4$)(R$^5$)N—NH)-Quinolone]

where R$^4$ and R$^5$ are previously defined and [5-Halo-Quinolone] is an appropriately protected 5-halogen substituted quinolone where the halogen is preferably chloro or fluoro (preferably fluoro). The reaction sequence can be envisioned as a nucleophilic aromatic displacement of the quinolone 5-halogen substituted by (R$^4$)(R$^5$)N—NH$_2$ to form the 5-(N-heterosubstituted amino)quinolones.

Alternatively, 5-(N-heterosubstituted amino)quinolones of the present invention can be prepared by the following procedure:

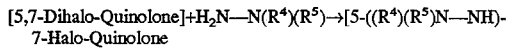

[5,7-Dihalo-Quinolone]+H$_2$N—N(R$^4$)(R$^5$)→[5-((R$^4$)(R$^5$)N—NH)-7-Halo-Quinolone where R$^4$ and R$^5$ are previously defined and [5,7-Dihalo-Quinolone] is an appropriately protected 5- and 7- halogen substituted quinolone where the halogen at positions 5 and 7 is independently a chloro or fluoro (preferably fluoro). The reaction sequence can be envisioned as a selective nucleophilic aromatic displacement of the quinolone 5-halogen substituent by (R$^4$)(R$^5$)N—NH$_2$ to form the 5-(N-heterosubstituted amino)quinolones. The reaction can preferably be carried out in a nonpolar aprotic solvent, preferably benzene, toluene, xylene, etc., at an elevated temperature, preferably 50° C. to reflux.

As another alternative, the 5-hydrazino quinolones of this invention can be prepared according to the following general reaction sequence:

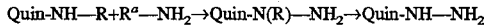

Quin-NH—R+R$^a$—NH$_2$→Quin-N(R)—NH$_2$→Quin-NH—NH$_2$ where "Quin-NH—R" is an appropriately protected 5-amino-substituted quinolone moiety, "R" is hydrogen or an acyl group (such as trifluoroacetyl, preferably) and "R$^a$—NH$_2$" is an electrophilic aminating reagent (such as O-2,4-dinitrophenyl hydroxylamine or hydroxylamine-O-sulfonic acid, preferably). The reaction can be envisioned as an electrophilic amination of the anion Quin-N($^-$)—R (formed from reaction of Quin-NH—R with a basic deprotonating agent, such as sodium hydride) to give a 5-hydrazino substituted quinolone, Quin-N(R)—NH—R. In the case where R=acyl, the quinolone is subsequently deprotected (for example, with heating in methanol/aqueous potassium carbonate where R=trifluoroacetyl) to give the unsubstituted 5-hydrazino product Quin-NHNH$_2$.

Procedures useful in the preparation and reaction of electrophilic aminating reagents as well as alkylation of anionic nitrogen including 5-aminoquinolones are contained in the following references: 4 *J. Het. Chem.* 413 (1967); 92 *Chem. Ber.* 2521 (1959); 43 *Org. Synth.* 1 (1963); 16 Tet. Lett., 1909 (1968); 31 *J. Med. Chem.* 503 (1988).

Compositions

The compositions of this invention comprise:

(a) a safe and effective amount of a 5-(N-heterosubstituted amino) quinolone; and (b) a pharmaceutically-acceptable carrier.

A "safe and effective amount" of a 5-(N-heterosubstituted amino) quinolone is an amount that is effective, to inhibit microbial growth at the site of an infection to be treated in a human or lower animal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the 5-(N-heterosubstituted amino) quinolone therein, and the dosage regimen desired for the composition.

The compositions of this invention are preferably provided in unit dosage form. As used herein, a "unit dosage form" is a composition of this invention containing an amount of a 5-(N-heterosubstituted amino) quinolone that is suitable for administration to a human or lower animal subject, in a single dose, according to good medical practice. These compositions preferably contain from about 30 mg to about 20,000 mg, more preferably from about 50 mg (milligrams) to about 7000 mg, more preferably from about 500 mg to about 3500 mg, of a 5-(N-heterosubstituted amino) quinolone.

The compositions of this invention may be in any of a variety of forms, suitable (for example) for oral, rectal, topical or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the antimicrobial activity of the 5-(N-heterosubstituted amino) quinolone. The amount of carrier employed in conjunction with the 5-(N-heterosubstituted amino) quinolone is sufficient to provide a practical quantity of material for administration per unit dose of the 5-(N-heterosubstituted amino) quinolones. Techniques and compositions for making dosage forms useful in the methods of this invention are described in the following references, all incorporated by reference herein: 7 *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight by the total composition.

Various oral dosage forms can be used, including such solid forms as tablets, capsules, granules and bulk powders. These oral forms comprise a safe and effective amount, usually at least about 5%, and preferably from about 25% to about 50%, of the 5-(N-heterosubstituted amino) quinolone. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from noneffervescent granules, and effervescent preparations reconstituted from effervescent granules, containing suitable solvents, preservatives, emulsifying agents, suspending agents, diluents, sweeteners, melting agents, coloring agents and flavoring agents. Preferred carriers for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions preferably comprise a safe and effective amount, usually at least about 0.1%, and preferably from about 1% to about 5%, of the 5-(N-heterosubstituted amino) quinolone. Suitable carriers for topical administration preferably remain in place on the skin as a continuous film, and resist being removed by perspiration or immersion in water. Generally, the carrier is organic in nature and capable of having dispersed or dissolved therein the 5-(N-heterosubstituted amino) quinolone. The carrier may include pharmaceutically-acceptable emollients, emulsifiers, thickening agents, and solvents.

Methods of Administration

This invention also provides methods of treating or preventing an infectious disorder in a human or other animal subject, by administering a safe and effective amount of a 5-(N-heterosubstituted amino) quinolone to said subject. As used herein, an "infectious disorder" is any disorder characterized by the presence of a microbial infection. Preferred methods of this invention are for the treatment of bacterial infections. Such infectious disorders include (for example) central nervous system infections, external ear infections, infections of the middle ear (such as acute otitis media), infections of the cranial sinuses, eye infections, infections of the oral cavity (such as infections of the teeth, gums and mucosa), upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients (such as patients receiving cancer chemotherapy, or organ transplant patients).

The 5-(N-heterosubstituted amino) quinolones and compositions of this invention can be administered topically or systemically. Systemic application includes any method of introducing the 5-(N-heterosubstituted amino) quinolone into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, are mutually dependent. The dosage and treatment regimen will also depend upon such factors as the specific 5-(N-heterosubstituted amino) quinolone used, the resistance pattern of the infecting organism to the 5-(N-heterosubstituted amino) quinolone used, the ability of the 5-(N-heterosubstituted amino) quinolone to reach minimum inhibitory concentrations at the site of the infection, the nature and extent of other infections (if any), the personal attributes of the subject (such as weight), compliance with the treatment regimen, and the presence and severity of any side effects of the treatment.

Typically, for a human adult (weighing approximately 70 kilograms), from about 75 mg to about 30,000 mg, more preferably from about 100 mg to about 20,000 mg, more preferably from about 500 mg to about 3500 mg, of 5-(N-heterosubstituted amino) quinolone are administered per day. Treatment regimens preferably extend from about 1 to about 56 days, preferably from about 7 to about 28 days, in duration. Prophylactic regimens (such as avoidance of opportunistic infections in immunocompromised patients) may extend 6 months, or longer, according to good medical practice.

A preferred method of parenteral administration is through intramuscular injection. As is known and practiced in the art, all formulations for parenteral administration must be sterile. For mammals, especially humans, (assuming an approximate body weight of 70 kilograms) individual doses of from about 100 mg to about 7000 mg, preferably from about 500 mg to about 3500 mg, are acceptable.

A preferred method of systemic administration is oral. Individual doses of from about 100 mg to about 2500 mg, preferably from about 250 mg to about 1000 mg are preferred.

Topical administration can be used to deliver the 5-(N-heterosubstituted amino) quinolone systemically, or to treat a local infection. The amounts of 5-(N-heterosubstituted amino) quinolone to be topically administered depends upon such factors as skin sensitivity, type and location of the tissue to be treated, the composition and carrier (if any) to be administered, the particular 5-(N-heterosubstituted amino) quinolone to be administered, as well as the particular disorder to be treated and the extent to which systemic (as distinguished from local) effects are desired.

The following non-limiting examples illustrate the compounds, compositions, processes, and uses of the present invention.

EXAMPLE 1

Synthesis of (S)-7-(3-Aminopyrrolidinyl)-1-cyclopropyl-6,8-difluoro-5-hydrazino-1,4-dihydro-4-oxo-3-quinolinecarboxylic Acid Dihydrochloride

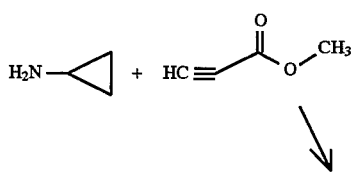

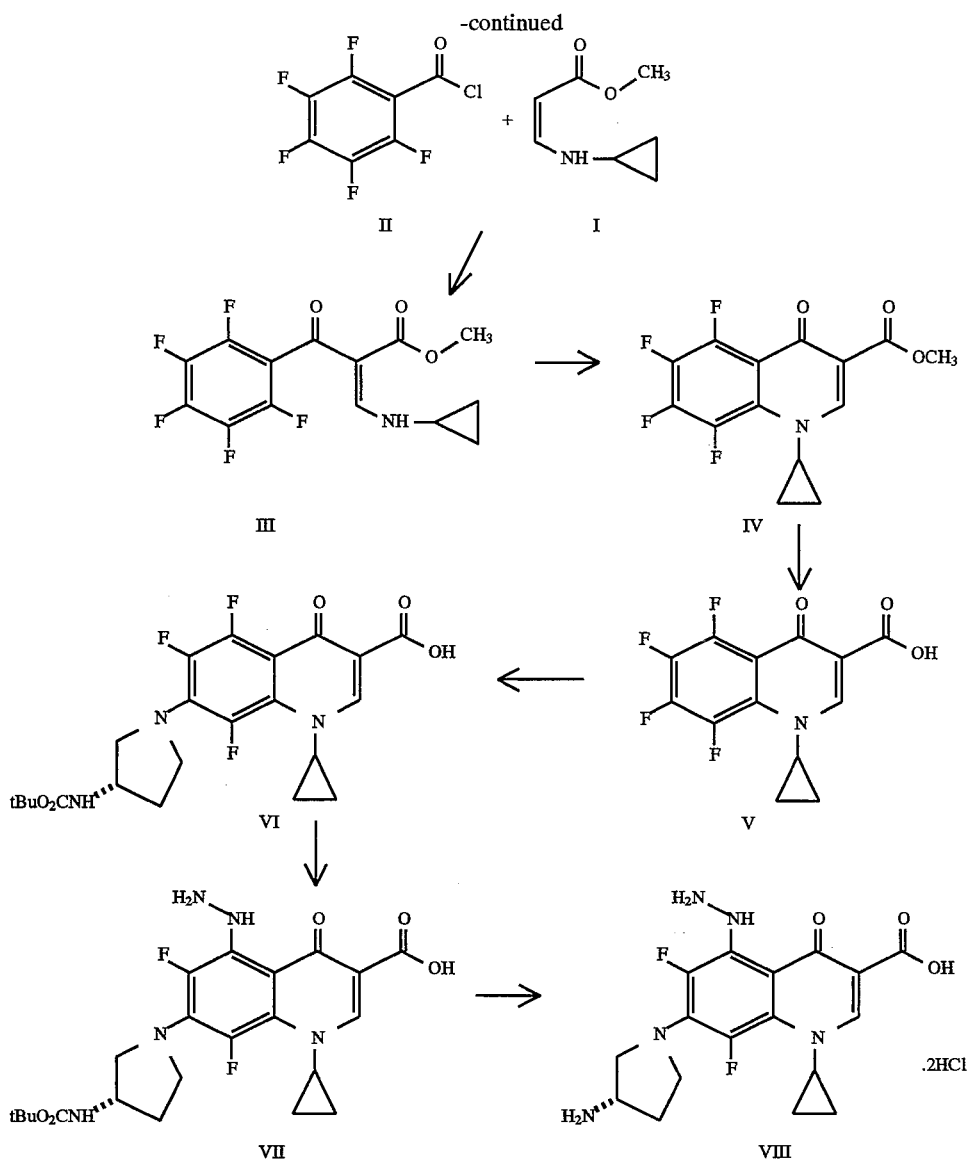

A mixture of methyl propiolate (983 g, 11.7 mole) and 500 ml of tetrahydrofuran is cooled to 5° C. and cyclopropylamine (667 g, 11.7 mole) dissolved in 1000 ml of tetrahydrofuran is added over approximately one hour from an addition funnel at a rate to keep the temperature at 3°–7° C. The mixture is stirred for an additional hour at 5° C. and the ice bath is removed. The reaction is stirred for approximately one hour at 20°–25° C. at room temperature for 3 hours and is allowed to stand for about 2.5 days at room temperature. The solvent is removed under reduced pressure and the residue is vacuum distilled to give 1.

A solution of approximately 207 g of pentafluorobenzoyl chloride (compound 2) (0.90 mole) and 250 ml of dioxane is cooled to 15°–20° C. with an ice water bath and a solution of approximately 126 g of 1 and 90.9 g of triethylamine (0.90 mole) in 300 ml of dioxane is added dropwise over 5.5 hours. The addition funnel is rinsed with an additional 50 ml of dioxane and the reaction is stirred at 20° C. overnight. The mixture is then vacuum filtered and the precipitate is washed twice with 100 ml portions of dioxane. The filtrate is vacuum stripped at 25° C. and 1000 ml of hexane is added to the residue. More precipitate is collected and added to the first batch. The combined product is then resuspended in 1500 ml of hexane, stirred briefly, filtered and vacuum dried to give compound 3.

In a 5 L three-necked round-bottom flask equipped with thermometer, argon inlet, mechanical stirrer, and an addition funnel is placed approximately 14.9 g (0.621 mole) NaH (from hexane-washed NaH/mineral oil) and 1000 ml of dimethylformamide. This mixture is cooled to 15°–20° C. and approximately 181.5 g of compound 3 (0.542 mole) dissolved in 2 L of dimethylformamide is added dropwise over 3.5 hours while keeping the temperature at 15°–20° C. Stirring is continued for 1.5 hours at this temperature and then the mixture is further cooled to 10° C. and 500 ml of ice and 1 L of water is added. The mixture is neutralized to pH 7 with approximately 5 ml of acetic acid and is extracted three times with chloroform. The dried chloroform extracts are evaporated to give a slurry which is triturated with 400 ml of boiling ethanol. The resulting solids are filtered at room temperature. An additional wash with 100 ml of cold ethanol followed by vacuum drying gives compound 4.

A mixture of compound 4 (22 g, 0.070 mole) and 2N $H_2SO_4$ (600 ml) is stirred at 100° C. for 20 hours and allowed to cool to room temperature. The product 5 is collected by filtration, washing with water.

To a mixture of 5 (18 g, 0.060 mole) (3S)-t-butoxy-carbonylaminopyrrolidine (12 g, 0.066 mole) and dimethylformamide (130 ml) at 54° C. is added dropwise triethylamine (17 ml, 0.12 mole). The mixture is stirred at 54° C. for four hours. Acetonitrile (120 ml) is added and the mixture is heated to 75° C. and then allowed to cool to room temperature. The mixture is cooled to 15° C. and the solid is collected by filtration, washing with acetonitrile (2×60 ml). The solid is stirred in acetonitrile (180 ml) for 10 minutes and the product 6 is collected by filtration, washing with acetonitrile (2×60 ml).

A mixture of compound 6 (4.0 g, 0.0086 mole), acetonitrile (120 ml) and hydrazine monohydrate (4.0 ml, 0.082 mole) is refluxed for 2.5 hours with a solution forming. The solution is diluted with acetonitrile (100 ml) and stirred for 2 hours at room temperature. The precipitate is collected by filtration and heated in acetonitrile (150 ml). Some undissolved material is removed by filtration and the filtrate is stored at room temperature overnight. The product 7 is collected by filtration washing with acetonitrile.

To a mixture of 7 (4.0 g, 0.0083 mole) and methylene chloride (85 ml) at room temperature is added saturated ethanol/HCl (55 ml) slowly with stirring. The mixture is stirred at room temperature for 4.5 hours and the solid is collected by filtration. This material is heated in $CHCl_3$ (100 ml) and methanol (10 ml) is added. The mixture is cooled to room temperature and the final product (8) is collected by filtration, washing with $CHCl_3$.

EXAMPLE 2

Synthesis of (3S)-7-(3-amino-1-pyrrolidinyl)-1-(2,4,difluorophenyl)-6,8-difluoro-5-hydrazino-1,4-dihydro-4-oxo-3-quinolinecarboxylic acid dihydrochloride

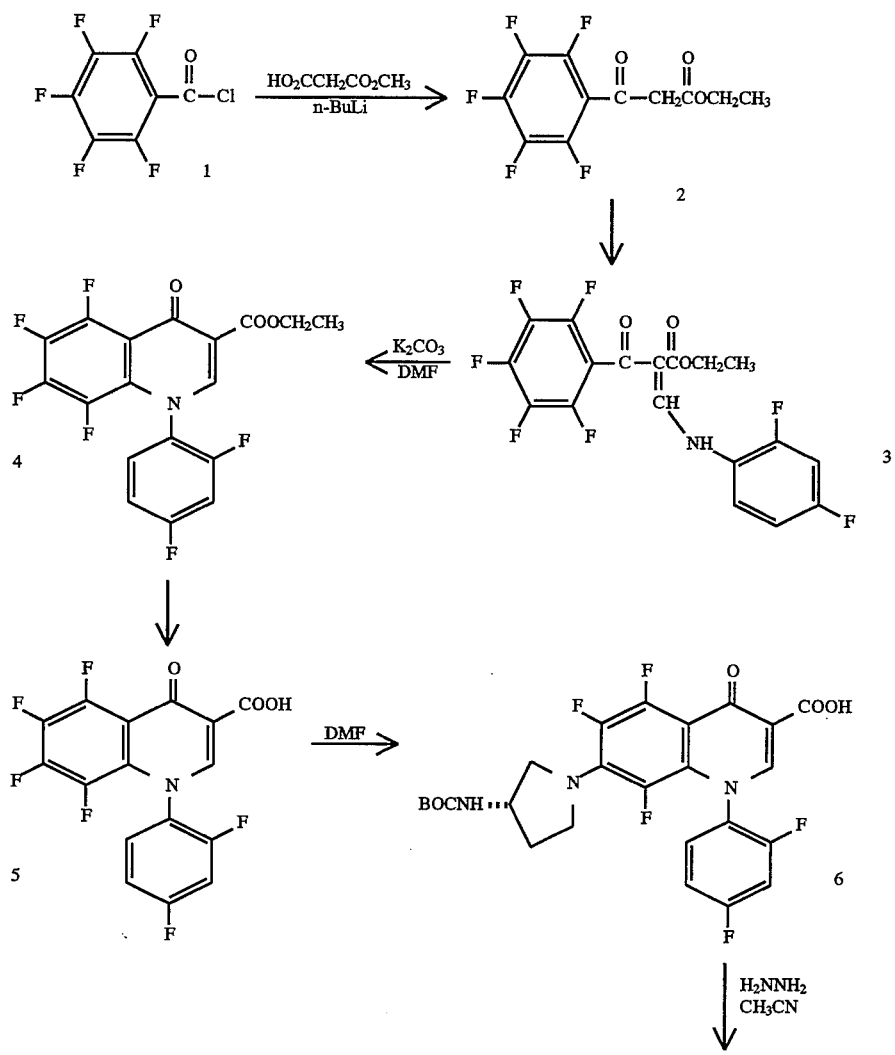

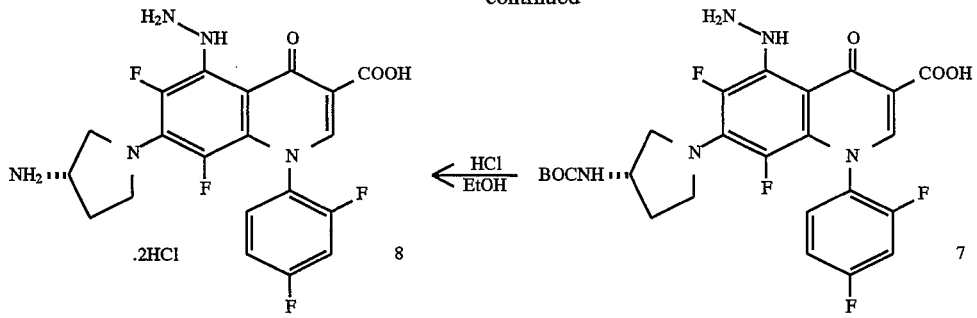

Monoethyl hydrogenmalonate (13.2 g, 0.10 mol) is dissolved in tetrahydrofuran (260 ml) and cooled to −65° C. Then 2M n-butyl lithium (100 ml, 0.20 mol) is added dropwise to maintain a temperature below −50° C. The reaction is warmed to −5° C. and recooled to −65° C. Pentafluorobenzoyl chloride 1 (7.20 ml, 0.05 mol) is dissolved in tetrahydrofuran (32 ml) and is added dropwise to keep the temperature below −50° C. After the addition, the reaction was warmed to −35° C. and stirred for 1 hr. Aqueous HCl (13%, 316 ml) is added to the solution and stirred for 30 min. The mixture is extracted with $CH_2Cl_2$ and washed with aqueous $NaHCO_3$ followed by water. The organic layer is dried with $Na_2SO_4$ and concentrated to give the product 2, which exists as a mixture of keto-enol tautomers in solution.

Pentafluorobenzoyl acetic acid ethyl ester 2 (10 g, 0.035 mol) is added to acetic anhydride (8.5 ml, 0.09 mol) and triethylorthoformate (10 ml, 0.06 mol). The reaction is heated to 110° C. for 2.25 hrs. The reaction is concentrated. The product is dissolved in ethanol (250 ml) and cooled to 0° C. Then 2,4-difluoroaniline (4.7 ml, 0.046 mol) is slowly added and the ice bath is removed. The reaction is stirred overnight and concentrated to dryness under reduced pressure. The residue is triturated in petroleum ether and the product is collected by filtration to give 3 as a mixture of cis-trans isomers.

The vinylogous amide 3 (9.43 g, 0.022 mol) is dissolved in dimethylformamide (57.0 ml) and $K_2CO_3$ (9.46 g, 0.068 mol) is added. The reaction is stirred overnight and then concentrated. Methylene chloride is added and the solution is washed with water. The organic phase is dried over $Na_2SO_4$, concentrated, and vacuum dried to give the quinolone 4.

The ester 4 (8.49 g, 0.021 mol) is placed in a solution of 8:6:1 acetic acid/water/$H_2SO_4$ (309 ml) and is heated to 100° C. until the reaction is complete. The solution is poured into ice water, and the precipitate is filtered. The product is recrystallized by dissolving in $CH_2Cl_2$ and precipitating out with hexane. The solid is collected to afford the acid 5. The filtrate is concentrated and the residue is purified as previously from $CH_2Cl_2$ to give a second crop.

The quinolone 5 (10 g, 0.027 mol) is dissolved in dimethylformamide (60 ml) and (3S)-t-butoxycarbonylaminopyrrolidine (6.0 g, 0.032 mol) was added. The reaction is heated to 55° C. and triethylamine (7.5 ml, 0.054 mol) is added over 20 min. The reaction is complete in 45 min. as determined by TLC and the heat is removed. The product precipitates out of solution and is filtered. The solid is rinsed with ether. The product is dissolved in hot EtOAc and is precipitated out by the addition of hexanes. The solid is filtered and vacuum dried to afford 6.

A mixture of quinolone 6 (2.0 g, 0.0037 mol), acetonitrile (60 ml) and hydrazine (0.46 ml, 0.0095 mole) is refluxed for 1.6 hrs. and cooled to room temperature. The product is collected by filtration and is recrystallized from acetonitrile to give 7.

A mixture of 7 (0.20 g, 0.00036 mol) and saturated HCl/EtOH (4 ml) is stirred at room temperature for one hr. and another 4 ml of HCl/EtOH is added. The reaction is stirred for an additional 3 hrs. and the solid is collected by filtration. The solid is triturated in $CH_2Cl_2$ and is collected by filtration. The product is recrystallized from acetonitrile/$H_2O$ to give final product.

EXAMPLE 3

Synthesis of 1-cyclopropyl-6,8-difluoro-5-hydrazino-1,4-dihydro-4-oxo-7-piperazinyl-3-quinolinecarboxylic acid dihydrochloride.

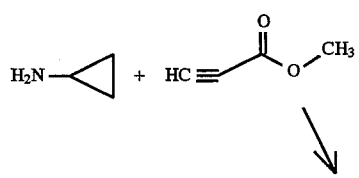

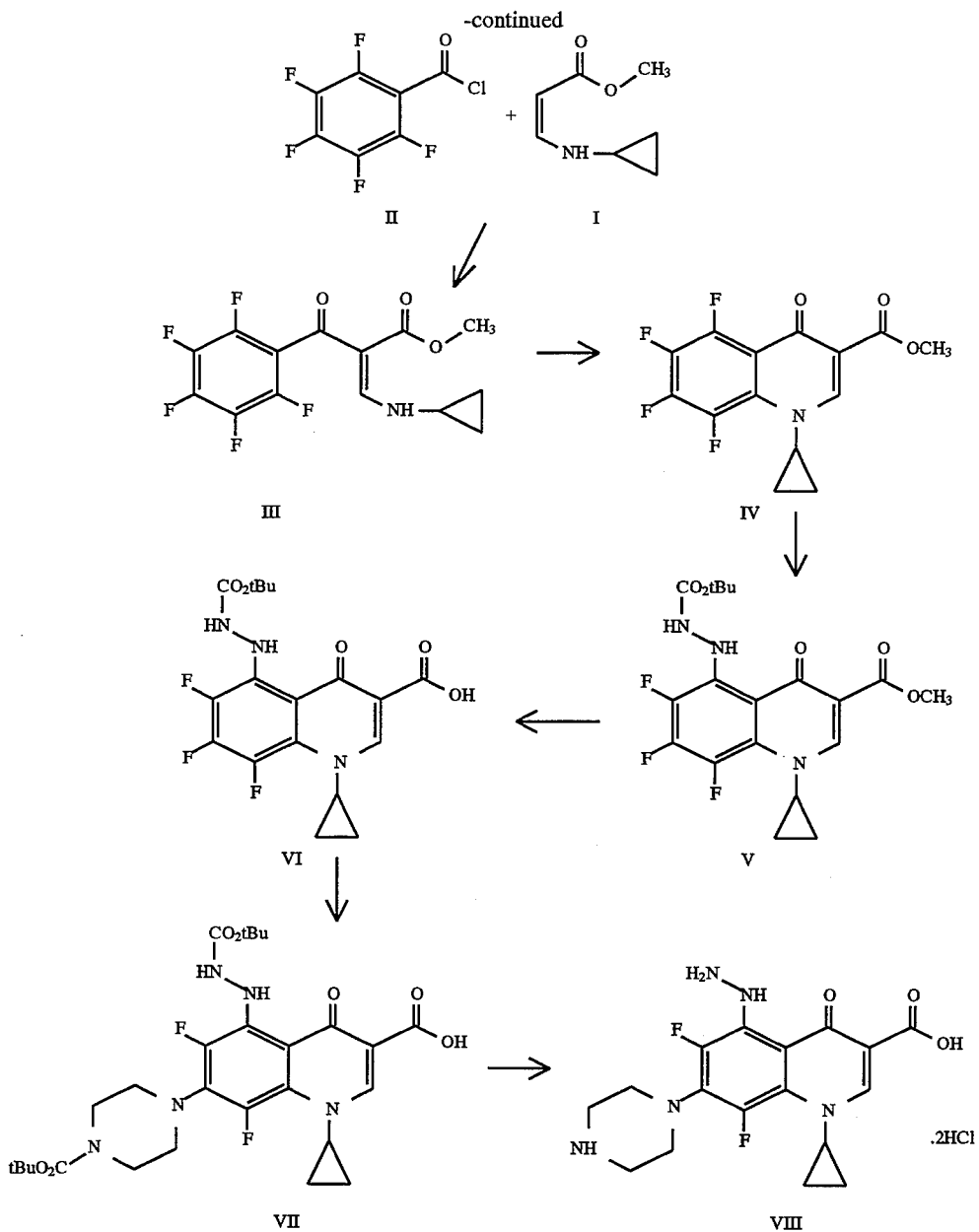

A mixture of methyl propiolate (983 g, 11.7 mole) and 500 ml of tetrahydrofuran is cooled to 5° C. and cyclopropylamine (667 g, 11.7 mole) dissolved in 1000 ml of tetrahydrofuran is added over approximately one hour from an addition funnel at a rate to keep the temperature at 3°–7° C. The mixture is stirred for an additional hour at 5° C. and the ice bath is removed. The reaction is stirred for approximately one hour at 20°–25° C. at room temperature for 3 hours and is allowed to stand for about 2.5 days at room temperature. The solvent is removed under reduced pressure and the residue is vacuum distilled to give I.

A solution of approximately 207 g of pentafluorobenzoyl chloride II (0.90 mole) and 250 ml of dioxane is cooled to 15°–20° C. with an ice water bath and a solution of approximately 126 g of I and 90.9 g of triethylamine (0.90 mole) in 300 ml of dioxane is added dropwise over 5.5 hours. The addition funnel is rinsed with an additional 50 ml of dioxane and the reaction is stirred at 20° C. overnight. The mixture is then vacuum filtered and the precipitate is washed twice with 100 ml portions of dioxane. The filtrate is vacuum stripped at 25° C. and 1000 ml of hexane is added to the residue. More precipitate is collected and added to the first batch. The combined product is then resuspended in 1500 ml of hexane, stirred briefly, filtered and vacuum dried to give III.

In a 5 L three-necked round-bottom flask equipped with thermometer, argon inlet, mechanical stirrer, and an addition funnel is placed approximately 14.9 g (0.621 mole) NaH (from hexane-washed NaH/mineral oil) and 1000 ml of dimethylformamide. This mixture is cooled to 15–20° C. and approximately 181.5 g of III (0.542 mole) dissolved in 2 L of dimethylformamide is added dropwise over 3.5 hours while keeping the temperature at 15°–20° C. Stirring is continued for 1.5 hours at this temperature and then the mixture is further cooled to 10° C. and 500 ml of ice and 1 L of water is added. The mixture is neutralized to pH 7 with approximately 5 ml of acetic acid and is extracted three times with chloroform. The dried chloroform extracts are evaporated to give a slurry which is triturated with 400 ml of boiling ethanol. The resulting solids are filtered at room temperature. An additional wash with 100 ml of cold ethanol followed by vacuum drying gives IV.

A stirred mixture of 1-cyclopropyl-5,6,7,8-tetrafluoro-4-oxo-3-carboxylic acid, methyl ester (compound IV) (8.2 g), triethylamine (4 ml), t-butyl carbazate (3.8 g), and toluene is refluxed for approximately one hour and concentrated to dryness under reduced pressure. The residue is dissolved in $CH_2Cl_2$ (200 ml) and washed with water (200 ml) and brine (200 ml). The organic phase is dried over $Na_2SO_4$, filtered and the filtrate is concentrated to dryness under reduced pressure. The residue is purified by flash chromatography (silica gel) with 5% $MeOH/CH_2Cl_2$ to give the desired C-5 substituted product V.

A mixture of approximately 3.5 g of V, tetrahydrofuran (THF) (30 ml) and 17 ml of 1N NaOH is heated at 80° C. for approximately 1.5 hours. The reaction is cooled in an ice bath and water (200 ml) is added, followed by the addition of glacial acetic acid (2.3 ml). The precipitate is filtered, washing with water and ether to give compound VI.

A mixture of approximately 2.6 g of VI, 1.3 g of 1-(t-butoxycarbonyl)piperazine, and pyridine (20 ml) is heated at 80° C. for approximately one hour and the reaction mixture is concentrated to dryness under reduced pressure. The residue is dissolved in $CH_2Cl_2$ (100 ml) and washed with water, 5% citric acid, water, and brine. The organic layer is dried over $Na_2SO_4$, filtered and the filtrate is concentrated to dryness. The residue is purified by flash chromatography (silica gel) with 5% $MeOH/CH_2Cl_2$ to afford compound of VII.

To a mixture of VII (2.3 g) and $CH_2Cl_2$ (40 ml) at room temperature is added slowly approximately 28 ml of saturated ethanol/HCl. The mixture is stirred at room temperature for approximately 4.5 hours and the product is collected by filtration. The solid is heated in $CHCl_3$ (50 ml) and methanol (10 ml) is added. The mixture is cooled to room temperature and the product is collected by filtration to give compound VIII.

EXAMPLE 4

Synthesis of 7-(3-Amino-1-pyrrolidinyl)-9-cyclopropyl-6,8-difluoro-5-hydrazino-isothiasolo[5,4-b]quinoline-3,4(2H, 9H)-dione Dihydrochloride

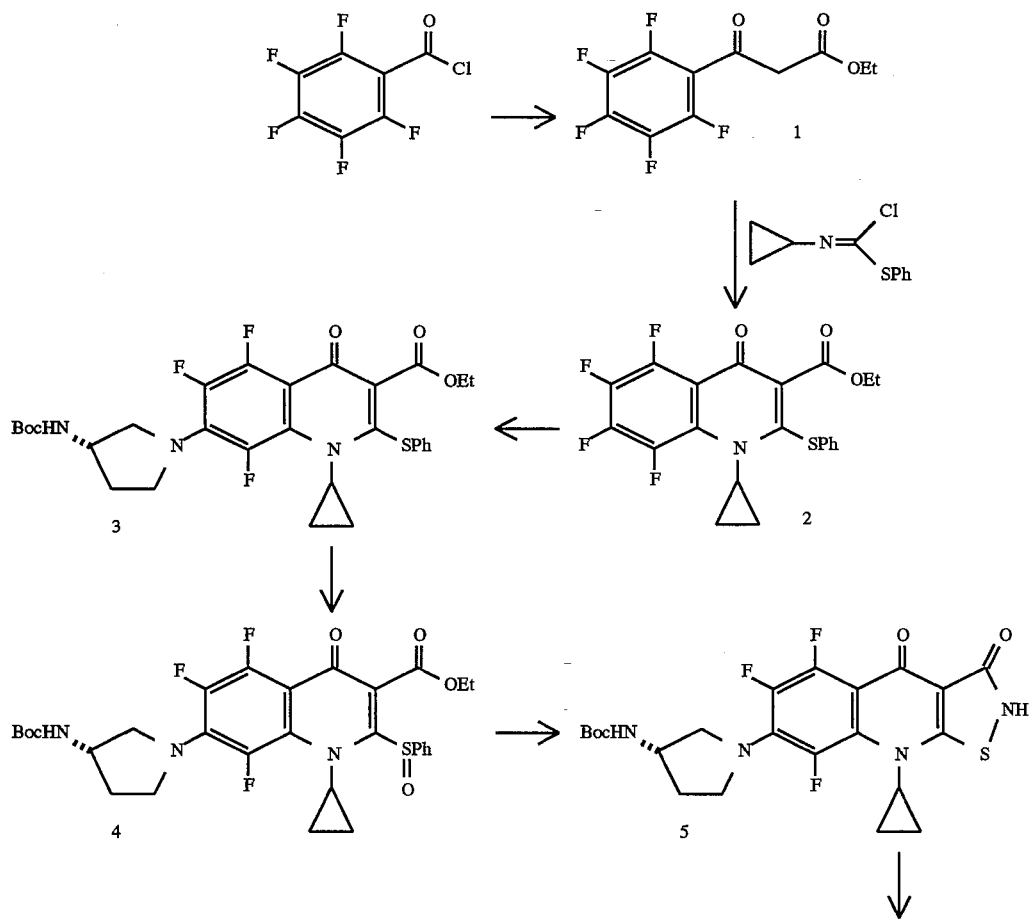

-continued

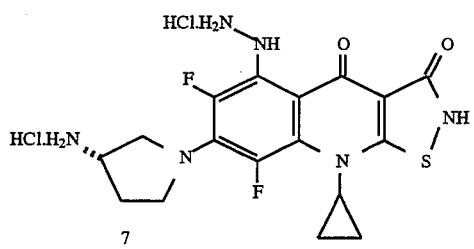 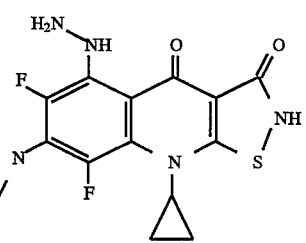

A 5 liter 3-neck round bottom flask is equipped with a low temperature thermometer and an addition funnel. It is placed under argon and ethyl hydrogen malonate (approximately 85 g) and 1.6 l of THF is added. It is cooled below −40° C., and n-butyllithium (approximately 800 ml) is added at a fast drop rate. After the addition is complete, the reaction is allowed to warm to approximately 0° C., before it is recooled to approximately −50° C. A solution of pentafluorobenzoyl chloride (approximately 63 g,) in 200 ml of THF is added dropwise, and the mixture is stirred overnight at room temperature. The reaction is poured into approximately 300 ml conc. HCl in 2 l of water, and is stirred for about 1 hour before extraction with ether. The organic layer is washed with saturated sodium bicarbonate solution, and is dried over sodium sulfate. Concentration in vacuo gives compound 1 as an oil, which can be further purified via vacuum distillation.

A solution of compound 1 (approximately 6.2 g) in 100 ml of toluene is placed under argon. Sodium hydride (approximately 0.97 g) is added at room temperature. After approximately one hour at room temperature, phenyl N-cyclopropyliminochlorothioformate (approximately 7.0 g, prepared according to J. Heterocyclic Chem. 27, 1990, 1191) is introduced, and the mixture is heated to approximately 55° C. After approximately 4 hours, the bath temperature is increased to approximately 125–130° C., and the reaction is allowed to stir overnight. The reaction is then cooled and is diluted with methylene chloride. The solution is washed with water, and the organics are dried over sodium sulfate. Concentration in vacuo gives a crude product, which can be chromatographed over silica gel to provide compound 2.

Compound 2 (approximately 0.25 g) and 3-(t-butoxycarbonylamino)pyrrolidine (approximately 0.42 g) are combined in 5 ml of anhydrous pyridine under argon at approximately 60° C. After approximately 7 hours, the mixture is concentrated and chromatographed on silica gel to yield compound 3.

Compound 3 (approximately 0.10 g) and mCPBA (65%, approximately 0.75 g) are combined in 15 ml methylene chloride, and the reaction is stirred at room temperature for 2 hours. Another 0.4 g of mCPBA is added, and the reaction is stirred an additional 30 minutes. The reaction is then diluted with methylene chloride, and is washed with dilute aqueous sodium bicarbonate, and dilute aqueous sodium bisulfite. The organics are dried over magnesium sulfate and concentrated to yield compound 4.

To a chilled (0°–5° C.) solution of compound 4 (approximately 0.50 g) in 20 ml THF under argon is added a solution of sodium hydrosulfide (approximately 0.09 gm) in 5 ml water, followed by a solution of approximately 0.15 g of sodium bicarbonate in 4 ml of water. After stirring for approximately one hour, additional sodium bicarbonate solution (approximately 0.6 g in 15 ml water) is added. The reaction is warmed to room temperature, and is stirred for approximately 3 hours before partitioning between pH 7 buffer and chloroform. The organics are dried over magnesium sulfate and concentrated in vacuo to provide a crude residue. Pure compound 5 is obtained by silica gel chromatography.

A mixture of the compound 5 (approximately 0.25 g) and hydrazine monohydrate (approximately 0.25 g) in 7 ml acetonitrile is refluxed under argon for approximately 3 hr. Compound 6 is precipitated from the cooled reaction mixture by further dilution with acetonitrile, and is collected by filtration. Purified compound 6 is obtained by repeated trituration.

Compound 6 (approximately 0.10 g) and 10 ml of methylene chloride are mixed at room temperature. Ethanol saturated with HCl (approximately 1.5 ml) is added with stirring. After 4.5 hours, the precipitated compound 7 is collected via filtration. It can be further purified by repeated trituration.

The following compounds can be made according to Example 4, with substantially similar results:

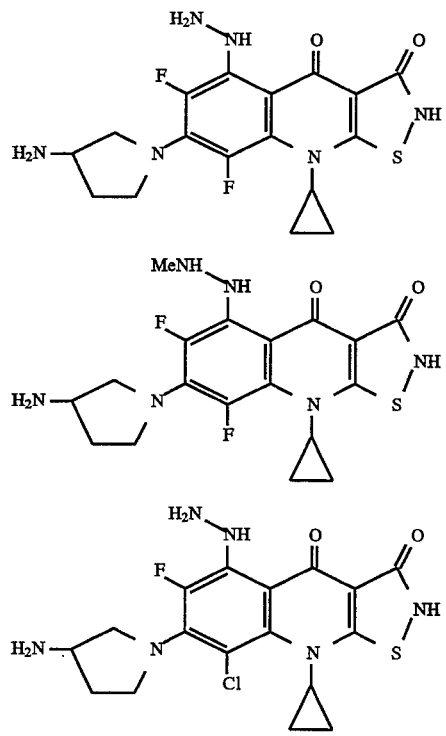

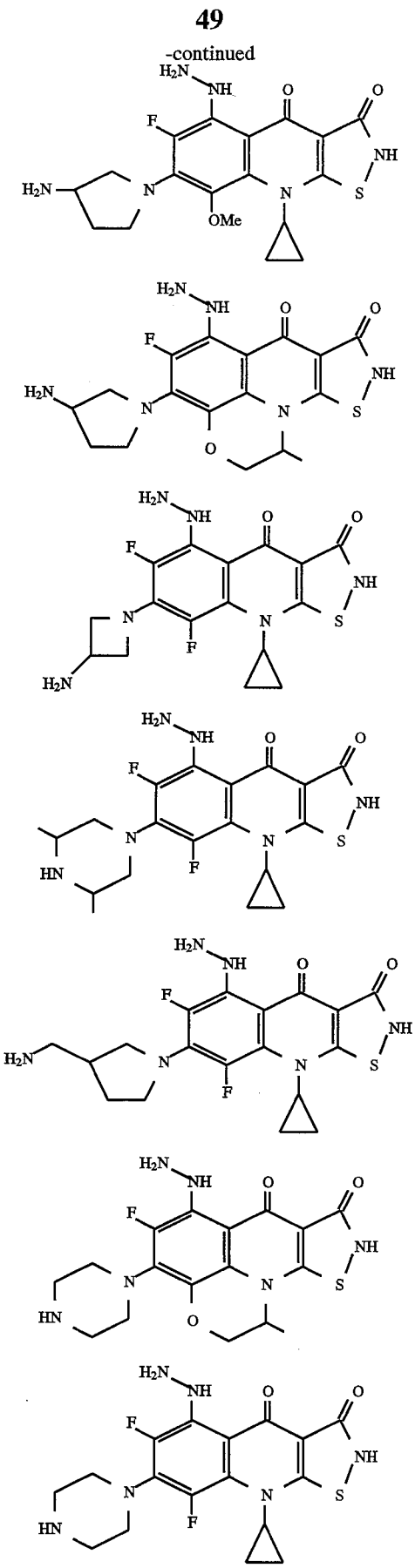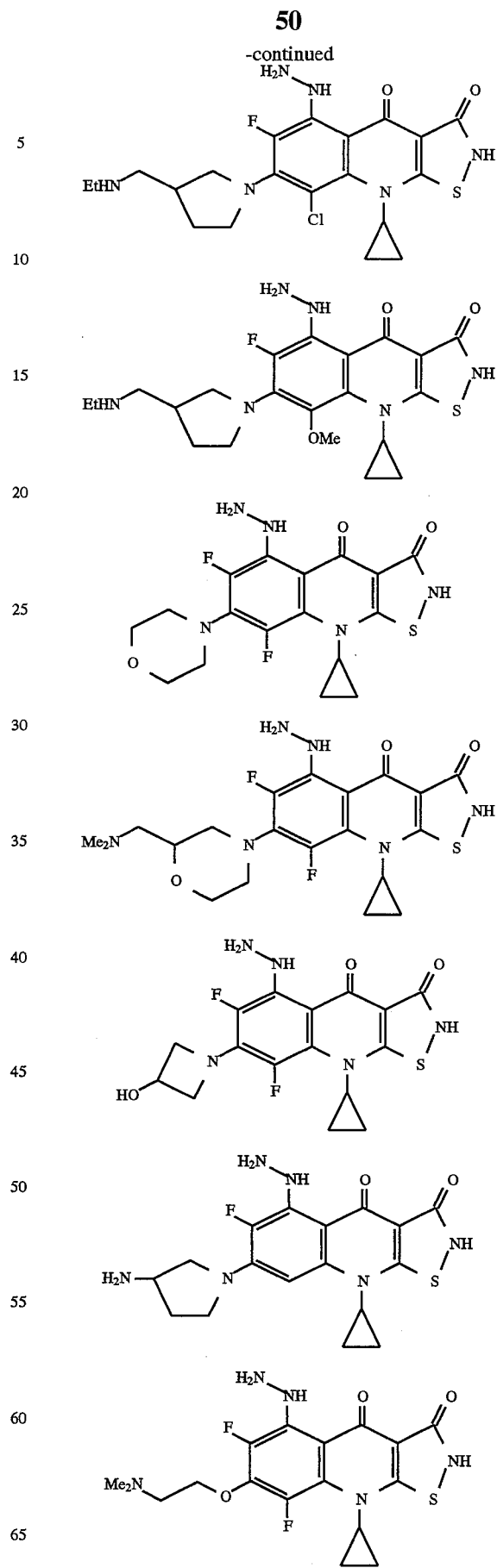

51
-continued
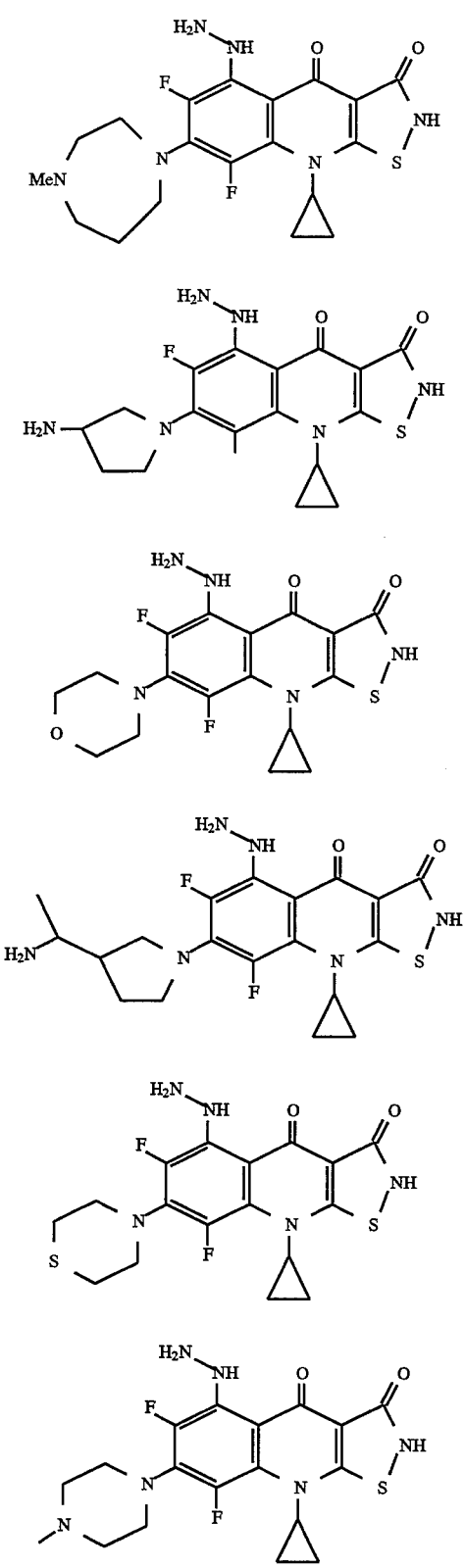
52
-continued
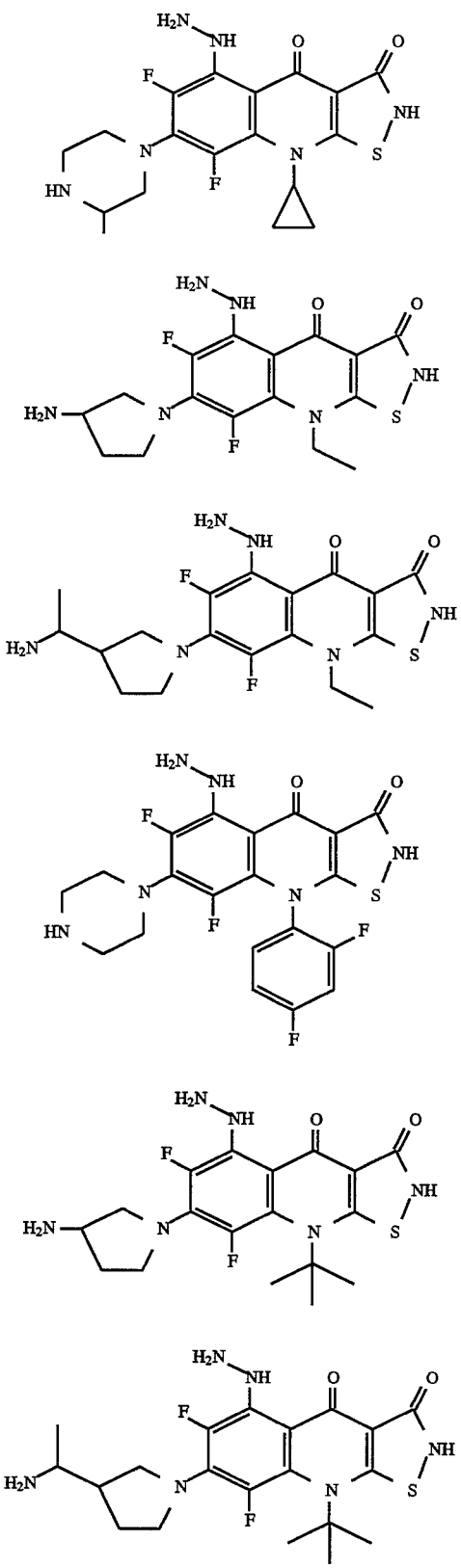

-continued
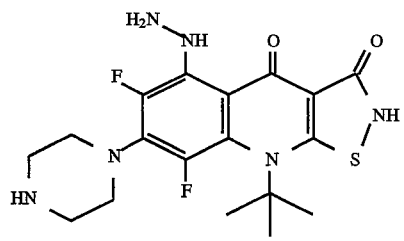
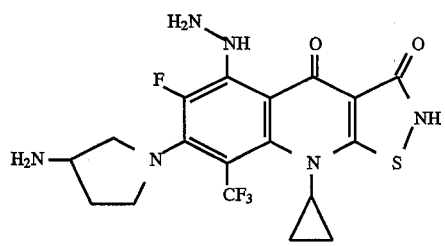
EXAMPLE 5
Synthesis of 7-(3-Amino-1-pyrrolidinyl)-6,8-difluoro-5-hydrozino-4-oxo-4H-1,3]thiazeto[3,2a]-quinoline-3-carboxylic Acid
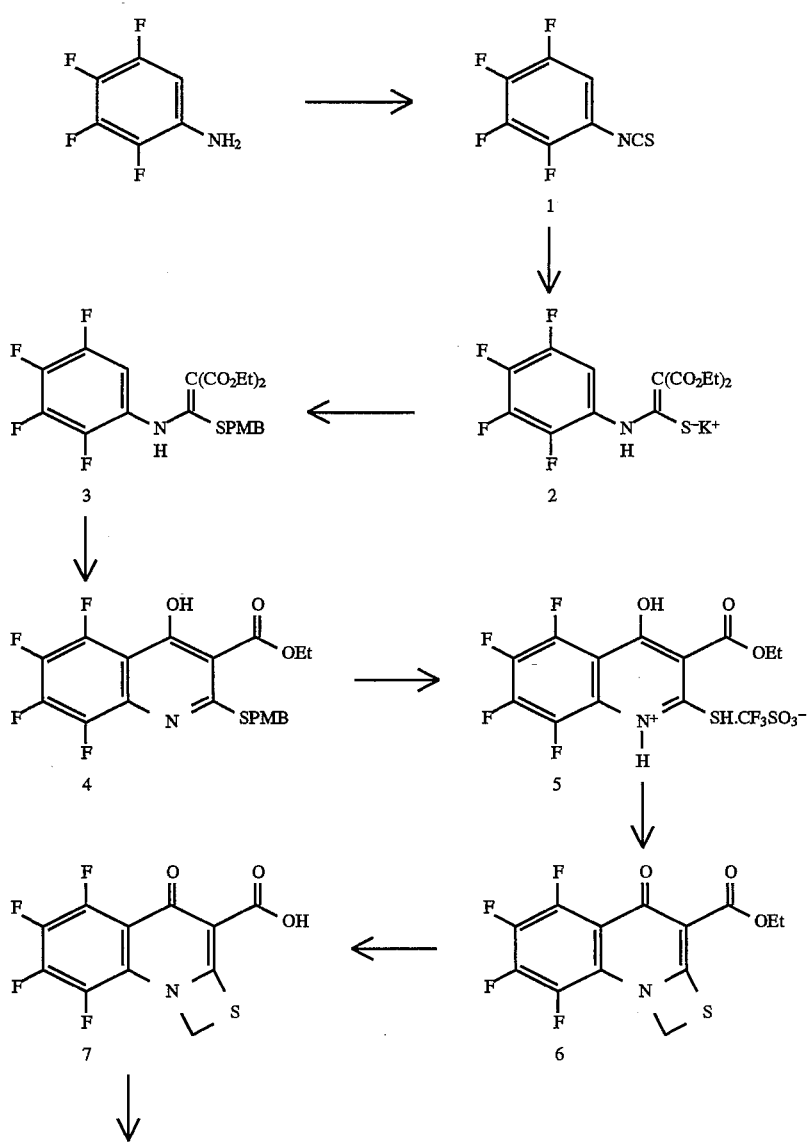

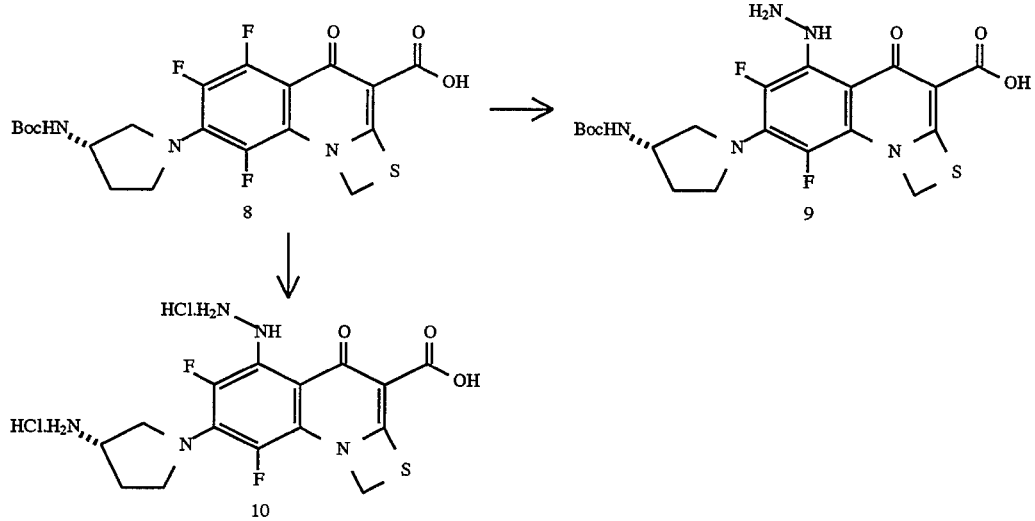

-continued

A suspension of approximately 16.5 ml thiophosgene and 30 ml water is cooled in an ice bath with vigorous stirring. Approximately 15.3 g of 2,3,4,5-tetrafloroaniline is added portionwise while maintaining the reaction temperature below 10° C. Then the ice bath is replaced with a cold water bath and stirring is continued for about 1 h. The reaction mixture is extracted with dichloromethane, and the organic extracts are dried over anhydrous $Na_2SO_4$, filtered and evaporated under reduced pressure to give compound 1.

To a slurry of approximately 5.4 g potassium hydroxide in 300 ml dioxane at approximately 10° C. is added a solution of approximately 15.5 g diethyl malonate in 40 ml dioxane dropwise. The reaction is stirred at approximately 10° C. for 4 h, then a solution of approximately 20.1 g compound 1 in 50 ml dioxane is added dropwise. The slurry is stirred overnight at 0°–10° C. The resulting reaction mixture is diluted with 200 ml diethyl ether, and compound 2 is collected by filtration.

To a solution of approximately 21.5 g compound 2 in 66 ml acetonitrile at room temperature is added approximately 7.2 ml of p-methoxybenzyl chloride. The solution is stirred for approximately 1 h, then is diluted with 30% ethyl acetate/hexanes and washed with water. The organic phase is dried over sodium sulfate, and concentrated in vacuo. The residue is chromatographed over silica gel to give compound 3.

A solution of approximately 2 g compound 3 in 7 ml diphenylether is warmed under reflux for 5 min., and then allowed to cool to room temperature and diluted with approximately 70 ml hexanes. The precipitate is filtered to afford compound 4.

To a solution of approximately 2.0 g compound 4 in 32 ml dichloromethane at room temperature is added approximately 1.5 ml anisole followed by approximately 4.0 ml trifluoromethansulfonic acid. The mixture is stirred at room temperature for approximately 45 min., diluted with ethyl acetate and washed with aqueous saturated sodium bicarbonate. The aqueous phase is separated, acidified with 1N aqueous HCl, and extracted with ethyl acetate. The organic phase is dried ($MgSO_4$) and concentrated in vacuo to give compound 5.

To a solution of approximately 0.3 ml diiodomethane and approximately 0.9 g potassium carbonate in 5 mL of dimethylformamide at 70° C. is added a solution of approximately 0.63 g compound 5 in 7 mL of dimethylformamide over approximately 20 min. The solution is stirred for approximately 1 h at 70° C., then filtered and concentrated in vacuo. The residue is triturated with methanol/$CH_2Cl_2$, the precipitate is filtered to give compound 6.

A slurry of approximately 0.36 g compound 6 in 10 ml 1N sodium hydroxyde, 5 ml tetrahydrofuran, and 3 ml dioxane is refluxed overnight. The mixture is cooled to 0° C., acidified with concentrated HCl, and filtered to afford carboxylic acid 7.

To a mixture of approximately 0.30 g compound 7 and approximately 0.20 g 3-(S)-t-butycarbonylaminopyrrolidine in 2 ml DMF is added 0.3 ml triethylamine dropwise at 50°–55° C. The resulting mixture is stirred for 4 h. An equal volume of acetonitrile is added, the mixture is heated at about 75° C., and then allowed to cool to room temperature. The precipitate is collected by filtration, washed with acetonitrile and dried under reduced pressure to yield compound 8.

A mixture of approximately 0.35 g compound 8 and 0.36 ml hydrazine monohydrate in 3 ml acetonitrile is refluxed for 2.5 h. The resulting solution is diluted with acetonitrile, and is stirred for an additional 2 h at room temperature. The precipitate is collected by filtration, and treated with hot acetonitrile. Some undissolved material is removed by filtration and the filtrate is stored at room temperature overnight. Compound 9 is collected by filtration, washed with acetonitrile and dried under reduced pressure.

To a stirred mixture of approximately 0.21 gm carboxylic acid 9 in 4 ml methylene chloride is added slowly a saturated solution of HCl in ethanol at room temperature. The mixture is stirred for 4.5 h and the solid is collected by filtration. The solid is then heated at reflux in chloroform-methanol (10:1). The mixture is cooled to room temperature and compound 10 is collected by filtration, washed with chloroform and dried in vacuo.

The following compounds can be made according to Example 5, with substantially similar results:

57
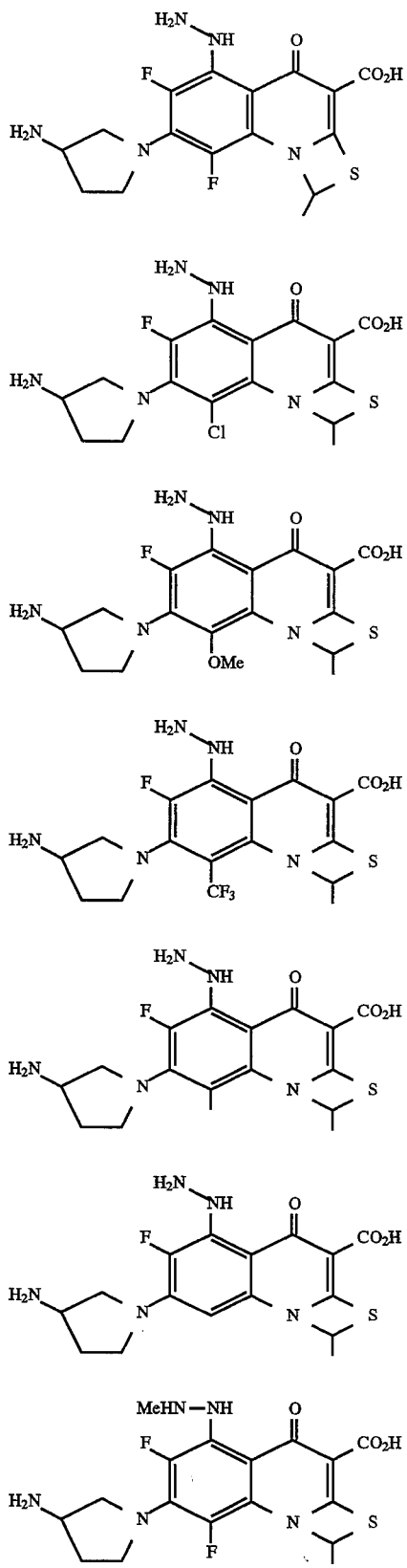
58
-continued
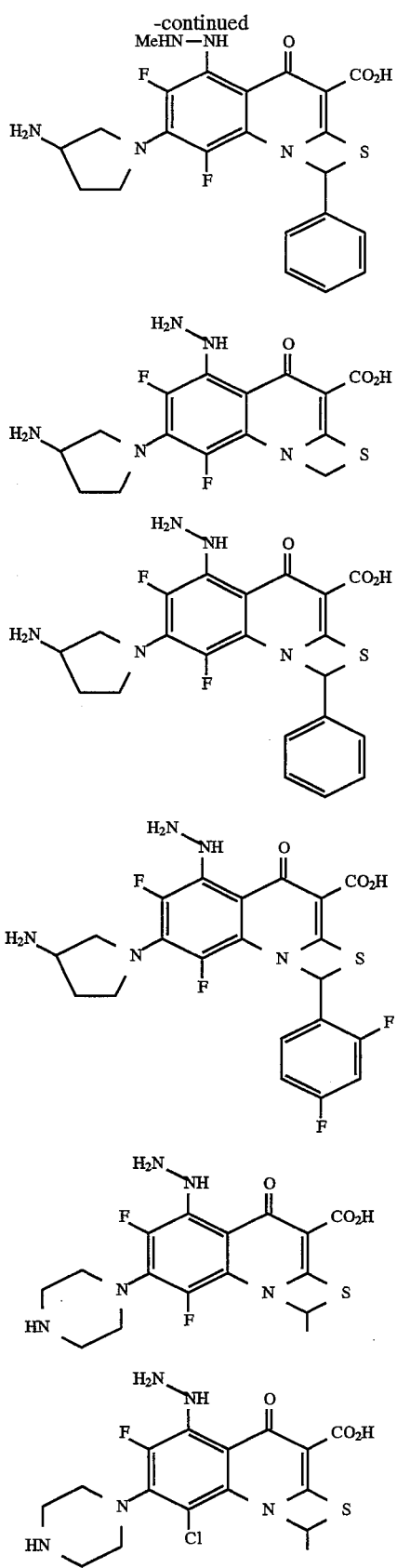

-continued
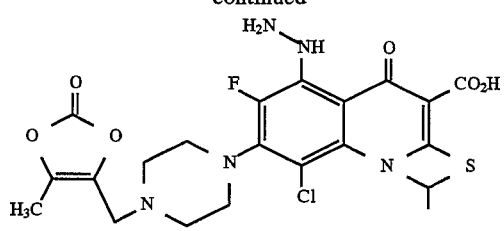
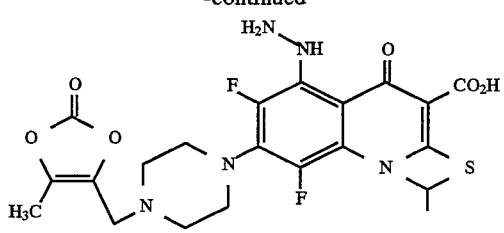
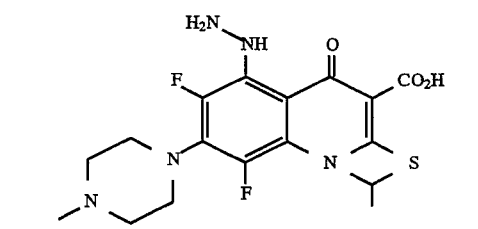
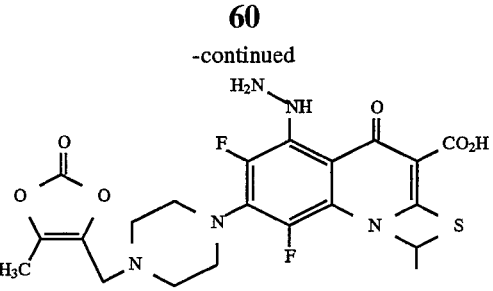
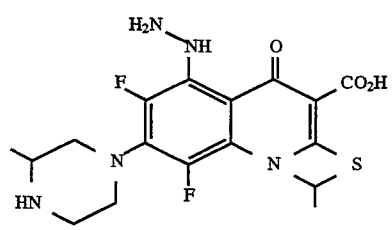
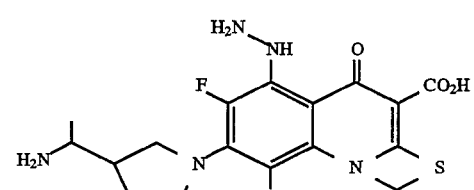
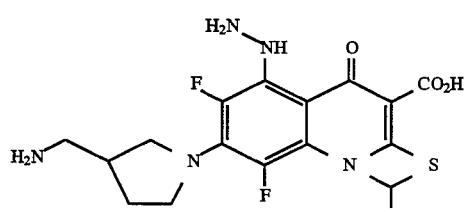
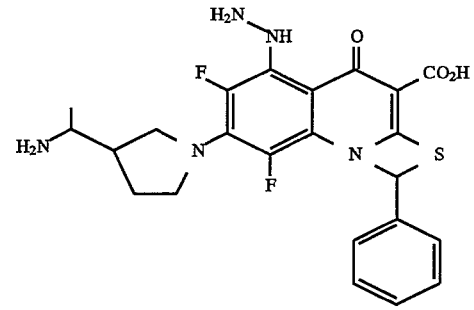
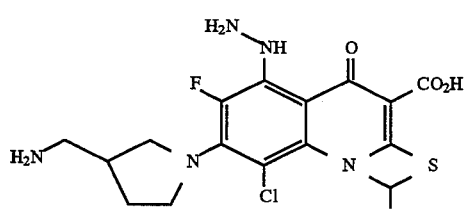
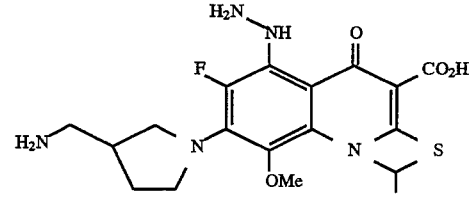
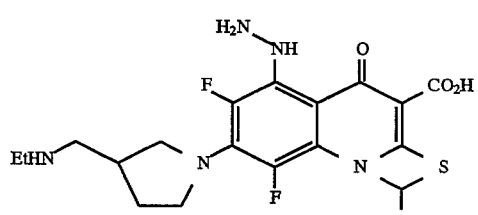
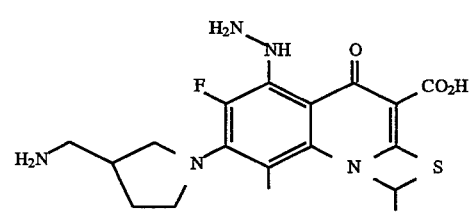
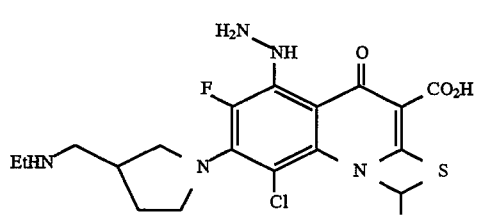
EXAMPLE 6
Synthesis of 5-(3-Amino-1-pyrrolidinyl)-6-fluoro-7-hydrazino-3,4-dihydro-4-methyl-8-oxo-8H-1-thia-4,9b-diazacyclopenta[cd]phenalene-9-carboxylic Acid Dihydrochloride

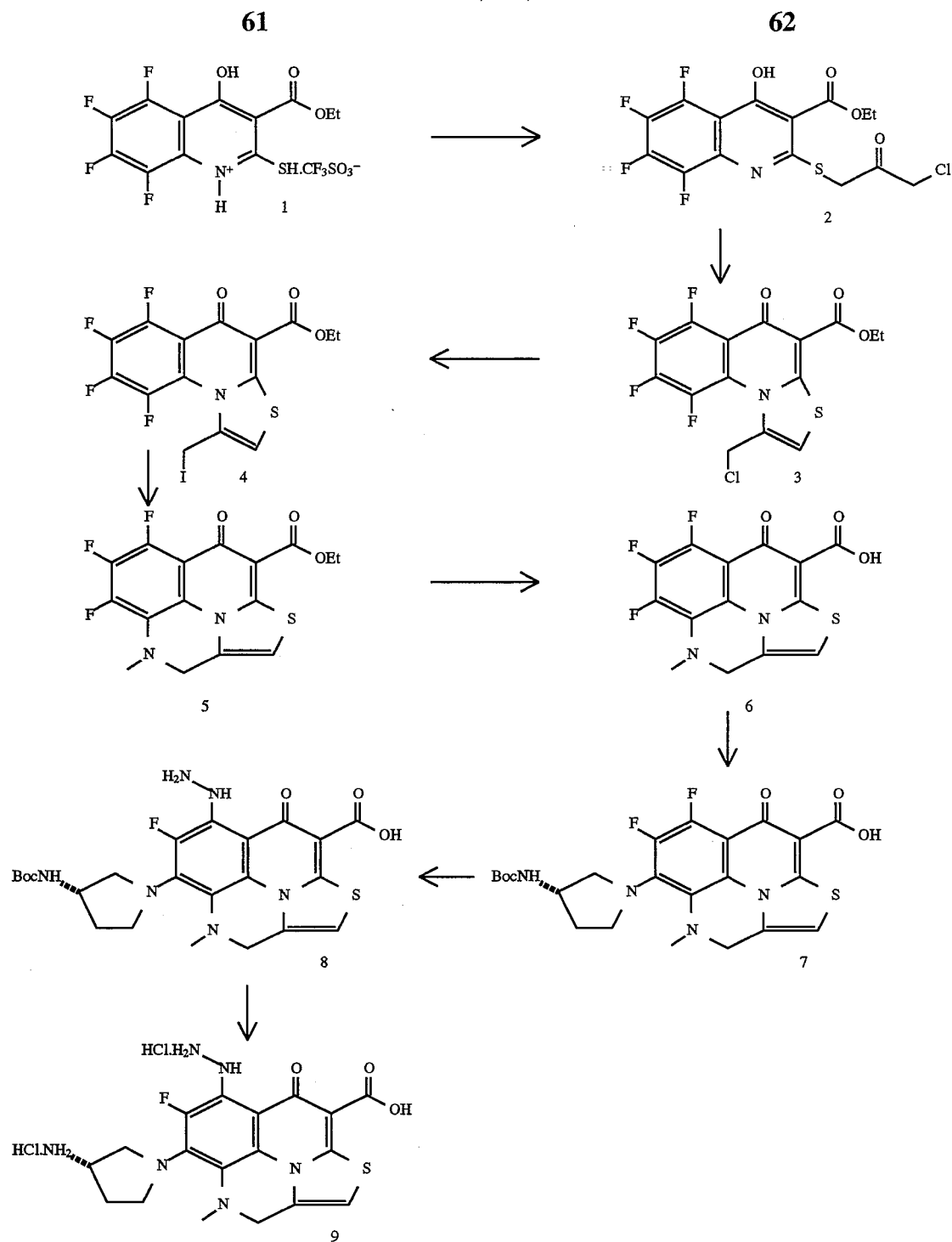

To a solution of approximately 0.18 g 1,3-dichloroacetone in 6 ml of methylene chloride at 0°–5° C. under argon is added approximately 0.47 g compound 1 (which is identical to Compound 5 prepared in Example 5) in one portion. Triethylamine (approximately 0.2 ml) is added, the mixture is stirred in the ice bath for approximately 100 minutes, and then allowed to warm to room temperature for an additional 65 minutes. The reaction is diluted with methylene chloride, and is washed sequentially with 0.1N aqueous HCl, water, and pH 7 buffer. The organic layer is dried over $MgSO_4$, and concentrated to provide compound 2.

Sulfuric acid (approximately 1.0 ml) is added to approximately 0.15 g compound 2 under argon producing a homogenous solution, which is stirred at room temperature for approximately 18 hours. The reaction is poured over a slurry of ice and approximately 20 ml of pH 7 buffer, and the mixture is extracted with chloroform. The organic layer is concentrated in vacuo to afford compound 3.

Approximately 0.05 g sodium iodide in 1.5 ml acetone is added to a mixture of approximately 0.11 g compound 3 in acetone under argon at room temperature. The mixture is refluxed for approximately 70 minutes, and cooled. The reaction is partitioned between methylene chloride and pH 7 buffer, and then the organic layer is concentrated in vacuo to provide compound 4.

To a 0°–5° C. solution of approximately 0.36 ml of methylamine/ethanol solution (8.0M) in 5 ml acetonitrile is added approximately 0.23 g compound 4 under argon. Triethylamine (approximately 0.08 ml) in approximately 1 ml of acetonitrile is then added at 0°–5° C., and the mixture is allowed to warm to room temperature with stirring overnight. The reaction is monitored by TLC and additional aliquots of methylamine/ethanol and triethylamine are added to drive the reaction to completion. The reaction is worked up by partitioning between water and chloroform. The organic layer is dried over magnesium sulfate and concentrated in vacuo to provide compound 5.

Compound 5 (approximately 0.03 g) is mixed with 1.5 ml of sulfuric acid under argon, and heated at 90°–95° C. for approximately 8 h. The reaction is cooled and approximately 20 ml of ice water is then added. The precipitated compound 6 is collected by filtration, washed with water, and dried on the high vacuum.

A mixture of compound 6 (approximately 0.4 g), approximately 0.23 g (3S)-t-butoxycarbonylaminopyrrolidine, and 2.5 ml DMF under argon is heated to 50°–55° C. Triethylamine (approximately 0.33 ml) is added dropwise, and the resulting mixture is heated with stirring for four hours. After addition of 2.5 ml of acetonitrile, the temperature is increased to approximately 75° C. and the reaction is monitored by TLC. Upon completion the reaction is then cooled to 10°–15° C., and the precipitated product (compound 7) is collected via filtration.

A mixture of approximately 0.44 g compound 7, approximately 0.41 g hydrazine hydrate, and 12 ml acetonitrile is refluxed for approximately 2.5 hours. The reaction mixture is diluted with acetonitrile and allowed to stir at room temperature for 2 hours. The product (compound 8) is collected via filtration.

Compound 8 (approximately 0.25 g) in 5 ml of methylene chloride is treated with approximately 3.2 ml of saturated HCl/ethanol, and stirred at room temperature for 4–5 hours. The reaction is diluted with methylene chloride and the product (compound 9) is collected by filtration.

The following compounds can be made according to Example 6, with substantially similar results:

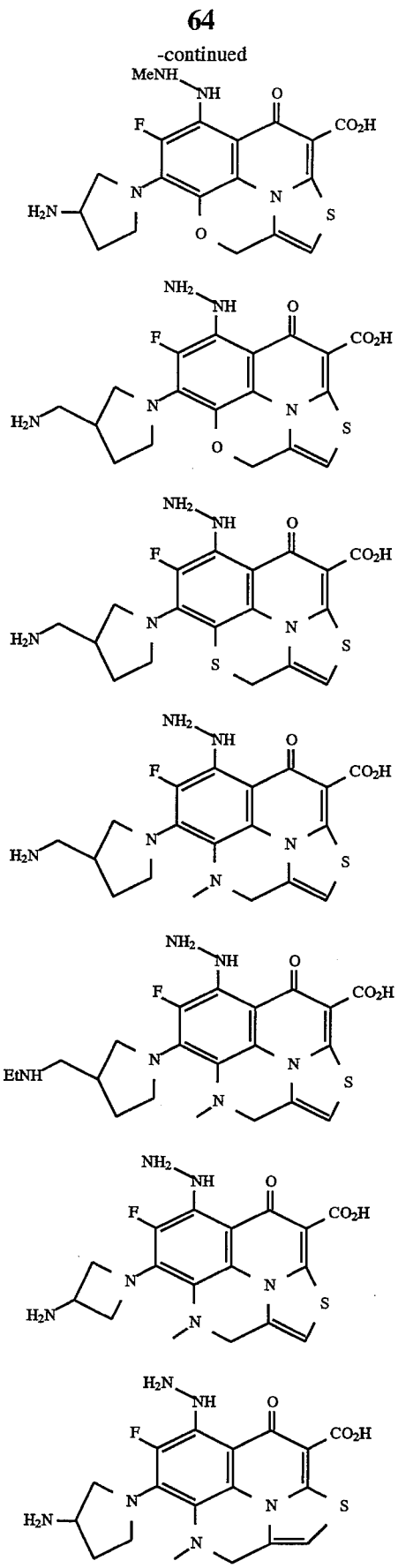

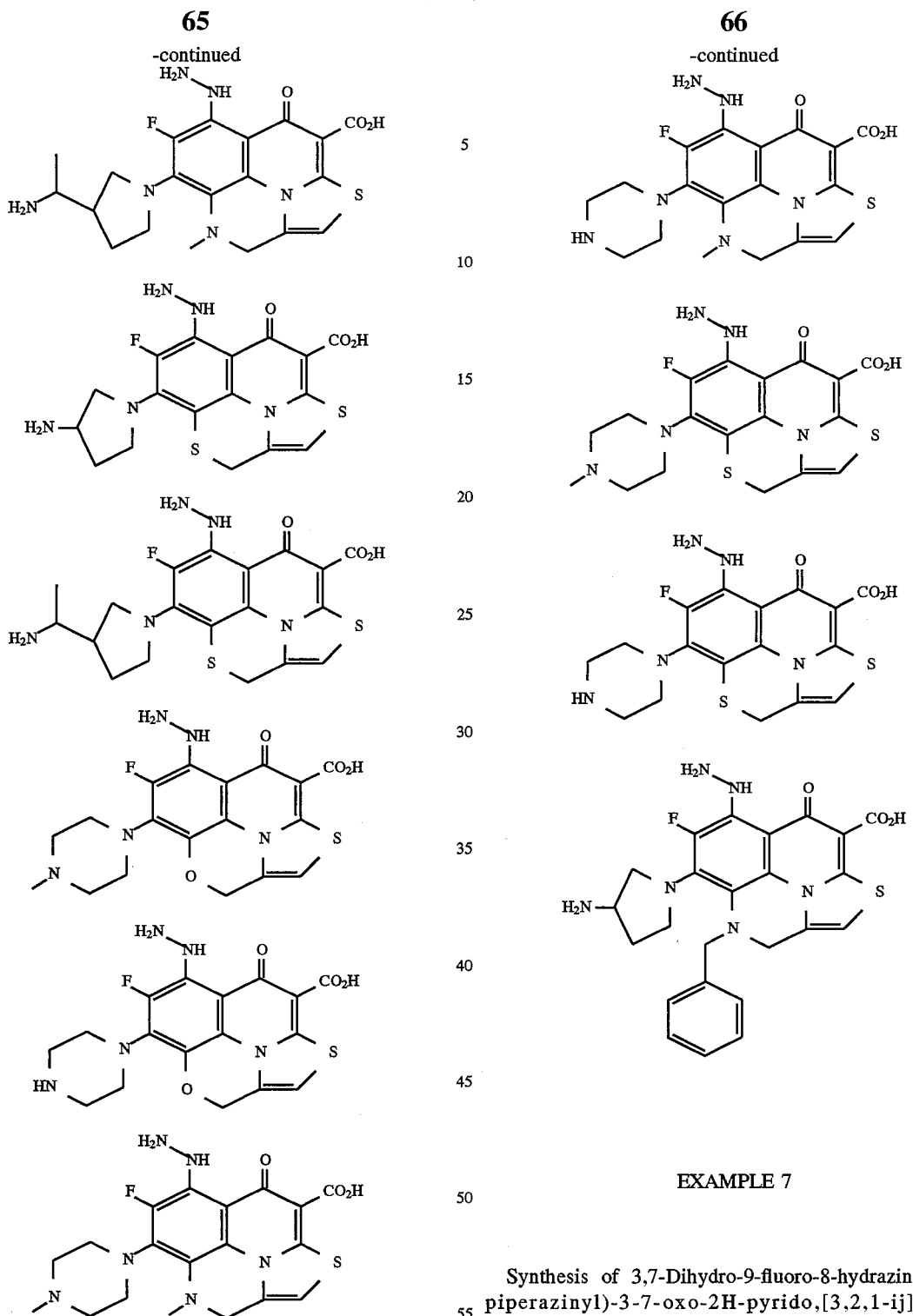
EXAMPLE 7
Synthesis of 3,7-Dihydro-9-fluoro-8-hydrazino-10-(1-piperazinyl)-3-7-oxo-2H-pyrido,[3,2,1-ij][1,3,4]benzoxadiazine-6-carboxylic Acid

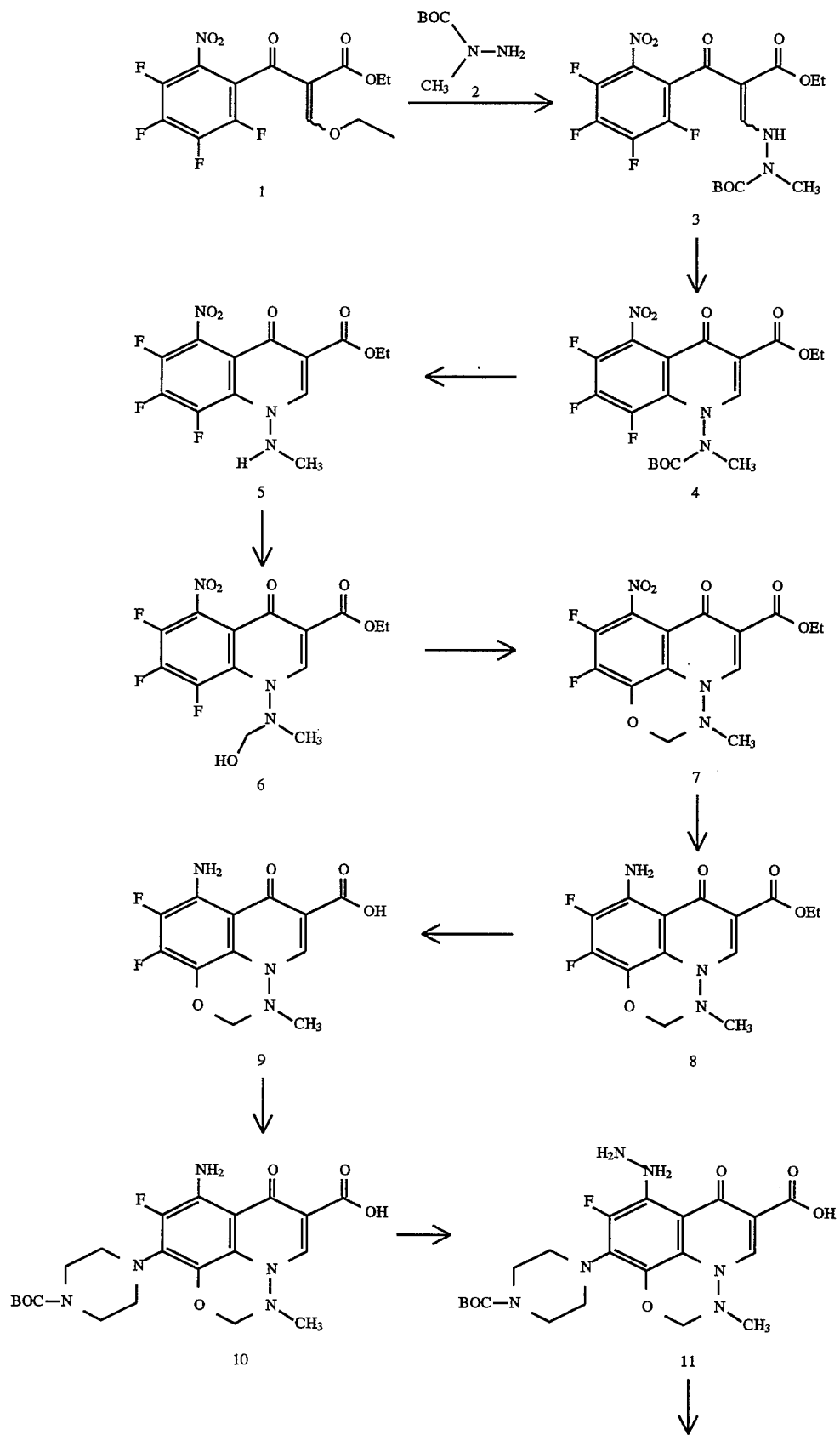

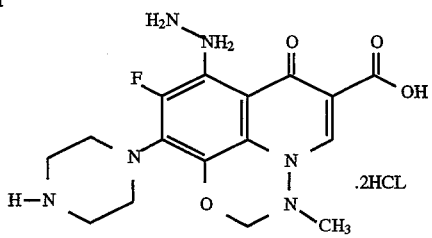

12

A stirred solution of approximately 65 g compound 1 (prepared according to J. M. Domagala et al., *J. Med. Chem.* 1991, 34(3), 1142), triethylorthoformate (approximately 52 ml), and 47 ml acetic anhydride is refluxed for 2 hours and the volatiles are removed under high vacuum. The resulting oil is dissolved in t-butyl alcohol (50–55 ml) and the solution is added to a solution of 2 (approximately 32 g; prepared according to A. Dutta and I. Morley, *J. Chem. Soc.*, Perkin Trans. 1 1975, 17, 1712) in t-butyl alcohol (140 ml) at 10°–15° C. The reaction is kept below approximately 40° C., and is stirred at ambient temperature for 2 hours. The product (compound 3) is collected by filtration To a solution of approximately 83 g compound 3 in dry THF (850 ml) at 0° C. is added 60% sodium hydride in mineral oil (approximately 8.4 g) in portions. After the hydrogen evolution ceases, the mixture is refluxed for approximately one hour, and then is stirred at ambient temperature for one hour. The solvent is removed under reduced pressure. The residue is treated with ice cold water, and the mixture is extracted with dichloromethane. The organic phase is washed with water, dried over magnesium sulfate, concentrated in vacuo to give compound 4.

To a solution of approximately 51 ml triethylsilane in 500 ml trifluoroacetic acid at 0° C. is added approximately 70 g compound 4 in portions. The reaction is stirred at 0° C. for approximately one hour and is concentrated to dryness at 0°–5° C. under high vacuum. The residue is stirred in diethyl ether for 2 hours, and the product is collected by filtration to give compound 5.

A mixture of approximately 50 g compound 5, approximately 184 g paraformaldehyde, and 3600 ml distilled water is refluxed for approximately 40 hours, and the reaction is cooled to room temperature. The mixture is extracted with dichloromethane and the extract is washed with water. The organic phase is dried over magnesium sulfate, filtered and concentrated under reduced pressure until a precipitate begins to form. Then the mixture is diluted with diethyl ether and the product (compound 6) is collected by filtration.

To a mixture of approximately 5 g compound 6 in 1000 ml dry THF at reflux is added 1.0M tetrabutylammonium fluoride in THF (approximately 30 ml) rapidly, and the reaction is refluxed for approximately 20 minutes. The reaction is poured into 10% aqueous sodium bicarbonate at about 10° C. and the product is extracted with dichloromethane. The organic phase is washed with brine, dried over magnesium sulfate, filtered and the filtrate is concentrated to dryness. The residue is dissolved in acetone and diluted with ether. The crude product is collected by filtration, and further purified by chromatography over silica gel to give compound 7.

A suspension of approximately 6 g compound 7 in 165 ml 50% THF/EtOH is shaken with approximately 0.8 g of RaNi at approximately 30 psi $H_2$ for 16–18 hours. Additional THF (500 ml) is added, the mixture is heated and is filtered. The filtrate is concentrated to about 80 ml and the product is collected by filtration to give compound 8.

A mixture of approximately 4.9 g compound 8 in 6N aqueous HCl is refluxed for approximately 2 hours, cooled to room temperature and the solid is collected by filtration, washing well with water and ether. The product is thoroughly dried under high vacuum to give compound 9.

A mixture of compound 9 (approximately 4.3 g), approximately 16 g t-butyl 1-piperazinecarboxylate, and 20 ml DMSO is heated at approximately 110° C. for about 2 hours, cooled to room temperature, and diluted with ether. The solid is collected by filtration. The product is triturated in acetonitrile and collected by filtration to give compound 10.

To a solution of approximately 3 g compound 10 in 67 ml dichloromethane at –40° C. is added nitrosonium tetrafluoroborate (approximately 0.9 g). The reaction is stirred at –42° C. to –37° C. for approximately 2.5 hours and diluted with pentane. The liquid is decanted and the residue is stirred in diethyl ether. The diazonium intermediate is collected by filtration, and stirred in dichloromethane (55 ml). To this mixture is added approximately 2.2 ml benzeneselenol, and the reaction is refluxed for approximately 3.5 hours. The reaction is cooled to room temperature, and is diluted with an equal volume of diethyl ether. The solid is collected by filtration, and purified by silica gel chromatography to give compound 11.

To a mixture of compound 11 (approximately 0.5 g) in 11 ml dichloromethane at room temperature is added saturated ethanol/HCl (7 ml) slowly with stirring. The mixture is stirred at room temperature for approximately 4.5 hours, and the solid is collected by filtration. This material is heated in chloroform (13 ml) and methanol (1.4 ml) is added. The mixture is cooled to room temperature, and the product is collected by filtration to give compound 12.

The following compounds can be prepared according to Example 7, with substantially similar results:

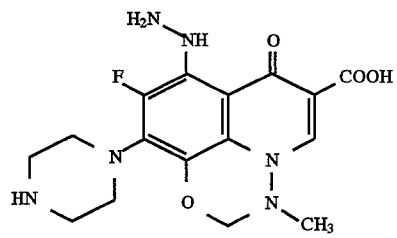

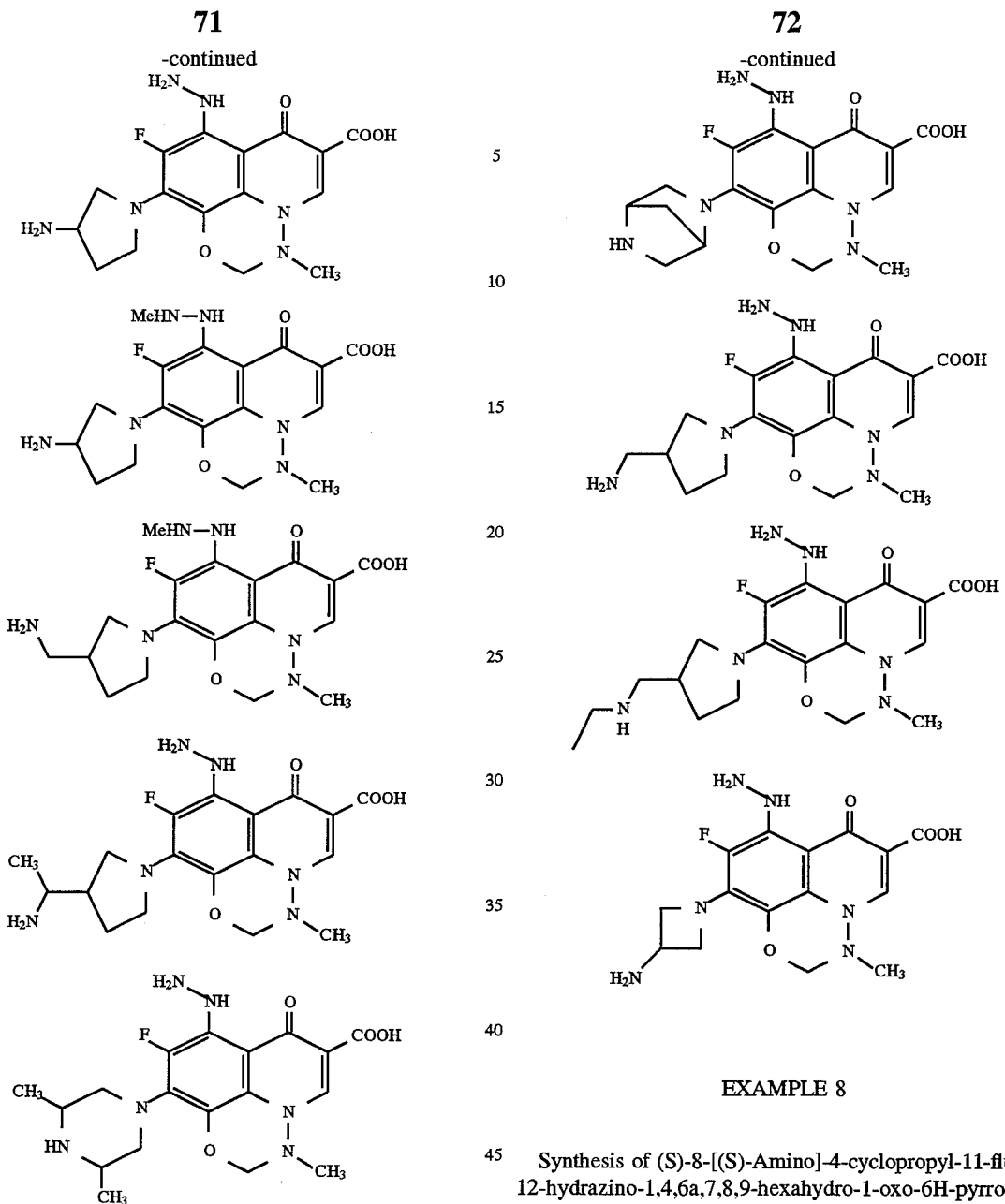
EXAMPLE 8
Synthesis of (S)-8-[(S)-Amino]-4-cyclopropyl-11-fluoro-12-hydrazino-1,4,6a,7,8,9-hexahydro-1-oxo-6H-pyrrolo[1',2'4,5][1,4]oxazino[3,2-h]quinoline-2-carboxylic Acid Dihydrochloride

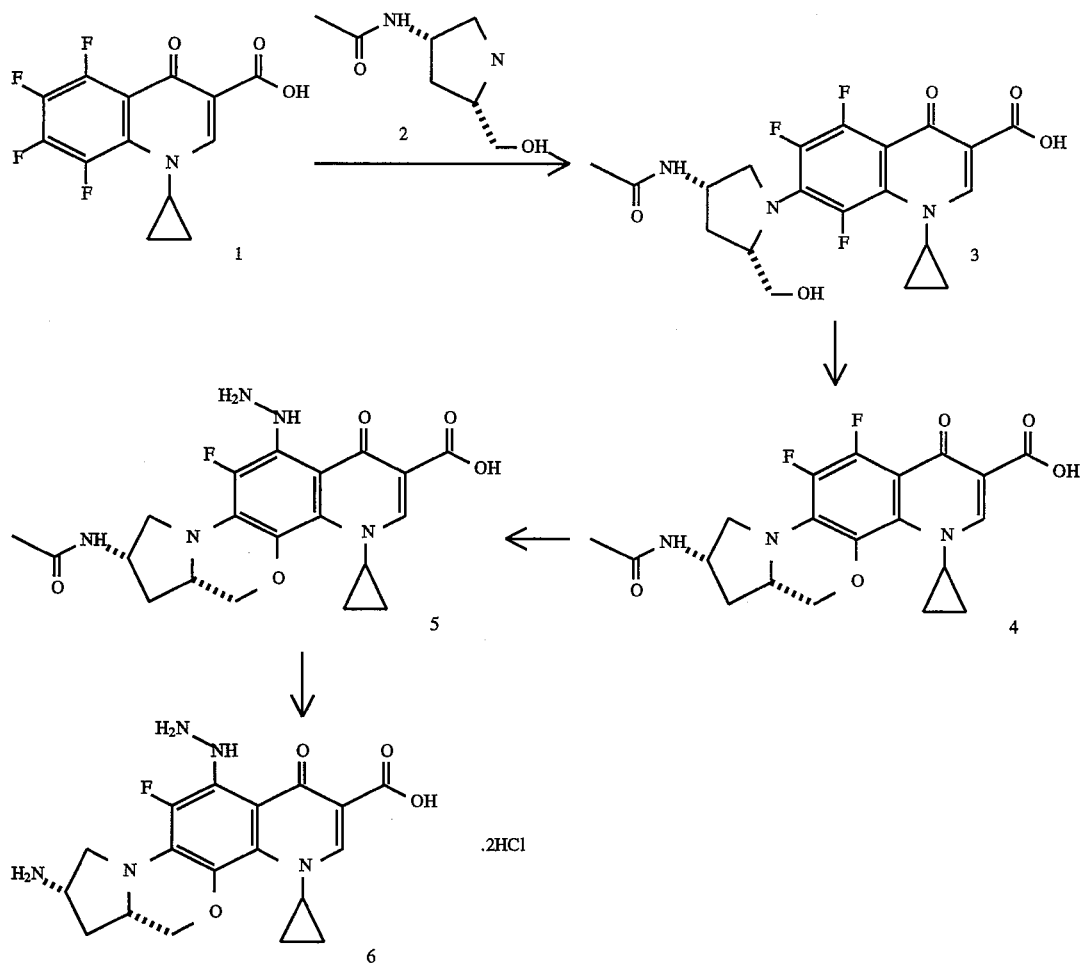

To a solution of 20 ml pyridine, approximately 3.3 gm triethylamine, and approximately 8.0 g compound 2 (prepared according to T. Rosen et al., *J. Med. Chem.* 1988, vol. 31, 1598) is added approximately 18 g compound 1, and the reaction is stirred at approximately 40° C. for 20 hours. The reaction is concentrated to an oil under reduced pressure, toluene is added and again concentrated. The residue is purified by silica gel chromatography to afford compound 3.

To a mixture of approximately 7.0 g compound 3 in 210 ml dry DMF is added approximately 1.7 g sodium hydride (60% in mineral oil). The mixture is stirred for one hour at room temperature, and then is stirred at approximately 140° C. for about 3 hours. The reaction is concentrated to dryness, the residue is stirred in $H_2O$ and neutralized with 1N aqueous HCl. The solid is collected by filtration and purified by silica gel chromatography to give compound 4.

Compound 4 (approximately 4.8 g) in acetonitrile is heated in the presence of a large excess of hydrazine hydrate for approximately 5 hours. The reaction is cooled to room temperature and diluted with additional acetonitrile. The mixture is stirred for one hour, the solid is collected by filtration and recrystallized to give compound 5.

Compound 5 (approximately 1.8 g) is heated in 10 ml 2N aqueous NaOH at 95°–100° C. for approximately 20 hours. The reaction is cooled, adjusted to pH 2–3 with 6N aqueous HCl, and concentrated to dryness under high vacuum. The solid is dissolved in $H_2O$, and filtered through a pad of C-18 silica gel, washing with $H_2O$. The product is washed off the pad with 50% acetonitrile/water, the filtrate is concentrated, and the product is further purified by reverse phase (C-18) HPLC to give compound 6.

The following compounds can be prepared according to Example 8, with substantially similar results:

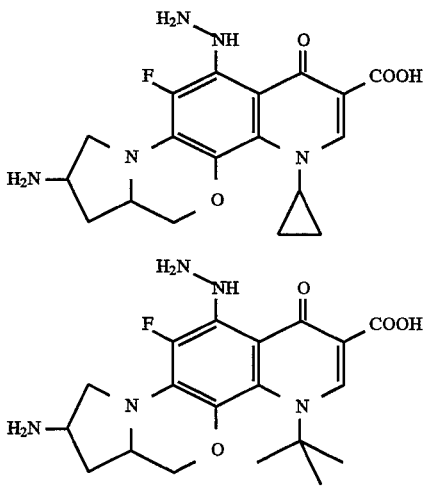

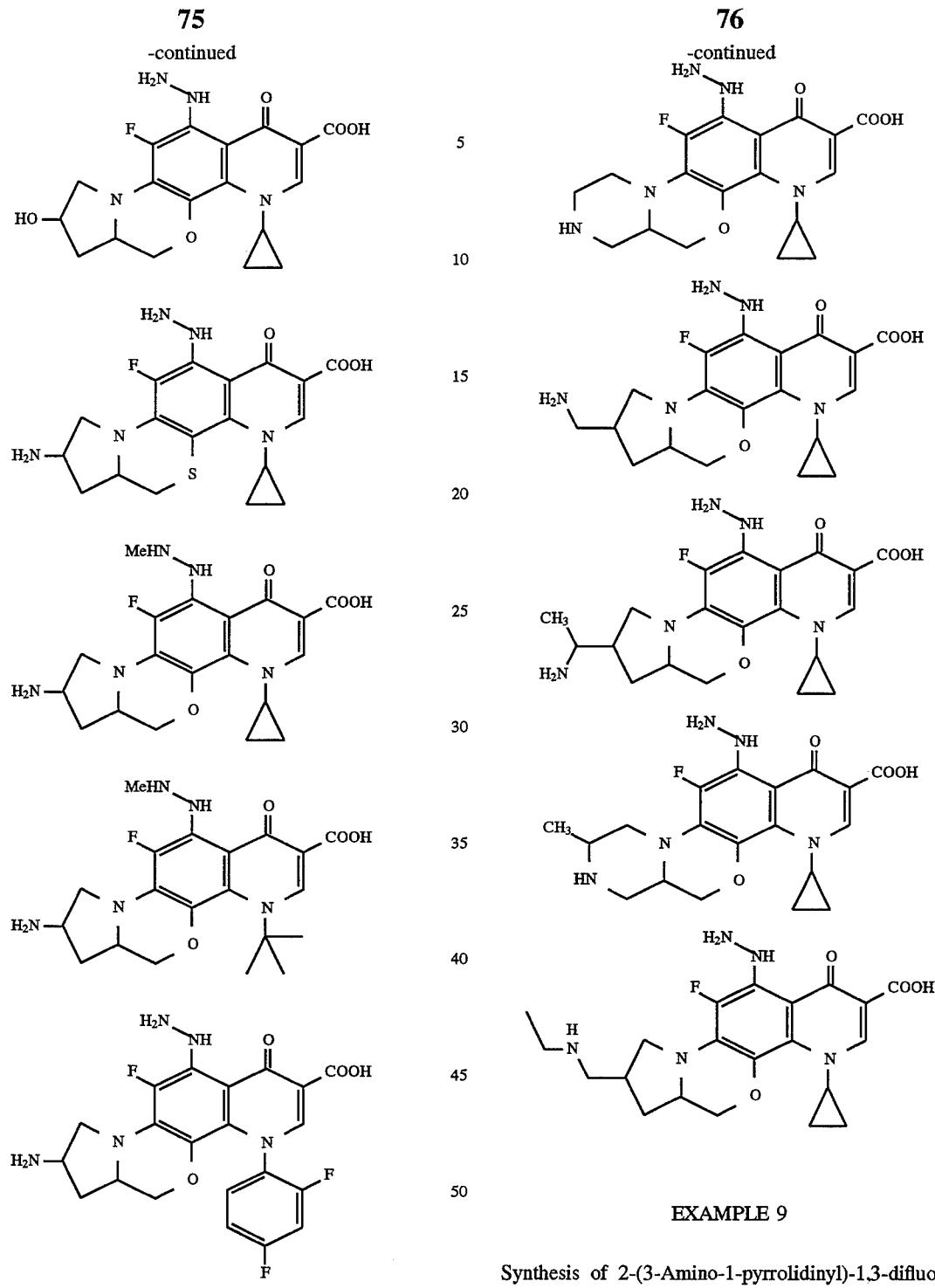
EXAMPLE 9
Synthesis of 2-(3-Amino-1-pyrrolidinyl)-1,3-difluoro-4-hydrazino-5-oxo-5H-benzothiazolo[3,2-a]quinolone-6-carboxylic Acid Dihydrochloride

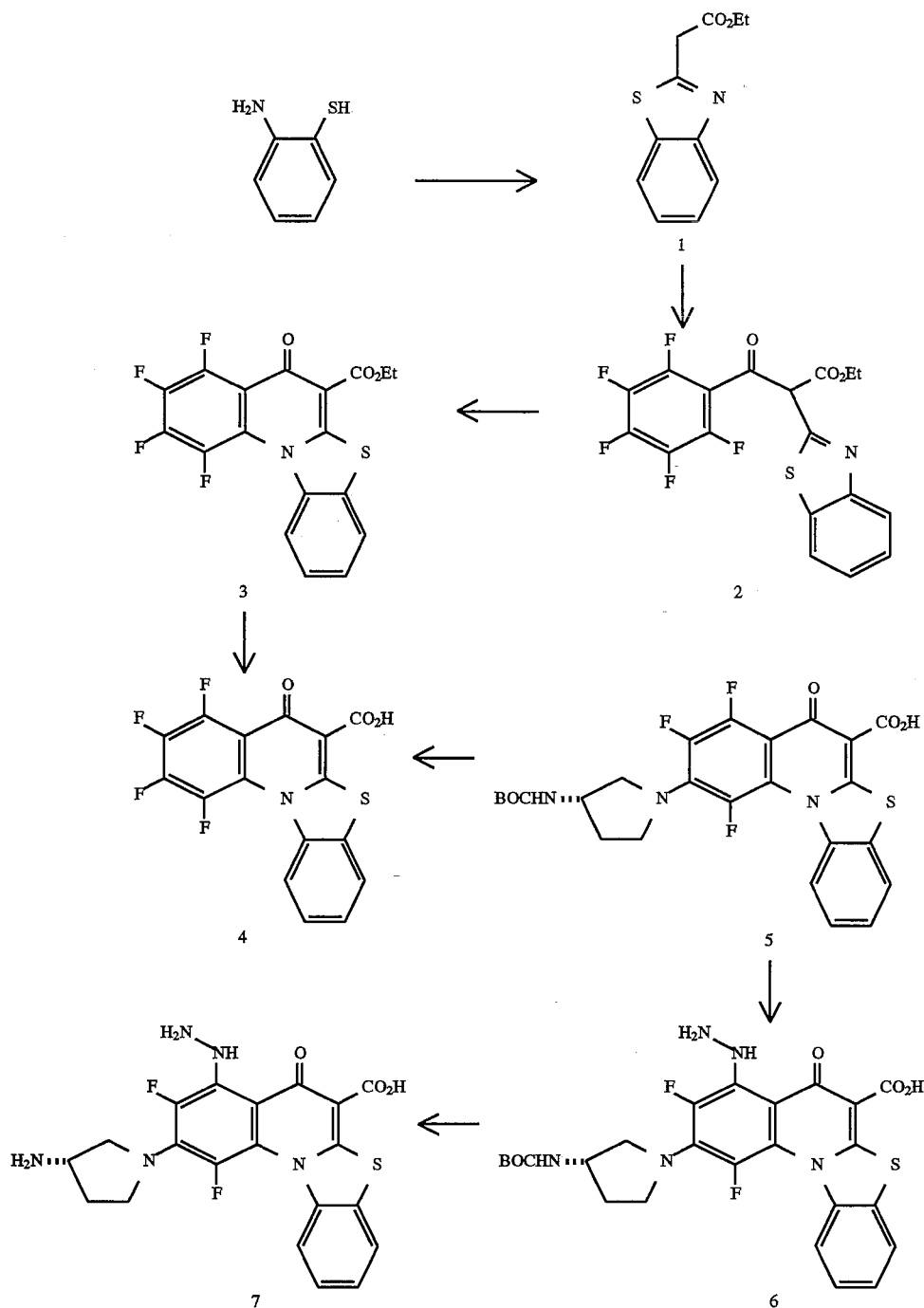

Ethyl malonyl chloride, (approximately 5.0 g) is added neat to a solution of approximately 3.6 ml 2-aminothiophenol and approximately 4.6 ml triethylamine in anhydrous diethyl ether, and the mixture is stirred for 2–3 hours at room temperature. The triethylamine hydrochloride salt is filtered and washed thoroughly with diethyl ether. The product is purified by distillation yielding compound 1.

Approximately 5.4 g compound 1 dissolved in 100 ml anhydrous THF is added slowly to a cold solution of approximately 1.1 g sodium hydride (60% in mineral oil) suspended in anhydrous THF. After stirring for 1 hour, a solution of pentafluorobenzoyl chloride in 60 ml anhydrous THF is added dropwise over a period of 15 minutes. The reaction mixture is stirred at 25° C. for 2 hours. The solvent is removed under reduced pressure, and the residue is redissolved in ethyl acetate. The organic layer is washed with water and saturated aqueous sodium chloride, then dried over magnesium sulfate. Removal of solvent in vacuo yields a solid which is recrystallized to give compound 2.

Compound 2 (approximately 4.0 g) dissolved in 75 ml ethylene glycol dimethyl ether is added slowly to a solution of approximately 0.42 g sodium hydride (60% in mineral oil) in 75 ml ethylene glycol dimethyl ether. The mixture is heated at approximately 160° C. for 30 min. The reaction is allowed to cool to room temperature, then treated with cold water. The precipitate is collected and washed with water, yielding compound 3.

Compound 3 (approximately 0.5 g) in 15 ml of 2N sulfuric acid is refluxed at 100° C. for 18 hours. The mixture is cooled to room temperature, and the pH is adjusted to 6.5. The precipitate is collected and washed with water, then acetone to yield compound 4.

Approximately 0.5 g of compound 4 and approximately 0.3 g of (3S)-t-butoxycarbonylaminopyrrolidine in 3 ml of DMF is heated to 50°–55° C., then treated dropwise with 0.4 ml of triethylamine. The mixture is stirred at this temperature for approximately 4 hours. Acetonitrile (3 ml) is added to the mixture and heated at 75° C., then allowed to cool to approximately 15° C. The solid is collected by filtration, and washed with acetonitrile to yield compound 5.

Compound 5 (approximately 0.5 g), 15 ml of acetonitrile, and 0.5 ml of hydrazine monohydrate is refluxed for about 2.5 hours. The solution is diluted with 10 ml of acetonitrile and stirred for 2 hours at approximately 15° C. The precipitate is collected and digested in 15 ml of hot acetonitrile. The solution is filtered to remove insolubles and stored at room temperature overnight. The product is collected and washed with cold acetonitrile to yield compound 6.

Compound 6 (approximately 0.5 g) in 10 ml of dichloromethane is slowly treated with 6 ml of a saturated ethanol/HCl solution. After vigorous stirring at room temperature for 4.5 hours, the solid is collected. The product is resuspended and heated in 10 ml of chloroform containing 1 ml of methanol. The solution is cooled to room temperature, and the precipitate is collected and washed with chloroform to yield compound 7.

The following compounds can be prepared according to Example 9, with substantially similar results:

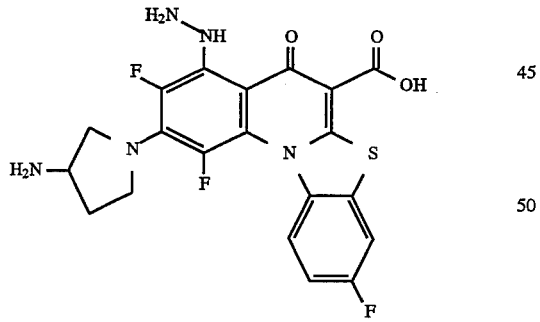

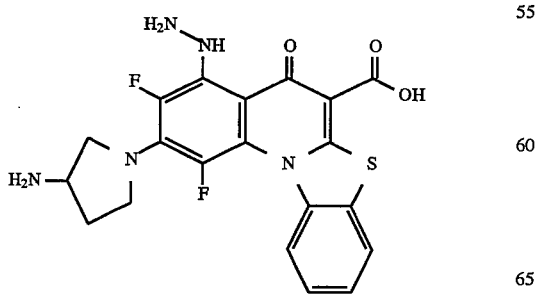

-continued

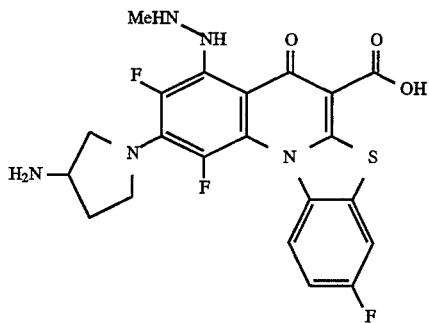

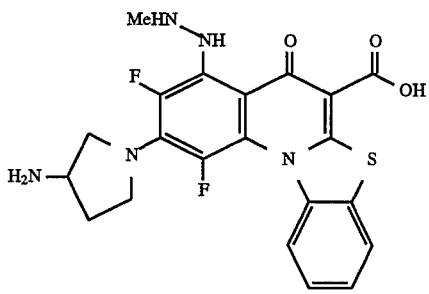

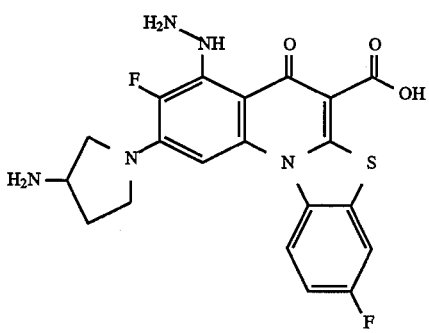

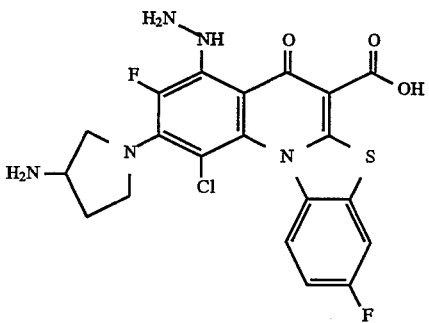

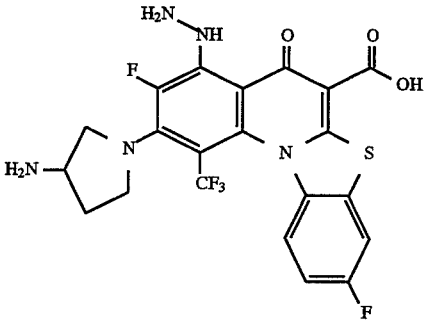

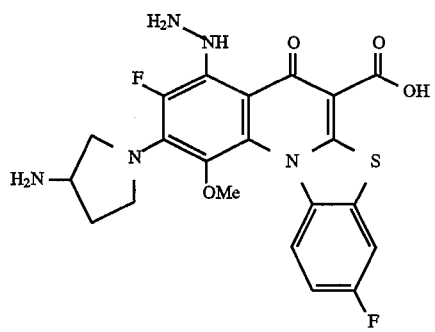
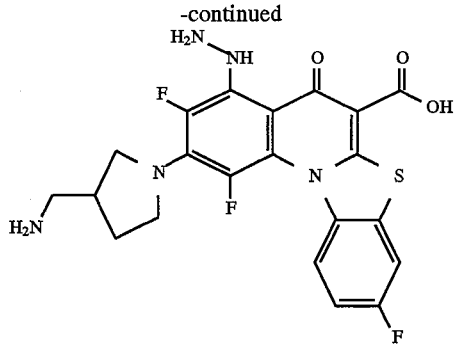
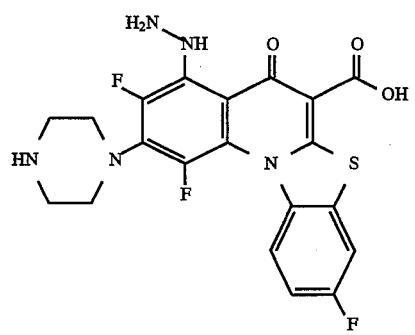
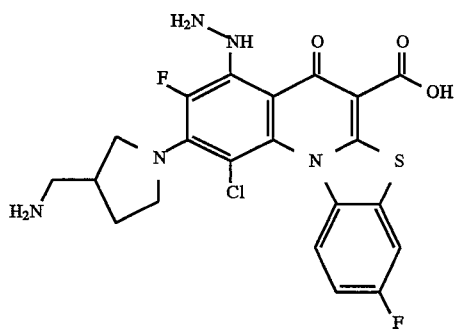
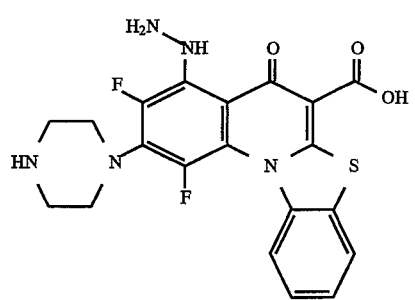
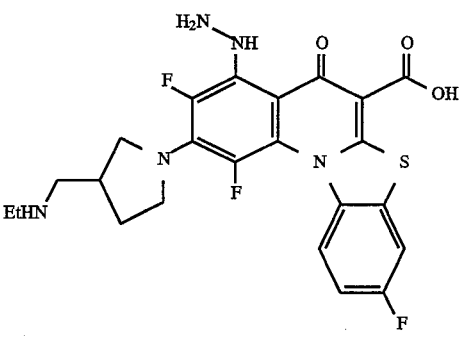
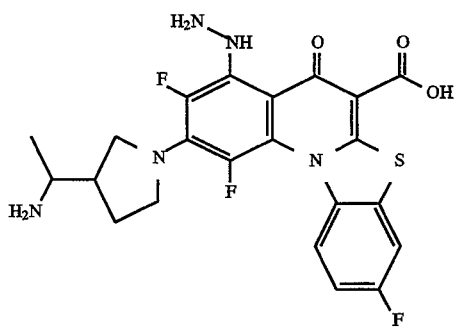
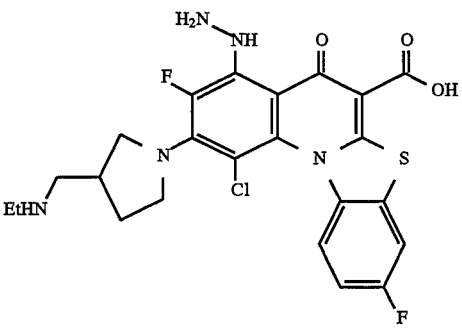
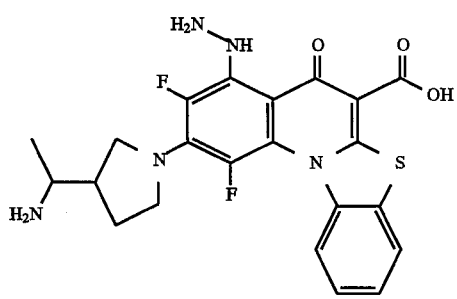
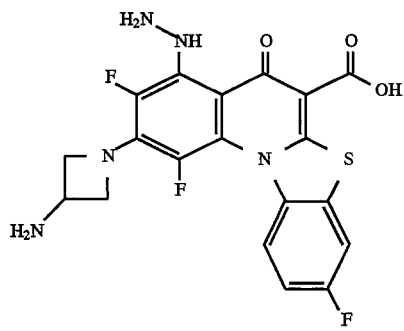

-continued

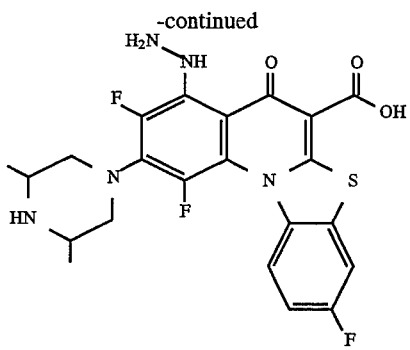

EXAMPLE 10

An antimicrobial composition for parenteral administration, according to this invention, is made comprising:

| Component | Amount |
|---|---|
| (S)-7-(3-Aminopyrrolidine)-1-cyclopropyl-6,8-difluoro-5-hydrazino-1,4-dihydro-4-oxo-3-quinoline carboxylic acid[1] | 100 mg/ml carrier |
| Carrier: | |
| sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

[1] a 5-(N-heterosubstituted amino) quinolone made according to Example 1.

The above ingredients are mixed, forming a suspension. Approximately 2.0 ml of the suspension is systemically administered, via intramuscular injection, to a human subject suffering from a lower respiratory tract infection, with *Streptococcus pneumonia* present. This dosage is repeated twice daily, for approximately 14 days. After 4 days, symptoms of the disease subside, indicating that the pathogen has been substantially eradicated.

EXAMPLE 11

An enteric coated antimicrobial composition for oral administration, according to this invention, is made comprising the following core tablet:

| Component | Amount (mg) |
|---|---|
| (S)-7-(3-Aminopyrrolidine)-1-cyclopropyl-6,8-difluoro-5-hydrazino-1,4-dihydro-4-oxo-3-quinoline carboxylic acid[1] | 350.0 |
| starch | 30.0 |
| magnesium stearate | 5.0 |
| microcrystalline cellulose | 100.0 |
| colloidal silicon dioxide | 2.5 |
| povidone | 12.5 |

[1] a 5-(N-heterosubstituted amino) quinolone made according to Example 1.

The components are admixed into a bulk mixture. Compressed tablets are formed, using tabletting methods known in the art. The tablet is then coated with a suspension of methacrylic acid/methacrylic acid ester polymer in isopropanol/acetone. A human subject, having a urinary tract infection with *Escherichia coli* present, is orally administered two of the tablets, every 8 hours, for 14 days. Symptoms of the disease then subside, indicating substantial eradication of the pathogen.

What is claimed is:

1. A compound having a structure according to Formula (I), or a pharmaceutically-acceptable salt, biohydrolyzable ester, biohydrolyzable amide, or solvate thereof:

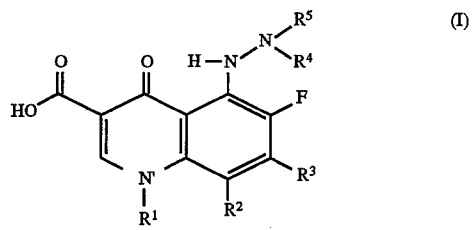

wherein
(A)
(1)
(a) $R^1$ is alkyl; alkenyl; a carbocyclic ring; a heterocyclic ring; or —$N(R^6)(R^7)$, where $R^6$ and $R^7$ are, independently, hydrogen, alkyl, alkenyl, a carbocyclic ring, a heterocyclic ring, or $R^6$ and $R^7$ together comprise a heterocyclic ring that includes the nitrogen to which they are bonded; and
(b) $R^2$ is hydrogen, halogen, lower alkyl, or lower alkoxy;
(B) $R^3$ is a heterocyclic ring or a carbocyclic ring; and
(C)
(1) $R^4$ and $R^5$ are, independently, hydrogen; lower alkyl; cycloalkyl; heteroalkyl; or —C(=O)—X—$R^8$, where X is a covalent bond, N, O, or S, and $R^8$ is lower alkyl, lower alkenyl, arylalkyl, a carbocyclic ring, or a heterocyclic ring; or
(2) $R^4$ and $R^5$ together comprise a heterocyclic ring that includes the nitrogen to which they are bonded.

2. A compound, according to claim 1, wherein $R^1$ is ethyl, 2-fluoroethyl, 2-hydroxyethyl, t-butyl, 4-fluorophenyl, 2,4-difluorophenyl, methylamino, cyclopropyl, or 2-fluorocyclopropyl.

3. A compound, according to claim 1, wherein $R^2$ is chlorine or fluorine.

4. A compound, according to claim 1, wherein $R^4$ is hydrogen and $R^5$ is hydrogen or lower alkyl.

5. A compound, according to claim 4, wherein both $R^4$ and $R^5$ are hydrogen.

6. A compound, according to claim 5, wherein $R^3$ is a heterocyclic ring.

7. A compound, according to claim 6, wherein said heterocyclic ring is 3-aminopyrrolidine.

8. A compound, according to claim 7, wherein $R^1$ is cyclopropyl and $R^2$ is fluorine.

9. A compound, according to claim 7, wherein $R^1$ is 2,4-difluorophenyl and $R^2$ is fluorine.

10. A compound, according to claim 6, wherein said heterocyclic ring is piperazine.

11. A compound, according to claim 10, wherein $R^1$ is cyclopropyl and $R^2$ is fluorine.

12. A compound, according to claim 4, wherein $R^5$ is lower alkyl.

13. A compound, according to claim 12, wherein $R^3$ is a heterocyclic ring.

14. A compound, according to claim 13, wherein said heterocyclic ring is 3-aminopyrrolidine.

15. A compound, according to claim 14, wherein $R^1$ is cyclopropyl and $R^2$ is fluorine.

16. A compound, according to claim 13, wherein said heterocyclic ring is piperazine.

17. A compound, according to claim 16, wherein $R^1$ is cyclopropyl and $R^2$ is fluorine.

18. A compound selected from the group consisting of
   (3S)-7-(3-amino-1-pyrrolidinyl)-1-(2,4,difluorophenyl)-6,8-difluoro-5-hydrazino-1,4-dihydro-4-oxo-3-quinolinecarboxylic acid;
   (3S)-7-(3-amino-1-pyrrolidinyl)-1-cyclopropyl-6,8-difluoro-5-hydrazino-1,4-dihydro-4-oxo-3-quinolinecarboxylic acid; and
   1-cyclopropyl-6,8-difluoro-5-hydrazino-1,4-dihydro-4-oxo-7-piperazinyl-3-quinolinecarboxylic acid;
   and the pharmaceutically-acceptable salts, biohydrolyzable esters, biohydrolyzable amides, and solvates thereof.

19. A composition for treating or preventing bacterial infections in a human or other animal subject, comprising:
   (1) a safe and effective amount of a compound of claim 1; and
   (2) a pharmaceutically-acceptable carrier.

20. A method for preventing or treating bacterial infections in a human or other animal subject, by administering to said subject a safe and effective amount of a compound of claim 1.

* * * * *